United States Patent
Lee et al.

(10) Patent No.: US 12,172,037 B2
(45) Date of Patent: Dec. 24, 2024

(54) SYSTEMS AND METHODS FOR MECHANOGENETIC FUNCTIONAL ULTRASOUND IMAGING

(71) Applicant: The Board of Trustees of the Leland Stanford Junior University, Stanford, CA (US)

(72) Inventors: Jin Hyung Lee, Palo Alto, CA (US); Bradley Jay Edelman, Sunnyvale, CA (US); Peter Lin, Stanford, CA (US); Jan Liphardt, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 249 days.

(21) Appl. No.: 17/633,920

(22) PCT Filed: Aug. 6, 2020

(86) PCT No.: PCT/US2020/045209
§ 371 (c)(1),
(2) Date: Feb. 8, 2022

(87) PCT Pub. No.: WO2021/030145
PCT Pub. Date: Feb. 18, 2021

(65) Prior Publication Data
US 2022/0296932 A1   Sep. 22, 2022

Related U.S. Application Data

(60) Provisional application No. 62/887,163, filed on Aug. 15, 2019.

(51) Int. Cl.
*A61N 7/00* (2006.01)
*A61B 8/08* (2006.01)
*C07K 14/705* (2006.01)

(52) U.S. Cl.
CPC ............. *A61N 7/00* (2013.01); *A61B 8/0808* (2013.01); *C07K 14/705* (2013.01); *A61N 2007/0021* (2013.01)

(58) Field of Classification Search
CPC ...... A61B 5/4064; A61B 8/0808; A61N 7/00; A61N 2007/0026; A61N 2007/0021
See application file for complete search history.

(56) References Cited

U.S. PATENT DOCUMENTS

2010/0063397 A1   3/2010   Wagner
2011/0054324 A1   3/2011   Lee
(Continued)

FOREIGN PATENT DOCUMENTS

WO   WO 2012/131418   10/2012

OTHER PUBLICATIONS

Osmanski et al., (2014) "Functional Ultrasound Imaging of Intrinsic Connectivity in the Living Rat Brain with High Spatiotemporal Resolution", Nature Communications 5(5023):1-14.

*Primary Examiner* — Amelie R Davis
(74) *Attorney, Agent, or Firm* — Rudy J. Ng; Bozicevic, Field & Francis LLP

(57) ABSTRACT

The present disclosure provides a system for functional ultrasound imaging, where the system comprises: a) an apparatus for delivering a nucleic acid encoding a mechanosensitive ion channel to a target neural cell population in a region of a brain; and b) a functional ultrasound imaging device. The present disclosure provides a method for functional ultrasound imaging.

19 Claims, 25 Drawing Sheets

Specification includes a Sequence Listing.

(56) References Cited

U.S. PATENT DOCUMENTS

| | | | |
|---|---|---|---|
| 2011/0118598 A1* | 5/2011 | Gertner | A61B 18/1492 |
| | | | 600/431 |
| 2013/0035660 A1* | 2/2013 | Anand | A61M 25/0023 |
| | | | 604/173 |
| 2016/0220672 A1 | 8/2016 | Chalasani et al. | |
| 2018/0177487 A1* | 6/2018 | Deffieux | A61B 8/0816 |
| 2019/0308035 A1 | 10/2019 | Sun et al. | |

* cited by examiner

FUS Imaging of Hindlimb Electrical Stimulation
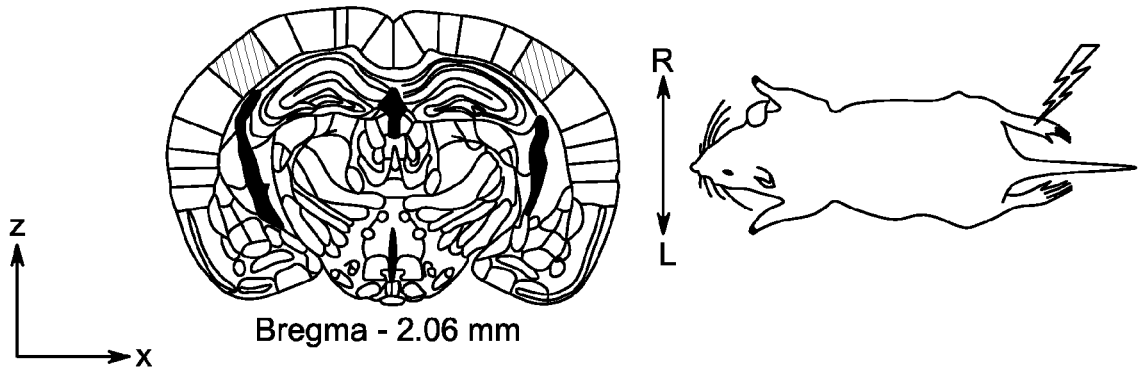
Bregma - 2.06 mm
Activation Map
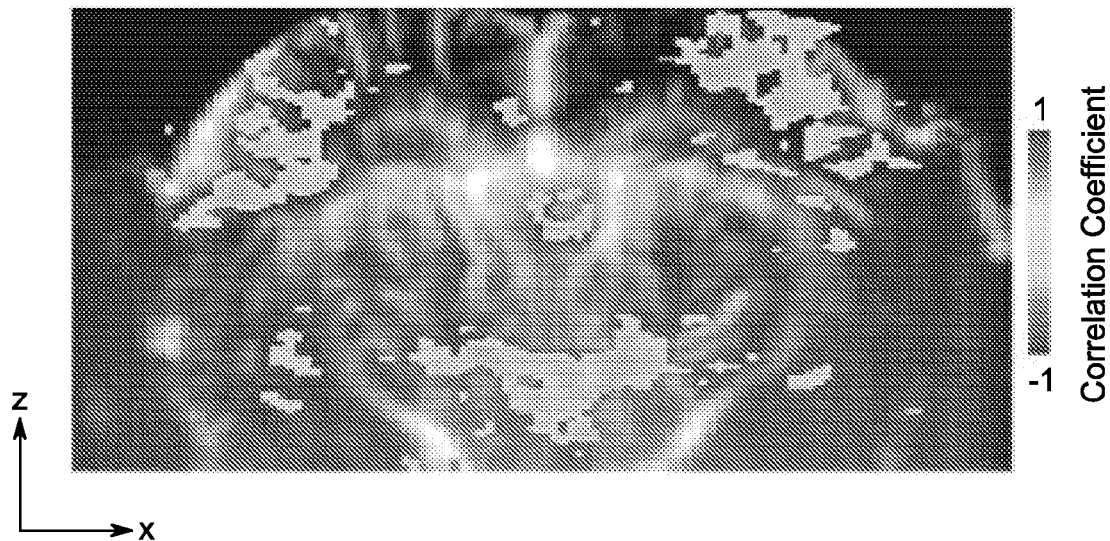
Average Evoked Amplitude
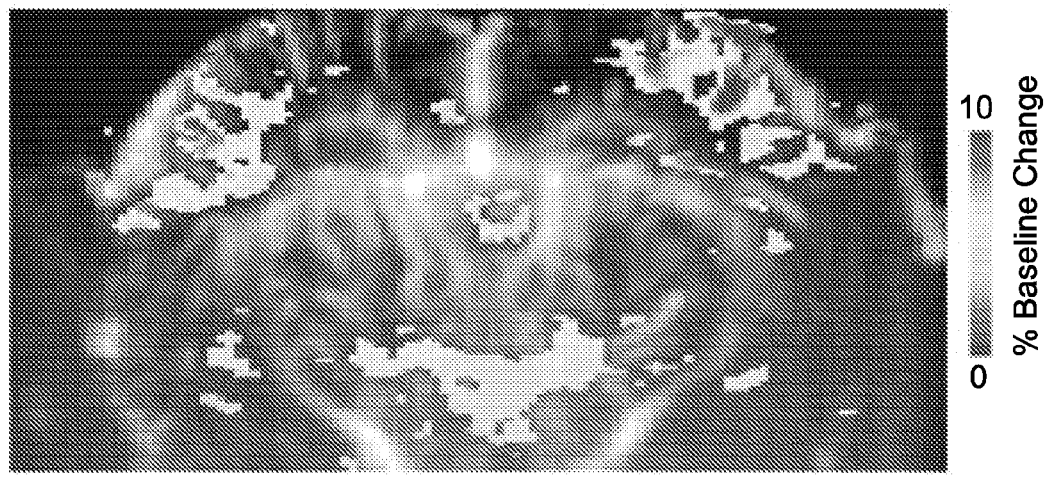
FIG. 2A

FIG. 4

Tentonin-3 (TTN3; TMEM150C)
249 amino acids

MDGKKCSVWMFLPLVFTLFTSAGLWIVYFIAVEDDKILPLNSAERKPGVKHAPYISIAGDDPPASCVFSQVMNMAAFLALVVAVLRFIQLKPKVLNPW
LNISGLVALCLASFGMTLLGNFQLTNDEEIHNVGTSLTFGFGTLTCWIQAALTLKVNIKNEGRRVGIPRVILSASITLCVVLYFILMAQSIHMYAARV
QWGLVMCFLSYFGTFAVEFRHYRYEIVCSEYQENFLSFSESLSEASEYQTDQV (SEQ ID NO: 1)

FIG. 5A
Piezo-1
2520 amino acids

```
   1  mephvlgavl ywlllpcall aacllrfsgl slvyllflll lpwfpgptrc glqghtgrll
  61  rallglsllf lvahlalqic lhivpridql lgpscsrwet lsrhigvtrl dlkdipnair
 121  lvapdlgilv vssvclgicg rlarntrqsp hprelddder dvdasptagl qeaatlaptr
 181  rsrlaarfrv tahwllvaag rvlavtllal agiahpsals svylllflal ctwwachfpi
 241  strgfsrlcv avgcfgaghl iclycyqmpl aqallppagi warvlglkdf vgptncssph
 301  alvlntgldw pvyaspgvll llcyataslr klrayrpsgq rkeaakgyea relelaeldq
 361  wpqeresdqh vvptapdtea dncivheltg qssvlrrpvr pkraepreas plhslghlim
 421  dqsyvcalia mmvwsityhs wltfvlllwa cliwtvrsrh qlamlcspci llygmtlccl
 481  ryvwamdlrp elpttlgpvs lrqlglehtr ypcldlgaml lytltfwlll rqfvkekllk
 541  waespaalte vtvadteptr tqtllqslge lvkgvyakyw iyvcagmfiv vsfagrlvvy
 601  kivymflfll cltlfqvyys lwrklikafw wlvvaytmlv liavytfqfq dfpaywrnlt
 661  gftdeqlgdl gleqfsvsel fssilvpgff llacilqlhy fhrpfmqltd mehvslpgtr
 721  lprwahrqda vsgtpllree qqehqqqqe rvqvflrrll elhvfklval ytvwvalkev svmnlllvvl
 781  wglvaerlle laagfsdvls rvqvflrrll elhvfklval ytvwvalkev svmnlllvvl
 841  wafalpyprf rpmasclstv wtcviivckm lyqlkvvnpq eyssnctepf pnstnllpte
 901  isqsllyrgp vdpanwfgvr kgfpnlgyiq nhlqvllllv feaivyrrqe hyrrqhqlap
 961  lpaqavfasg trqqldqdll gclkyfinff fykfgleicf lmavnvigqr mnflvtlhgc
1021  wlvailtrrh rqaiarlwpn yclflalfll yqyllclgmp palcidypwr wsravpmnsa
1081  likwlylpdf frapnstnli sdfllllcas qqwqvfsaer teewqrmagv ntdrleplrg
1141  epnpvpnfih crsyldmlkv avfrylfwlv lvvvfvtgat risifglgyl lacfyllfg
1201  tallqrdtra rlvlwdclil ynvtviiskn mlsllacvfv eqmqtgfcwv iqlfslvctv
1261  kgyydpkemm drdqdcllpv eeagiiwdsv cfflllqrr vflshyylhv radlqatall
1321  asrgfalyna anlksidfhr rieekslagl krqmerirak qekhrqgrvd rsrpqdtlgp
1381  kdpglepgpd spggsspprr qwwrpwldha tvihsgdyfl fesdseeeee avpedprpsa
1441  qsafqlayqa wtnaqavlr rrqqeqeqar qeqagqlptg ggpsqevepa egpeeaaagr
1501  shvvqrvlst aqflwmlgqa lvdeltrwlq eftrhhgtms dvlraeryll tqellqggev
1561  hrgvldqlyt sqaeatlpgp teapnapstv ssglgaeepl ssmtddmgsp lstgyhtrsg
1621  seeavtdpge reagaslyqg lmrtaselll drrlripele eaelfaeggg ralrllravy
```

FIG. 5B

```
1681  qcvaahsell  cyfiiilnhm  vtasagslvl  pvlvflwaml  siprpskrfw  mtaivfteia
1741  vvvkylfqfg  ffpwnshvvl  rryenkpyfp  prilglektd  gyikydlvql  malffhrsql
1801  lcyglwdhee  dspskehdks  geeeqgaeeg  pgvpaatted  hiqvearvgp  tdgtpepqve
1861  lrprdtrris  lrfrrrkkeg  parkgaaaie  aedreeeege  eekeaptgre  krpsrsggrv
1921  raagrrlqgf  clslaqgtyr  plrrffhdil  htkyraatdv  yalmfladvv  dfiiiifgfw
1981  afgkhsaatd  itsslsddqv  peaflvmlli  qfstmvvdra  lylrktvlgk  lafqvalvla
2041  ihlwmffilp  avtermfnqn  vvaqlwyfvk  ciyfalsayq  ircgyptril  gnfltkkynh
2101  lnlflfqgfr  lvpflvelra  vmdwvwtdtt  lslsswmcve  diyanifiik  csretekkyp
2161  qpkgqkkkki  vkygmgglii  lfliaiiwfp  llfmslvrsv  vgvvnqpidv  tvtlklggye
2221  plftmsaqqp  siipftaqay  eelsrqfdpq  plamqfisqy  spedivtaqi  egssgalwri
2281  sppsraqmkr  elyngtadit  lrftwnfqrd  lakggtveya  nekhmlalap  nstarrqlas
2341  llegtsdqsv  vipnlfpkyi  rapngpeanp  vkqlqpneea  dylgvriqlr  reqgagatgf
2401  lewwvielqe  crtdcnllpm  vifsdkvspp  slgflagygi  mglyvsivlv  igkfvrgffs
2461  eishsimfee  lpcvdrilkl  cqdiflvret  releleeely  akliflyrsp  etmikwtrek
2521  e
```

(SEQ ID NO: 2)

FIG. 6

OSCA1.2
Ca$^{2+}$ permeable channel (*Oryza sativa*)

```
  1 matvsdigls aainvsmava fllvfaflrl qpindrvyfp kwylrgmrds pvssgaavqk
 61 vvnlnmrsyl kflswmpaal kmpedelinh agldsavylr iyltgikifv pisilaslvl
121 fpvnwtndtl dsmkvvhski dklsisnipy gsnrfvthlv mayavtfwtc yvlfreyeii
181 ttmrlrflas ekrrpdqftv lvrnippdpd esiselvehf flvnhpdhyl rhqvvynank
241 ladlvekkkk lqnwldyyql kyernpskrp ttktgflgcf gsevdaieyy kaeiekigke
301 eaderqkimk dpqsavpaaf vsfrsrwgaa vcaqtqqtsn ptvwitewap eprdvywnnl
361 sipfvsltvr rlivavaff lnffyvipia fvqslasleg iekalpflkp likidviksf
421 iqgflpgial kvflillpti lmfmskfegl isqsslerrs askyyiflff nvflgsivtg
481 saldqlkayi hqsaneiprt igvaipmrat ffityvmvdg wtgvageilr lraliifhlk
541 nfflvktekd reeamdpgsi cfdwceepriq lyfllglvya vvtplllpfi lvffglayvv
601 yrhqiinvyn qqyesgaqfw psvhgriiia livsqlllig llstkgfeet tpvlvvlpvl
661 tfwfykyckn rfepafvrnp lqeamrkdtl erareptfdl kaylanaylh pvfkgreeed
721 nmsisedvgm eeivvptkrq srrntpaqsk yegsdtlslp etvher
```

(SEQ ID NO: 3)

FIG. 7

TREK-1
(potassium channel; 411 amino acids)

```
  1 maapdlldpk saaqnskprl sfstkptvla srvesdttin vmkwktvsti flvvvlylii
 61 gatvfkaleq pheisqrlli viqkqtfisq hscvnsteld eliqqivaai nagiiplgnt
121 snqishwdlg ssfffagtvi ttigfgnisp rteggkifci iyallgiplf gfllagvgdq
181 lgtifgkgia kvedtfikwn vsqtkiriis tiifilfgcv lfvalpaiif khiegwsald
241 aiyfvvitlt tigfgdyvag gsdieyldfy kpvvwfwilv glayfaavls migdwlrvis
301 kktkeevgef rahaaewtan vtaefketrr rlsveiydkf qratsikrkl saelagnhnq
361 eltpcrrtls vnhltserdv lppllktesi ylngltphca geeiavienl k
```

(SEQ ID NO: 4)

FIG. 8A piezo 2
(2752 amino acids)

```
   1 masevvcgli frlllpicla vacafryngl sfvylylyll iplfseptkt tmqghtgrll
  61 kslcfislsf llhiifhit lvsleaqhri apgyncstwe ktfrqigfes lkgadagngi
 121 rvfvpdigmf iasltiwllc rnivqkpvtd eaaqsnpefe neelaegeki dseealiyee
 181 dfnggdgveg eleestklkm frrlasvask lkefignmit tagkvvvtil lgssgmmlps
 241 ltssvyffvf lglctwwswc rtfdpllfsc lcvllaifta ghliglylyq fqffqeavpp
 301 ndyyarlfgi ksviqtdcss twkiivnpdl swyhhanpil livmyytlat liriwlqepl
 361 vqdegtkeed kalacspiqi tagrrslwy athyptderk llsmtqddyk psdgllvtvn
 421 gnpvdyhtih pslpmengpg kadlystpqy rwepsdesse kreeeeeeke efeeersree
 481 krsikvhamv svfqfimkqs yicaliamma wsityhswlt fvlliwsctl wmiirnrrkya
 541 misspfmvvy gnlililqyi wsfelpeikk vpgflekkep gelaskilft itfwlllrqh
 601 lleqkalqek eallsevkig sqeneekdee lqdiqvegep keeeeeeake ekqerkkveq
 661 eaaeeedeqd imkvlgnlvv amfikywiyv cggmfffvsf egkivmykii ymvlflfcva
 721 lyqvhyewwr kilkyfwmsv viytmlvlif iytyqfenfp glwqnmtglk kekledlglk
 781 qftvaelftr ifiptsfllv cihlhyfhd rfleltdlks ipskedntiy rlahpegslp
 841 dltmmhltas lekpevrkla epgeeklegy sekaqkgdlq kdseeseedg eeeeeseeee
 901 etsdlrnkwh lvidritvlf lkfleyfhkl qvfmwwilel hiikivssyi iwvsvkevsl
 961 fnyvfliswa falpyaklrr lassvctvwt cviivckmly qlqtikpenf svncslpnen
1021 qtnipfneln ksllysapid ptewvglrks spllvylrnn llmlailafe vtiyrhgeyy
1081 rgrnnltapv srtifhditr lhlddglinc akyfinyffy kfgletcflm svnviggrmd
1141 fyamihacwl iavlyrrrrk aiaeiwpkyc cflaciitfq yficigippa pcrdypwrfk
1201 gasfndniik wlyfpdfivr pnpvflvydf mllicaslqr qifedenkaa vrimagdnve
1261 icmnldaasf sqhnpvpdfi hcrsyldmsk viifsylfwf vltiifitgt trisifcmgy
1321 lvacfyflf ggdlllkpik silrywdwli aynifvitmk nilsigacgy igtlvhnscw
1381 ligafslact vkgyqmpaan spctlpsgea gliwdsicfa flllqrrvfm syyflhvvad
1441 ikasqilasr gaelfqativ kavkarieee kksmdqlkrq mdrikargqk ykkgkermls
1501 ltqepgeggd mqklseedde readkqkakg kkkqwwrpwv dhasmvrsgd yylfetdsee
1561 eeeeelkked eepprrsafq fvyqawitdp ktalrqrhke kkrsareerk rrrkgskegp
1621 vewedredep ikkksdgpdn ikrifnilk ftwvlflatv dsfttwlnsi srehidistv
1681 lriercmltr eikkgnvptr esihmyyqnh imnlsresgl dtidehpgaa sgaqtahrmd
1741 sldshdsiss eptqctmlys rqgttetiee veaeqeeeag stapepreak eyeatgydvg
1801 amgaeeaslt peeeltqfst ldgdveapps yskavsfehl sfgsqddsag knrmavspdd
```

FIG. 8B

```
1861  srtdklgssi lpplthelta sellkkmfh ddeleesekf yvgqprfll fyamyntlva
1921  rsemvcyfvi ilnhmvsasm itlllpilif lwamlsvprp srrfwmmaiv ytevaivvky
1981  ffqfgffpwn knvevnkdkp yhppniigve kkegyvlydl iqllalffhr silkchglwd
2041  eddmtesgma reesddelsl ghgrrdssds lksinlaasv esvhvtfpeq qtavrrkrsg
2101  sssepsqrgs fssnrsqrgs tstrnssqkg ssvlsikqkg krelymeklq ehlikakaft
2161  ikktleiyvp ikqffynlih peysavtdvy vlmfladtvd fiiivfgfwa fgkhsaaadi
2221  tsslsedqvp gpflvmvliq ylrktvlgkv ifqvilvfgi hfwmffilpg
2281  vterkfsqnl vaqlwyfvkc vyfglsayqi rcgyptrvlg nfltksynyv nlflfqgfrl
2341  vpfltelrav mdwvwtdttl slsswicved iyahifilkc wresekrypq prgqkkkkvv
2401  kygmgqmiiv lliicivwfpl lfmsliksva gvinqpldvs vtitlggyqp iftmsaqqsq
2461  lkimdqqsfn kfiqafsrdt gamqflenye keditvaele gnsnslwtis ppskqkmihe
2521  lldpnssfsv vfswsiqrnl slgakseiat dklsfplkni trkniakmia gnstessktp
2581  vtiekiypyy vkapsdsnsk pikqlisenn fmditiilsr dnttkynsew wvlnltgnri
2641  ynpnsqalel vvfndkvspp slgflagygi mglyasvvlv igkfvreffs gishsimfee
2701  lpnvdrilkl ctdiflvret geleleedly akliflyrsp etmikwtrek tn
```

(SEQ ID NO: 5)

FIG. 9

TRAAK
(potassium channel; 393 amino acids)

```
  1 mrsttllall alvllylvsg alvfraleqp heqqaqrelg evrekflrah pcvsdqelgl
 61 likevadalg ggadpetnst snsshsawdl gsaffsgti ittigygnva lrtdagrlfc
121 ifyalvgipl fgillagvgd rlgsslrhgi ghieaiflkw hvppelvrvl samlflligc
181 llfvltptfv fcymedwskl eaiyfvivtl ttvgfgdyva gadprqdspa yqplvwfwil
241 lglayfasvl ttignwlrvv srrtraemgg ltaqaaswtg tvtarvtqra gpaappeke
301 qplppppcp aqplgrprsp sppekaqpps pptasaldyp senlafides sdtqsergcp
361 lpraprgrrr pnpprkpvrp rpgrprdkg vpv
```

(SEQ ID NO: 6)

FIG. 10

TRPV4
(764 amino acids)

```
  1 madssegpra gpgevaelpg desgtpggea fplsslanlf egedgslsps padasrpagp
 61 gdgrpnlrmk fqgafrkgvp npidllestl yessvvpgpk kapmdslfdy gtyrhhssdn
121 krwrkkiiek qpqspkapap qpppilkvfn rpilfdivsr gstadldgll pflithkkrl
181 tdeefrepst gktclpkall nlsngrndti pvldiaert gnmrefinsp frdiyyrgel
241 plslaactng phivnylten phkkadmrrq dsrgntvlha lvaiadntre ntkfvtkmyd
301 lllkcarlf pdsnleavln ndglsplmma aktgkignrh emlavepine llrdkwrkfg
361 avsfyinvvs ylcamviftl tayyqplegt ppypyrttvd ylrlagevit lftgvlffft
421 nikdlfmkkc pgvnslfidg sfqllyfiys vlvivsaaly lagieaylav mvfalvlgwm
481 nalyftrglk ltgtysimiq kilfkdlfrf llvylifmig yasalvslln pcanmkvcne
541 dqtnctvpty pscrdsetfs tflidlfklt igmgdlemls stkypvvfii llvtyiiltf
601 vlinmlial mgelvgqvsk eskhiwklqw atlidiers fpvflrkafr sgemvlvqks
661 sdgtpdrrwc frvdevnwsh wnqnlgiine dpgknetyqy ygfshtvgrl rrdrwssvvp
721 rvvelnknsn pdevvvplds mgnprcdghq qgyprkwrtd dapl
```

(SEQ ID NO: 7)

FIG. 11

P2X7
(595 amino acids)

```
  1 mpaccscsdv fqyetnkvtr iqsmnygtlk wffhviifsy vcfalvsdkl yqrkepviss
 61 vhtkvkgiae vkeeivengv kklvhsvfdt adytfplqgn sffvmtnflk tegqeqrlcp
121 eyptrrtlcs sdrgckkgwm dpqskgiqtg rcvvhegnqk tcevsawcpi eaveeaprpa
181 llnsaenftv liknnidfpg hnyttrnilp ginitctfhk tqnpqcpifr lgdifretgd
241 nfsdvaiqgg imgielywdc nldrwfhhcr pkysfrrldd kttnvslypg ynfryakyyk
301 ennvekrtli kvfgirfdil vfgtggkfdi iqlvvyigst lsyfglatvf idflidtyss
361 nccrshiypw ckccqpcvvn eyyyrkkces ivepkptlky vsfvdeshir mvnqqligrs
421 lqdvkgqevp rpamdftdls riplalhdtp pipgqpeeiq llrkeatprs rdspvwcqcg
481 rclpsqipes hrcleelccr kkpgacitts elfrklvlsr hviqflllyq eplaldvds
541 tnsrlrhcay rcyatwrfgs qdmadfailp sccrwrirke fpkseggysg fkspy
```

(SEQ ID NO: 8)

FIG. 12

MscL
(142 amino acids)

```
  1 mlnefkefia rgnvmdlavg viigaafski vdsvvndlvm pvvgaitggg fdfsnyflpl
 61 sasvtaptls aareggavfa ygnfitvlin flilawiifl liklvnrara sverdkapdp
121 aapppqdill lseirdllrq ra
```

(SEQ ID NO: 9)

FIG. 13A

OSCA1.2 atggctaccctgcaagatatcggcgtgagcgctggaatcaacatcctccgcctttgtgttcttcatcatcttcgctgttgctgagactgcagccctttaacgacagggtctacttcagcaagt
ggtacctgaagggactcaggtccagccctgctagggggaggagccttcgctcagagattcgtgaacctgactcaggagctcagatgaagttcctgaactgcctggagctctcaaa
atgcccgagccgagctgattgatcacgccggcctggatagcgtcgtctatctgaggatctactggctcggcctgaagatctttacacctatgccgtgctgctggcgtcctggtgc
ccgtgaattggaccaacaacactggagatggccaaacagctgaggaatgtgacctcctcgacatcgacaaactgagcgtctccaacatcccgagtatagcatgaggttctggacc
cacatcgtcatggcctacgcccttaccatctgacctgctacgtcctgatgaaggagtacgagaccatgccaacatgaggctgcagttcgtggccagcgaagctagaaggcccgacca
gtttaccgtgctgtggtgaggaacgtgccccctgacgctgagcgagctcgtcgagcattcttcctggtgaaccatcctgaccactacctgaccaccaagtgtgtgcaa
cgccaacaaactgccgacctgtcaaaaaaaaagaagctccagaactgctggactactgccagagctccaagtacgccaggaacaatagccagagattgtcaagctcggcttt
ctgggcctctggggccagaaggtcgatgccattgagcactacatcgccgagattgacaaatctccaaggagatctccaagagagaggaggaagtggtgaacgaccccaaagccatc
atgcctgccgccctcgtgagcttaagaccaggtgggctgccgccgtgtgcgctcagaaccaacagaaccccaccccagtggctcaccgaatgggctcctgaaccaggg ac
gtgttctgtccaatcggccatcccctatgtgagcctgaccgtgaggaggctgattatgcacgtggccttcttcttcctgaccttttctttatcgtccctatcgctcgtcagtcctggcta
ccatcgaaggaattgtcaaagccgccccccttcctcaagttcatgaagagcgtgatcaagttctccctggcattgctctgaagcgtgttcctggcttctccc
ctccatcctgatgatcatgagcagttcgagggcttcactccatctccagcttagaaaggaggggccgccttcagataactatattttaacctgtgaatgtcttctggcctccgtgattgctg
gagccgcttcgagcagcagtcaacagttcctcaacagtccgctaaccagattcctaagaccatcgcgtggctatcccatgaaagccacattcttatcacatacattatggtggacgg
atgggccggcgtggctggagaactggagagcctctgattatgttctcatctgaagacagaaggataggggggaggccatgaccgactcggttctattg
gctttaacacaggcgagccaggattcagctgtactcctgggactgtctacgccccctgacaccatgctgctgccttatcctcgtgttctgctcggcctacattgtctacag
gccagatcatcaacgtgtacaatcaggagtacgaatcgccgtccttctgccgacgtgcatgccagcagagtgattgctgcctggtgatcagcaggactgct

FIG. 13B cggaaccaagcatgccgctctggccgccccctttctgattgctctgcccgtcctgaccatcggctttcaccattctgcaaggcaggtacgagcctgctttcatcaggtaccccctgcagg
aagccatgatgaaggacaccttagaaacagccagagcctaacctcaaggctacgtgcaccgtgttcaaggcgacgaggatgactatgacat
cgatgacaaactggggcaagtttgaggacgaggctatcatcgtcccccaccaaaaggcaatccaggagaaacaccccctgccccagcattatctccggcgatagtagccctagcctgccc
ttttccggcaagctcgtg
(SEQ ID NO: 10)

FIG. 14 hTMEM150C atggatgggaagaaatgcagcgtatgatgttcctacctctctgtatttacttgtttacttcagctggattgtggatagtatacttcatagctgtgtggaagatgacaaaattttaccattaaattcagc
tgaaaggaaacctggtgtgaagcatgcaccatatataagcattgcaggtgatgatcctcctgcaagctgtgtgtttagtcaagttatgaacatggcagccttcctagccctgtggtagctgtt
ctgcgcttcataacaactgaaaccgaaggtttaaaccgctggctaatattagtgattggtggctctgtgtctgcttccttcggaatgaccttacttgtaattttcagctcacaaatgatgaa
gaaatccataacgtcggaacttccttgacctttggcacattgacctgctgcgctgcacctcaaggtcaacatcaagaatgaaggacggagagttggaattccac
gggttattctgtcggcatcactctctgtgtggtcctctacttcatcctcatgtgcccaaagcatcacacatgtgcagccaggtccagtggggcctggtcatgtgcttcctgtcttattttg
gcacctttgccgtggagttccggcattaccgctatgagattgttttgctctgagtaccaggagagaattttcctaagcttctcagaaagcctgtcagaagcttctgaatatcagactgaccaggtg (SEQ ID NO: 11)

FIG. 15A

Piezo-1 atggagccgcacgtgctggggccgggctctactggctgtgctgcgctcctgttacgcttcaatgctctcgctgtcactgtttctactgctgc
cctggcttccaggccctcaagacacagcattaccagttcacacagtgcctgctccgtgcactactctgctctcagcctcctcttcctgttggccccacctgcctttcagatatgcctacac
accgtgcctcacctgaccagttctgggacaaaacgtagcctttgggtgaaggtgtcaacacataggggttacgaggctgaactgaaggacatctttaacaccaccaggctgta
gcacctgacctgggagtgctgctggcgtgctcccttgcctggacgcctcacgaggaaagccgggcagagtcggcaccaggagctgcaggatgcaggatgacgatgac
gatgatgacgacgatgaagagacatagatgctgcccagccgtggggagccctgcctggcaaccaaacgcaggctgtggctgcctcccgcttccgggtcacggccca
ctggctgctgatgacctctggacggacgctggtcattgttgctggcctggtctttggctgctacccctccagcatcaccctggtgttcctggccatctgcacctggt
ggtcctgtcactttcctcagccccctggagctattgtgtcatgtgagctgtttttggtgccggccatcatcattgcctatactgtcatcagacaccattatccaggacatgttacc
ccctgggaacatctgggccaggctatttggtctcaagaacttcgtagacctcctaactcccagcccctgaaagctccctcagagtgtccctcagagctcctgaaactgagagctgagctgagagctgagctgagtccc
ggaatcctgctgctgtatattacacagcccaccctctctgaagctccacaagagctgtccctcagagtcctcagaagctgagagctgagatgaggagcatgagctgaactgg
accacctggacccgagccagcccagggagcgtaggacgccaccagggtgagatgccatgacccgctacatgcctgatcaccgtgacaactgacctgacactgacaagccagagccagagcctgtc
cgccagcgtccagttcgcccgcccagcttgggcctgctgagcctgaaagagagatgtcaccgtcacgcctacatgcctgggccgctcaagccatcatggacccagagctgtgtgtgctgattgccatgatggtgtg
gagcatcatgtaccacagttggccacaggtatgtgtgggccatgagcggtggcctgcctacctgctggcctgctcatctgctgctgctgatgggc
tgacgtctgctgagttgggtctacatggaacttcctgacctgcctgagctgcccacccctgggatctgcaccagtggactgggatcagcatcagccaagtgccgctgcgctacctgcgctacccttgcctggacc
tcggtgccatgctcctcatctgctcacattcgtcctttgcgtcagttcgtagttcgtgaaggaaggcagcatctacgtcaaatactgatctgtgaggaagctgctactgtgtgccgccatgttcattggtcagcttcgccggc
ctgagcccacacagacccagacgctgctgcggagcctgcgggagcctggggtcagctggccatctacggtcctactacaccctgttccagtgttccaggactccaaactccacctcccaccctattgcgcaacctcacgggcttcacagacgagagcagttgggcgacctggcgacggctgagcagttcagtgtg
cgcctggtctaccaaatcgtctacaaaatcgtctactacttcctgctcagatcctcagttccagtctcactgcacctgtcctgctcactacaccctgttccaggtcctactaccactccacagaccgtgcactacttccacagacctcacgggcttcacagacgagagcagttgggcgacctggcgacggctgagcagttcagtgtg
aatgctcgtcatcgctgtgtacacctccagttccagtccagtccagtccagttccagtcccactattggcgcaacctcccaccctattggcgcaacctccccctattggcgcaacctcccaccctattggcgcaacctcacgggcttcacagacgagagcagttgggcgacctggcgacggctgagcagttcagtgtg
tcggagctcttttccagtatcctcatcctcatcctcatcctcatcctcatcctcatcctcatcctcatcctcatcctcatcctcatcctcatcctcggtcttccagtatcctcatcctcatcctcatcctcatcctcatcctcatcctcatcctcatcctcatcctcatcctcatcctcatcctcatcctcatcctcatcctcatcctcatcctcatcatcatgcagctcatgaccggagcacgtgccgcaccaggc

FIG. 15B acccgccacctgcgatgggctcacaggcaggatgcagtgagcgaggcccctcgcttgagcatcaggaggaagaggaagtcttcagggaagatgggcagagcatggatgggcccc
accaggccacacagtccctgagggtacggccagcaagtggggcctggtgctgaccggctgctgccagctaccggccagcttctcgctcctccaccaggtgttcgttcg
gcgcttgctagaacttcacgtcttcaagctgtgtggccctctacactgtctgggtggccctgaagaagtgtctgtgatgaacctgctgctggtgctatgggccttgccctatcc
gcggcttccggccgccatggcttcctgcctgtccaccgtgtgaccctgtatcatcattgtatgcaagatgctctatcagctcaagattgtcaacccgcatgagtactcagcaactgcactgagcc
cttcccaacaataccagccttgggagatcaacagtctttgctgtaccgtggccctgttgacctgccaactgtttggggtgcggaagggttacccaacttgggctatatcca
gaaccacctgcgagatccttcgttgcttgtgtttgaggccgtggtgtaccggcgccaagagcacaaccgcccggcagcaccagcagccccctcgccccgccaggctgtgcgagat
ggcaccccgccagaggttggaccagaacctagctgcctcaagtattcatcaacttcttctacaaattcggctggagatcgtcttcttgatgccgtgaatgtgattgggcacgcgt
atgaacttcatgtgatcttacacgttgctggttggtggccatcctacacgcgcggccatcgcccgctctgccaactacttctgtttcctcacgcgtgtctgctgtacc
agtacctgctgtgtttgggcatgccccctgcactgcattgactatcattgactatcatcgatgtgctacctgactttcttcagag
ccccaactccaccaacctatcagtgacttcctcctgctttgcgcctccaacttcatcactgagcgagcgaacgagagtggccgtcttccgctaccttgtctggctgctgctcgttgt
gaccacctgagccctgcgtggggagccaccccgcataagcatcttcgggctgtgggtacctgctagccctgctgctttggcactacctgagaaggacacgcgagcccagctcgt
ggtgtttgttgcgggggccaccgccctgcctcctctataatgtcactgtcatcatctaagaatatgctgtgctcctgtgtcttcgtgagcaactctgctggtcatccagctctca
gctgtgggactgctcctcatctccaaagagatgatgaccaggagccctgcctgtgaggaggccggatcatctgggactgtcatcttgttcttcttcc
gcctcgtgtcacagtcaaggctactatgatccaaagagatgatgaccaggagccctgcctgtgaggaggccggatcatctgggacagtatctgcttcttcttcc
tgctcttgcaacggcgcatctttctcagccactcctgcatgtcagcgctgacctgcaggccctgaaaagccacagcctgacctgcaggcatccaggggctttgccctctacaatgcagccaacctgaagag
catcaacttccatcgccagattgaggagaagaagtccctgccagctgaaaaagacaggcgaagcatcgtgccaacaggagaagcaggaagtacaggaagcaggcaagtcgtggccaac
tccagtccaaagacccctcaggatccagcagcctgacagcccaggggagcccaggggcctctcccccgccacggagacagtggtggccgccctggctgaccacgccacagtcat

FIG. 15C ccactctggcgactacttcctgtttgagtcagatagcgaggaggaggaagaggaggcccctacctgaggacccaggcctcagctcagagtgcctccagatgcatccagagtcatgggta
accaatgcccagacagtgctgaggcagcgtcgggagcgggcacggcaggacgggcagagcagcgtggcttctggagtgacttgaaccagatgtgaaccagtagatgtcccag
aagatgagatgcaggccgtagccacatgatgcagcgtgtgctaagcaccatgcagtcctgtgggccaggccacgtagacgggctgacgcgctggctgcgtgcattca
cgaagcaccaccgcaccatgagcgatgtgctgtgcgcagagcgctacctgctcaccagagctcttcgggttggagaggtacgcccgagtgtgctgaccagctttatgtgggtga
agatgaggccacattgtcaggtcccgtggagacccggatggaccgagagattgtcaccgacgtggcagtggcagtgaggagagtcccaagagcttttagccaatgctcgtaccc
ctgagcacagcctataaacaccccgcagtggcagtgaggagattgtcaccgacgcgtggggactcccaggctccaagagcttttagccaatgctcgtaccc
ggatgcgcacggccagcgagctgctactggatataggcgcctgcatatcctgagctgagagggccgagcgtttgaggcacagcaggccgactctgcggctgctcagggctgg
gtaccagtgcgtggcggcacactcggagctgctctgttacttcatcatcatcctttaaccacatgtgacagcctccggctgcctccctgctgccgtgcttgttcctgtgggccatgct
gaccatcccgaggcctagcaagcgctttggatgacagctatcgtctcactgagtctcaggtcataccttggtcaccaaataccttcagttcgtctcttccctgaacagctacgttgctgcg
gcgctatgagaacaagcctactccctccggagctgagagcctccccgcgaatctggccttgagaaaacgacagctacatcaagtatgaccttggctgcagctccaccgctcagctactg
tgttatggcctctgggaccatgaggagatcgctatcccaaggaccattgcaggagtagtgtgaaggaccgggaggccaaggaagagccaagactaagctgaatcgcagtctgag
acaggcactgggccatcccaaggagcacgtgtggccggtgtgtgggccggtactccaggacccaagggtgtgtgggccggtactccaggacccaagggaaggaagtattagatccaaggatgtattccaagatccccagagagaccttaag
ccccggcacacgaggcacacatcagcacgcttcaggaggccaaggagccaaggagaatccaaggagaccaggagccaagaaccagcagtcatgagagccgagcacgaggagggagaaagaaac
tacagagagaaagagggccgtcacactcaagaaaaatcgaagtttcgggagagaatgaaggcagctgggcgccggctgcagagctttctgtgtcactgcccagagcttctacca
accccttgcagcgttttcttccatgacattctgcacacaaagtaccggcggccaccgacgtcacgccctcatgttcctgccgatattgtcgacatcatcatcttggttttttgggcttt
tggaagcactctgcagccacacactgcatcctgtcagatgaccagttgccacagccttcctgttcatgctgctgttcagttggccacatgtcaccgtcatcgaccgtgccctctac
ctgcgcaagactgtcctgggaaagctggcctttcaggtggtcctggtggtggccgattcaactctgatgttctttatcttaccggctgtcactgagagaggatgttcagcagaatgcggtggc

FIG. 15D acagctgtggtacttcgtcaagtgcatttacttgccctgtccgcctaccagatccgctgtggctaccccaccgtatcttgggcaacttcctcaccaagaaatacaaccatctaaacctcttc
cttccaggggttccgtctagtgccgttcctggagctgccggggccgtcatggactgggtgtggaccgacaccacgctgtcctgtcaactggatgtgtggaagacatctatgcca
acatctttatcatcaagtgcagccgagagacagagaagaagaaataccccagccaagggcagaagaaggcagaagaaaattgtcaagtatgtggaggcctcattatcctcctcatcg
ccatcatctggttccctctgctcttcatgtcactgatccgctctgtggtcgggtcgtcaacagccagcccattgatgtcaccctcaagctaggcggctatgagccactgttcaccatga
gcgccagcagccatccattgtgccattcacaccccaggcctacgaggagctgtccagccatgcagtttgaccctatccactagccatgcagttcattagccagtcctgaggacatcg
tcactgcacagatcgaggggcagctcgggtgtgggccatcagccaccagccagatgaagcaggagctgtacaacgcacagccgacattacactgcgctttacc
tggaatttccaaaggggacctggccaaggggtggcactgtggagtatactaatgagaagcacacctggagctggcccccaacagtacggcacgaaggcagctggccaactgctcgag
ggcagacctgaccagtcagtgcattcccatctcttcccccaagtacattcgtgctccaatggcctgaagcaacctgtgaagcagctgcagccagatgaggaagagagactaccttt
gtgtgccatccagctgccgagggagcaagtgggcacaggggcctctggggagcaagcgggcaccaaggcctccgacttcctcgagtgtgggtcatcgagctgcaggactgca
aggctgactgcaacctgctgccatggctcatcttcagtgacaaggtcagccaccctagccctgggcttcctggccggctacggggattgtggggctgtacgtcctccatcgtcgtggttgg
caagtttgtgcggggcttcttcagcgagtgcttcactccatcatgttcgaggaactgccgtgtgtggaccgcatcctcaagctgccaggaccatcttcttggtgcgcgagacccgggag
ctggagctggaggaggagctatacgccaagctcatcttcctgtaccgatctccagagaccatgattaagtggacacgtgagaggggag (SEQ ID NO: 12)

SYSTEMS AND METHODS FOR MECHANOGENETIC FUNCTIONAL ULTRASOUND IMAGING

CROSS-REFERENCE

This application claims the benefit of U.S. Provisional Patent Application No. 62/887,163, filed Aug. 15, 2019, which application is incorporated herein by reference in its entirety.

INTRODUCTION

Functional studies of neuronal tissues involve stimulating one or more neurons with a defined stimulus and measuring the output response of the one or more neurons. Current methods of stimulating neurons and measuring the output response include optogenetics, functional magnetic resonance imaging (fMRI), electrophysiology, electroencephalography (EEG) and behavioral monitoring.

SUMMARY

The present disclosure provides a system for functional ultrasound imaging, where the system comprises: a) an apparatus for delivering a nucleic acid encoding a mechanosensitive ion channel to a target neural cell population in a region of a brain; and b) a functional ultrasound imaging device. The present disclosure provides a method for functional ultrasound imaging.

BRIEF DESCRIPTION OF THE DRAWINGS

FIGS. 2A-2C depict functional ultrasound imaging. FIG. 2A Brain activation was measured by ultrafast ultrasound imaging during right hindlimb electrical stimulation in mice. (top) A 15 MHz ultrasound probe was positioned over the mouse brain in a coronal orientation at 2.06 mm behind bregma while 10 µA of electrical stimulation was applied to the right hindlimb at 5 Hz. (middle) Activation map displaying the Pearson correlation coefficient for significantly correlated pixels. Significance was determined as values greater than three times the spatial standard deviation, corresponding to $p<0.001$ (uncorrected). (bottom) Amplitude map for significantly active pixels was determined by the average % change from baseline during each of the stimulation blocks. FIG. 2B: Power doppler time series of the significantly active pixels in the left primary sensory cortex (S1) during electrical stimulation (top) and no stimulation (bottom). Blue blocks indicate stimulation blocks (if applied). FIG. 2C: (top row) Power spectrum of compound doppler images for pixels exhibiting positive (left) and negative (right) doppler shifts, corresponding to blood moving towards and away from the ultrasound transducer, respectively. (bottom) Axial blood flow map displaying the velocity of blood in various arterioles and venules.

FIG. 3A State-of-the-art functional ultrasound imaging technology with single-plane, head-fixed imaging capability: Biological tissue was insonified with plane waves at multiple tilt angles. The backscattered echoes were beamformed to generate low quality ultrasound images, which were then coherently summed together to generate a single compound ultrasound image. 200 of such compound images were collected at a frame rate of 500 Hz (400 ms) to capture the time-varying hemodynamic activity. Clutter filtering was then utilized to remove slow moving tissue components. The incoherent mean of this frame resulted in a single power doppler image which can be collected over time for functional information. FIG. 3B: Real-time 3D FUS imaging: A matrix array containing a grid of ultrasound elements is programmed to insonify biological tissue in parallel at multiple planes. Parallel GPU beamforming enables image reconstruction and data compression in real time. FIG. 3C: 3D Imaging in Awake-behaving animals: schematic of a custom ultrasound matrix array with both reduced profile and weight compared to standard clinical housings. Reduction in weight of both the array and cable permits ambulation during ultrasound imaging. Magnetized head mounts fixed to the animal's head ensure a stable connection with the head while allowing for easy detachment when needed.

FIG. 4 provides an amino acid sequence of a tentonin-3 polypeptide.

FIG. 5A-5B provide an amino acid sequence of a Piezo-1 polypeptide.

FIG. 6 provides an amino acid sequence of an OSCA1.2 polypeptide.

FIG. 7 provides an amino acid sequence of a TREK-1 polypeptide.

FIG. 8A-8B provide an amino acid sequence of a Piezo-2 polypeptide.

FIG. 9 provides an amino acid sequence of a TRAAK polypeptide.

FIG. 10 provides an amino acid sequence of a TRPV4 polypeptide.

FIG. 11 provides an amino acid sequence of a P2X7 polypeptide.

FIG. 12 provides an amino acid sequence of an MscL polypeptide.

FIG. 13A-13B provide a nucleotide sequence encoding an OSCA1.2 polypeptide.

FIG. 14 provides a nucleotide sequence encoding a Tentonin-3 (hTMEM150C) polypeptide.

FIG. 15A-15D provide a nucleotide sequence encoding a Piezo-1 polypeptide.

DEFINITIONS

Figure 1:
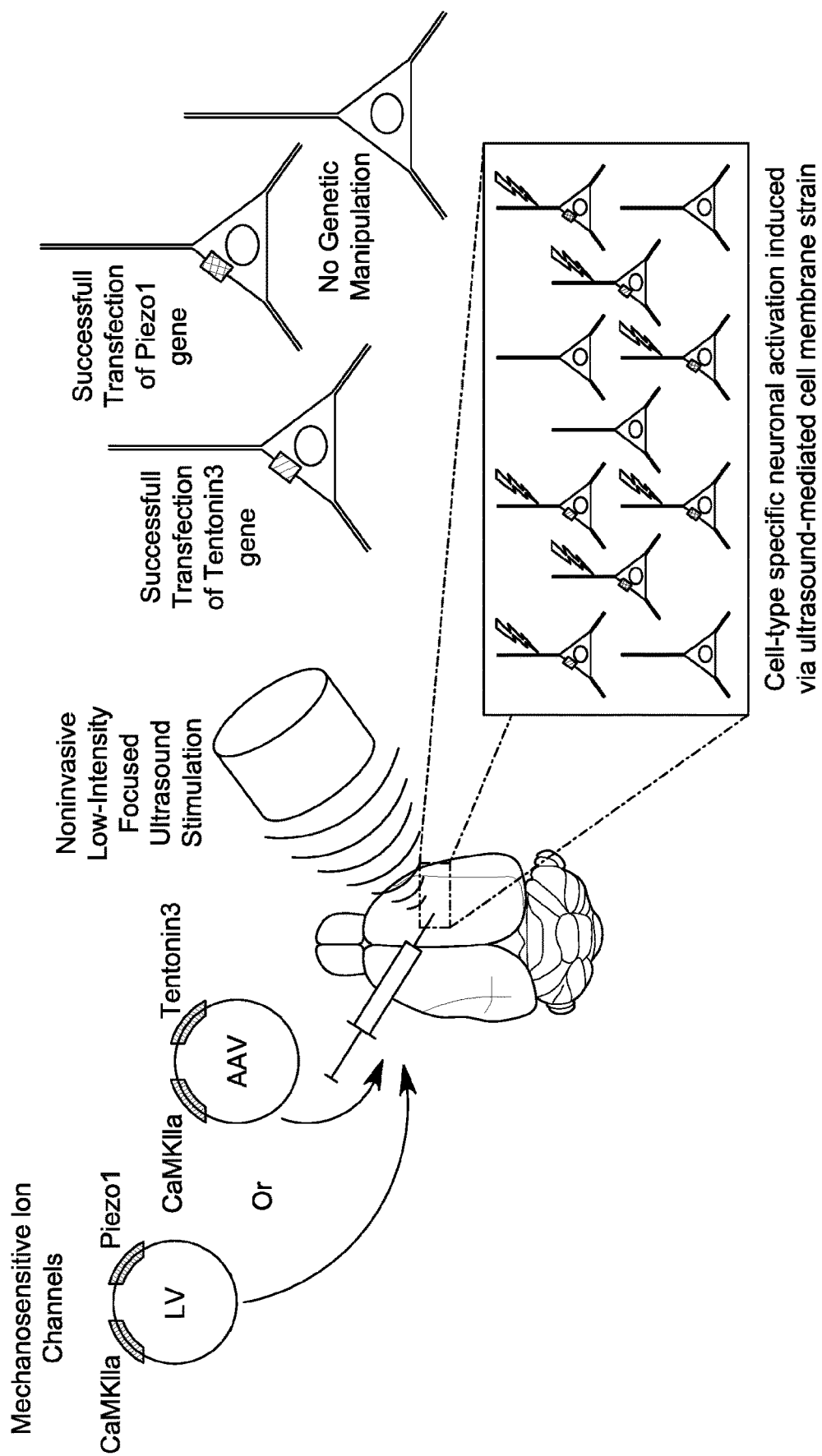
FIG. 1 depicts an embodiment of a method of the present disclosure. A recombinant expression vector encoding a mechanosensitive ion channel is injected into the brain, resulting in local expression of the channel in cells of the brain. Low-intensity focused ultrasound stimulation is applied to induce cell membrane strain, opening the mechanosensitive ion channel and selectively activating the cells.

As used herein, an "individual," "subject," or "patient" can be a mammal, including a human. Mammals include, but are not limited to, ungulates, canines, felines, bovines, ovines, non-human primates, lagomorphs, and rodents (e.g., mice and rats). In one aspect, an individual is a human. In another aspect, an individual is a non-human mammal.

The terms "polypeptide," "peptide," and "protein," used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like. $NH_2$ refers to the free amino group present at the amino terminus of a polypeptide. COOH refers to the free carboxyl group present at the carboxyl terminus of a polypeptide. In keeping with standard polypeptide nomenclature, *J. Biol. Chem.*, 243 (1969), 3552-59 is used.

The terms "polynucleotide" and "nucleic acid," used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The term "genetic modification" and refers to a permanent or transient genetic change induced in a cell following introduction into the cell of new nucleic acid (i.e., nucleic acid exogenous to the cell). Genetic change ("modification") can be accomplished by incorporation of the new nucleic acid into the genome of the host cell, or by transient or stable maintenance of the new nucleic acid as an extrachromosomal element. Where the cell is a eukaryotic cell, a permanent genetic change can be achieved by introduction of the nucleic acid into the genome of the cell. Suitable methods of genetic modification include viral infection, transfection, conjugation, protoplast fusion, electroporation, particle gun technology, calcium phosphate precipitation, direct microinjection, and the like.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a mechanosensitive ion channel" includes a plurality of such channels and reference to "the imaging device" includes reference to one or more such devices and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides a system for functional ultrasound imaging, where the system comprises: a) an apparatus for delivering a nucleic acid encoding a mechanosensitive ion channel to a target neural cell population in a region of a brain; and b) a functional ultrasound imaging device. The present disclosure provides a method for functional ultrasound imaging.

Systems for Functional Ultrasound Imaging

The present disclosure provides a system for functional ultrasound (fUS) imaging. In some embodiments, the system includes an apparatus (e.g., a delivery apparatus) as described herein. In some instances, the apparatus (delivery apparatus) is configured for delivering a nucleic acid encoding a mechanosensitive ion channel to a target neural cell population in a region of a brain.

In certain embodiments, the system includes a functional ultrasound (fUS) imaging device. The fUS imaging device can be configured to apply an ultrasound (US) signal to a target area, for example a target neural cell population in a region of the brain of an individual. In some cases, the target neural cell population includes neural cells which have been genetically modified to express a mechanosensitive ion channel, as described herein. Application of the ultrasound signal to the target neural cell population can lead to mechanical stimulation of cells in the target neural cell population by the ultrasound signal, thus activating the neural cells, for example by selectively inducing an action potential in the neural cells in response to the ultrasound signal. In some instances, the fUS imaging device is also configured to image the target region of the brain to produce a functional ultrasound image of the region of the brain.

The fUS imaging device can include one or more ultrasound transducers, which produce ultrasound waves and direct the ultrasound waves towards the target region so that the ultrasound signal is applied to the target neural cell population of interest. In addition, the ultrasound transducers can receive echo signals produced by the applied ultrasound signal. The ultrasound imaging device can analyze the received echo signals to produce an ultrasound image of the target region of interest.

In some instances, the one or more ultrasound transducers are configured in an array of ultrasound transducers. An array of ultrasound transducers includes any two-dimensional or three-dimensional arrangement of ultrasound transducers. An array may contain one or more, including two or more, four or more, 8 or more, 10 or more, 50 or more, or 100 or more, 250 or more, 500 or more, 750 or more, or 1000 or more ultrasound transducers.

In some cases, an array of ultrasound transducers can be a linear array of ultrasound transducers, where the ultrasound transducers are arranged in a substantially linear configuration. In certain embodiments, a linear array of ultrasound transducers facilitates the production of a two-dimensional image of the target region of interest by applying ultrasound signals in an imaging plane through the target region of interest. Echo signals received from the imaging plane can be used to produce a two-dimensional ultrasound image of the target region in the imaging plane. See, e.g., FIG. 3A. In some instances, the fUS imaging device can be configured to position the linear array of ultrasound transducers at one or more subsequent different imaging planes, such that one or more additional two-dimensional images of the target region of interest can be obtained. In certain cases, the fUS imaging device is configured to obtain a plurality of two-dimensional images of the target region of interest, which can be combined to produce a three-dimensional ultrasound image of the target region of interest. See, e.g., FIG. 3A.

In other instances, the array of ultrasound transducers can be arranged in a two-dimensional array (matrix array), such as where the ultrasound transducers are arranged in a two-dimensional planar array. In other instances, the two-dimensional array (matrix array) of ultrasound transducers can be arranged in a non-planar two-dimensional array, such as arranged in a two-dimensional array that is curved, for example where the two-dimensional array (matrix array) of ultrasound transducers is arranged in a shape comprising a portion of a sphere or paraboloid. In certain embodiments, a two-dimensional array of ultrasound transducers facilitates the production of a three-dimensional image of the target region of interest by applying ultrasound signals through multiple imaging planes through the target region of interest. Echo signals received from the multiple imaging planes can be used to produce a three-dimensional ultrasound image of the target region of interest. See, e.g., FIG. 3B and FIG. 3C. In some cases, a two-dimensional array of ultrasound transducers includes a plurality of rows of ultrasound transducers. In certain instances, each row of ultrasound transducers in a two-dimensional array can be controlled independently to apply ultrasound signals to corresponding imaging planes in the target region of interest. In some cases, each row of ultrasound transducers in a two-dimensional array can be controlled to simultaneously apply ultrasound signals to corresponding imaging planes in the target region of interest.

In certain embodiments, the ultrasound transducer or array of ultrasound transducers can apply ultrasound signals towards the target region of interest from a position outside of the subject being analyzed. As such, the fUS imaging device can be configured for non-invasive fUS imaging of the target region of interest in the subject. In some cases, the ultrasound transducer or array of ultrasound transducers is positioned above the target region of interest and at a certain distance away from the outside surface (e.g., skin surface) of the subject. In other instances, the ultrasound transducer or array of ultrasound transducers can be affixed to a subject, such as for example affixed to an area on the outside skin surface of the subject. In certain cases, an attachment device can be used to facilitate positioning of the ultrasound transducer or array of ultrasound transducers at a position above the target region of interest. The attachment device can be affixed to the outside surface (e.g., skin surface) of the subject, for example using an adhesive, and the ultrasound transducer or array of ultrasound transducers can be attached to the attachment device. Any convenient attachments can be used to attach the ultrasound transducer or array of ultrasound transducers to the attachment device, such as, but not limited to, clips, screws, snaps, adhesive, a magnetic attachment, and the like.

In certain embodiments, the fUS imaging device is configured to have an ultrafast temporal resolution. For example, the fUS imaging device can be configured to apply ultrasound signals and acquire ultrasound images at a temporal resolution of 100 ms or less, such as 90 ms or less, 80 ms or less, 70 ms or less, 60 ms or less, 50 ms or less, 40 ms or less, 30 ms or less, 20 ms or less, 10 ms or less, 7 ms or less, 5 ms or less, 4 ms or less, 3 ms or less, 2 ms or less, 1 ms or less, 900 µs or less, 800 µs or less, 700 µs or less, 600 is or less, 500 µs or less, 400 µs or less, 300 µs or less, 200 µs or less, 100 µs or less, 75 is or less, 50 µs or less, 25 µs or less, or 10 µs or less. Stated another way, the fUS imaging device can be configured to apply ultrasound signals and acquire ultrasound images at a frame rate of 10 Hz or more, 50 Hz or more, 100 Hz or more, 200 Hz or more, 300 Hz or more, 400 Hz or more, 500 Hz or more, 600 Hz or more, 700 Hz or more, 800 Hz or more, 900 Hz or more, 1000 Hz or more, 1250 Hz or more, 1500 Hz or more, 1750 Hz or more, 2000 Hz or more, 2500 Hz or more, 3000 Hz or more, 3500 Hz or more, 4000 Hz or more, 4500 Hz or more, 5000 Hz or more, 5500 Hz or more, 6000 Hz or more, 6500 Hz or more, 7000 Hz or more, 7500 Hz or more, 8000 Hz or more, 8500 Hz or more, 9000 Hz or more, 9500 Hz or more, 10,000 Hz or more, 15,000 Hz or more, 20,000 Hz or more, 25,000 Hz or more, 30,000 Hz or more, 35,000 Hz or more, 40,000 Hz or more, 45,000 Hz or more, 50,000 Hz or more, 55,000 Hz or more, 60,000 Hz or more, 65,000 Hz or more, 70,000 Hz or more, 75,000 Hz or more, 80,000 Hz or more, 85,000 Hz or more, 90,000 Hz or more, 95,000 Hz or more, or 100,000 Hz or more.

In certain embodiments, the fUS imaging device is configured to have a high spatial resolution, such as a spatial resolution on the micron-scale. For example, the fUS imaging device can be configured to have a spatial resolution of 1 mm or less, such as 900 µm or less, 800 µm or less, 700 µm or less, 600 µm or less, 500 µm or less, 400 µm or less, 300 µm or less, 200 µm or less, 100 µm or less, 90 µm or less, 80 µm or less, 70 µm or less, 60 µm or less, 50 µm or less, 40 µm or less, 30 µm or less, 20 µm or less, 10 µm or less, 5 µm or less, or 1 µm or less.

In some cases, the fUS imaging device is configured to acquire functional ultrasound images of a target region of interest. For example, the fUS imaging device can be configured to monitor the functional activity in the target region of interest, such as the functional activity in a target neural cell population. The fUS imaging device can be configured to monitor the functional activity in the target region of interest over time. In some instances, the fUS imaging device is configured to monitor the functional activity in the target region of interest in real-time. By real-time is meant that the fUS imaging device has a temporal resolution sufficient to acquire ultrasound images of functional activity in the target region as the activity is occurring.

Systems of the present disclosure are configured for performing the methods of the present disclosure, as described herein. In some cases, the system may include a fUS imaging device, a processor, and a memory (e.g., a non-transient computer-readable memory). The memory may contain an application or program that, when executed by the processor, causes the fUS imaging device to record functional activity of an individual's brain to generate functional activity data for the individual, and further perform a method of analyzing functional activity data, as described herein.

The system can include one or more processors, memory (i.e., a computer-readable storage medium), an input/output (I/O) interface, and a communications interface. These components communicate with one another over one or more communication buses or signal lines. In some embodiments, the memory, or the computer-readable storage medium or memory, stores an operating system, programs, modules, instructions, and stored data. The one or more processors are coupled to the memory and operable to execute these programs, modules, and instructions, and read/write from/to the stored data.

In some embodiments, the processor includes one or more microprocessors, such as a single core or multi-core microprocessor. In some embodiments, the processor includes one or more general purpose processors. In some embodiments, the processor includes one or more special purpose processors (e.g., programmed to execute the methods described herein).

In some embodiments, the memory includes high-speed random access memory, such as DRAM, SRAM, DDR RAM or other random access solid state memory devices. In some embodiments, the memory includes non-volatile memory, such as one or more magnetic disk storage devices, optical disk storage devices, flash memory devices, or other non-volatile solid state storage devices. In some embodiments, the memory includes one or more storage devices remotely located from the processor. The memory, or alternately the non-volatile memory device(s) within the memory, can include a computer-readable storage medium. In some embodiments, the memory includes a non-transitory computer-readable storage medium.

In some embodiments, the I/O interface is coupled to one or more input/output devices, such as one or more displays, keyboards, touch-sensitive surfaces (such as a track pad or a touch-sensitive surface of a touch-sensitive display), speakers, and microphones. The I/O interface may be configured to receive user inputs (e.g., voice input, keyboard inputs, touch inputs, etc.) from a user and process them accordingly. The I/O interface may also be configured to present outputs (e.g., sounds, images, text, etc.) to the user according to various program instructions implemented on the system.

In some embodiments, the communications interface includes wired communication port(s) and/or wireless transmission and reception circuitry. The wired communication port(s) receive and send communication signals via one or more wired interfaces, e.g., Ethernet, Universal Serial Bus (USB), FIREWIRE, and the like. The wireless circuitry receives and sends RF signals, infrared signals, and/or optical signals from/to communications networks and other communications devices. The wireless communications may use any of a plurality of communications standards, protocols and technologies, such as GSM, EDGE, CDMA, TDMA, Bluetooth, Wi-Fi, VoIP, Wi-MAX, or any other suitable wireless communication protocol. The network communications interface enables communication between the system with networks, such as the Internet, an intranet and/or a wireless network, such as a cellular telephone network, a local area network (LAN) a wireless local area network (WLAN) and/or a metropolitan area network (MAN), and other devices. Network communications interface is configured to facilitate communications between the system and other devices over a network.

In some aspects, the system may include a computer, which may be a personal computing device (e.g., laptop, desktop, workplace computer, portable device, etc.). A computer that is a personal computing device may not need to be connected to a network. In other instances, a computer that is a personal computing device is connected to a network (e.g., a wired or wireless connection as described above).

In some aspects, the computer is a server or a collection of servers, and may not need an I/O interface. For example, the computer may be a server, and a program of the present disclosure may be accessed by a user through a website.

In some embodiments, the operating system (e.g., LINUX®, UNIX®, OS X®, WINDOWS®, or an embedded operating system) includes various software components and/or drivers for controlling and managing general system tasks (e.g., memory management, storage device control, power management, etc.) and facilitates communications between various hardware, firmware, and software components.

It should be noted that the system is only one example, and that the system may have more or fewer components than described herein, may combine two or more components, or may have a different configuration or arrangement of the components. The various components of the system may be implemented in hardware, software, firmware, including one or more signal processing and/or application specific integrated circuits, or a combination of thereof.

In some cases, a program executed by the fUS imaging device may be configured to computationally process functional activity data for a region of a brain of an individual, as described above, to generate an estimate of the relative activities of neural pathways regulated by each of a plurality of neuronal subtypes, and generate a connectivity model from the functional activity data based on a network model of functional connections among interconnected nodes representing the region. The present system may include an fUS imaging device configured to measure functional brain activity of an individual. The system may be in communication with the fUS device, through the communication interface, such that the computer system can control operation of the fUS device and/or retrieve functional imaging data from the fUS device.

The methods described herein may be performed by the computer system. In some embodiments, the computer system is a distributed computer system. For example, the computer system may include a first set of one or more processors located remotely from a second set of one or more processors. In some embodiments, the computer system includes a web server configured to provide a web interface. In some embodiments, the web interface is configured to receive data. In some embodiments, the web interface is configured to display results.

In some cases, the fUS imaging device is configured for uniplex analysis of a target area (e.g., target tissue or organ) in a subject. By "uniplex analysis" is meant that a single target area is analyzed using the devices and methods disclosed herein. For example, a single ultrasound transducer or array of ultrasound transducers may be used for analysis of one target area in a subject. In these embodiments, the fUS imaging device is configured for detection and analysis of single-unit activity in a subject.

Other embodiments include systems configured for the multiplex analysis of two or more target areas (e.g., target tissues or organs) in a subject. By "multiplex analysis" is meant that the two or more areas of neural cells may be analyzed using the devices and methods disclosed herein. For example, the system may include two or more ultrasound transducers or an array of ultrasound transducers. In some instances, the number of target areas for analysis using multiplex devices as disclosed herein is 2 or more, such as 4 or more, 6 or more, 8 or more, 10 or more, etc., up to 20 or more, e.g., 50 or more, including 100 or more, or 500 or more distinct target areas. In certain embodiments, the devices and methods may be used for the multiplex analysis of 2 to 500 distinct target areas in the subject, such as 2 to 250 distinct target areas, including 2 to 100 distinct target areas, or 2 to 50 distinct target areas, or 2 to 25 distinct target areas, or 2 to 10 distinct target areas. In certain embodiments, 2 or more multiplex assays may be conducted in parallel substantially simultaneously.

Mechanosensitive Ion Channels

As discussed above, a cell is modified with a mechanosensitive ion channel, or a nucleic acid comprising a nucleotide sequence encoding a mechanosensitive ion channel.

Mechanosensitive ion channels are known in the art, and any known mechanosensitive ion channel can be used. Non-limiting examples of mechanosensitive ion channels are tentonin-3 (TTN3; also known as TMEM150C); Piezo-1; Piezo-2; an OSCA/TMEM63 family member (e.g., OSCA1.2); TREK-1; TRAAK; TRPV4; P2X7; BK (Slot); and MscL.

For example, in some cases, a cell is modified with a Tentonin-3 (TTN3) polypeptide, or a nucleic acid comprising a nucleotide sequence encoding a TTN3 (TTEM150C) polypeptide. In some cases, a TTN3 polypeptide comprises an amino acid sequence having at least 80%, at least 85%, at least 90%, at least 95%, at least 98%, at least 99%, or 100%, amino acid sequence identity to the TTN3 amino acid depicted in FIG. 4; and has a length of from about 225 amino acids to about 275 amino acids, from about 225 amino acids to about 250 amino acids, from about 250 amino acids to about 260 amino acids, or from about 250 amino acids to about 275 amino acids.

As another example, in some cases, a cell is modified with a Piezo-1 polypeptide, or a nucleic acid comprising a nucleotide sequence encoding a Piezo-1 polypeptide. In some cases, a Piezo-1 polypeptide comprises an amino acid sequence having at least 80%, at least 85%, at least 90%, at least 95%, at least 98%, at least 99%, or 100%, amino acid sequence identity to the Piezo-1 amino acid sequence depicted in FIG. 5A-5B; and has a length of from about 2500 amino acids to about 2550 amino acids, from about 2500 amino acids to about 2520 amino acids, from about 2520 amino acids to about 2525 amino acids, or from about 2525 amino acids to about 2550 amino acids.

As another example, in some cases, a cell is modified with an OSCA1.2 polypeptide, or a nucleic acid comprising a nucleotide sequence encoding an OSCA1.2 polypeptide. In some cases, an OSCA1.2 polypeptide comprises an amino acid sequence having at least 80%, at least 85%, at least 90%, at least 95%, at least 98%, at least 99%, or 100%, amino acid sequence identity to the OSCA1.2 amino acid sequence depicted in FIG. 6; and has a length of from about 750 amino acids to about 800 amino acids, or from about 750 amino acids to about 775 amino acids, or from about 760 amino acids to about 780 amino acids, or from about 755 amino acids to about 770 amino acids.

As another example, in some cases, a cell is modified with a TREK-1 polypeptide, or a nucleic acid comprising a nucleotide sequence encoding a TREK-1 polypeptide. In some cases, a TREK-1 polypeptide comprises an amino acid sequence having at least 80%, at least 85%, at least 90%, at least 95%, at least 98%, at least 99%, or 100%, amino acid sequence identity to the TREK-1 amino acid sequence depicted in FIG. 7; and has a length of from about 400 amino acids to about 425 amino acids, or from about 400 amino acids to about 411 amino acids, or from about 410 amino acids to about 425 amino acids.

As another example, in some cases, a cell is modified with a Piezo-2 polypeptide, or a nucleic acid comprising a nucleotide sequence encoding a Piezo-2 polypeptide. In some cases, a Piezo-2 polypeptide comprises an amino acid sequence having at least 80%, at least 85%, at least 90%, at least 95%, at least 98%, at least 99%, or 100%, amino acid sequence identity to the Piezo-2 amino acid sequence depicted in FIG. 8A-8B; and has a length of from about 2725 amino acids to about 2775 amino acids, from about 2740 amino acids to about 2760 amino acids, from about 2750 amino acids to about 2755 amino acids, or from about 2735 amino acids to about 2760 amino acids.

As another example, in some cases, a cell is modified with a TRAAK polypeptide, or a nucleic acid comprising a nucleotide sequence encoding a TRAAK polypeptide. In some cases, a TRAAK polypeptide comprises an amino acid sequence having at least 80%, at least 85%, at least 90%, at least 95%, at least 98%, at least 99%, or 100%, amino acid sequence identity to the TRAAK amino acid sequence depicted in FIG. 9; and has a length of from about 375 amino acids to about 425 amino acids, from about 390 amino acids to about 410 amino acids, from about 390 amino acids to about 395 amino acids, or from about 380 amino acids to about 405 amino acids.

As another example, in some cases, a cell is modified with a TRPV4 polypeptide, or a nucleic acid comprising a nucleotide sequence encoding a TRPV4 polypeptide. In some cases, a TRPV4 polypeptide comprises an amino acid sequence having at least 80%, at least 85%, at least 90%, at least 95%, at least 98%, at least 99%, or 100%, amino acid sequence identity to the TRPV4 amino acid sequence depicted in FIG. 10; and has a length of from about 725 amino acids to about 775 amino acids, from about 750 amino acids to about 770 amino acids, from about 760 amino acids to about 765 amino acids, or from about 755 amino acids to about 770 amino acids.

As another example, in some cases, a cell is modified with a P2X7 polypeptide, or a nucleic acid comprising a nucleotide sequence encoding a P2X7 polypeptide. In some cases, a P2X7 polypeptide comprises an amino acid sequence having at least 80%, at least 85%, at least 90%, at least 95%, at least 98%, at least 99%, or 100%, amino acid sequence identity to the P2X7 amino acid sequence depicted in FIG. 11; and has a length of from about 575 amino acids to about 625 amino acids, from about 590 amino acids to about 610 amino acids, from about 590 amino acids to about 600 amino acids, or from about 585 amino acids to about 600 amino acids.

As another example, in some cases, a cell is modified with a MscL polypeptide, or a nucleic acid comprising a nucleotide sequence encoding a MscL polypeptide. In some cases, a MscL polypeptide comprises an amino acid sequence having at least 80%, at least 85%, at least 90%, at least 95%, at least 98%, at least 99%, or 100%, amino acid sequence identity to the MscL amino acid sequence depicted in FIG. 12; and has a length of from about 125 amino acids to about 175 amino acids, from about 130 amino acids to about 150 amino acids, from about 135 amino acids to about 145 amino acids, or from about 135 amino acids to about 150 amino acids.

A nucleic acid comprising a nucleotide sequence encoding a mechanosensitive ion channel can be delivered to an organ or tissue.

In some cases, a nucleotide sequence encoding a mechanosensitive ion channel is operably linked to a promoter. In some cases, the promoter provides for expression of the nucleotide sequence in a brain cell (e.g., a neuronal cell). The promoter used to drive expression of a mechanosensitive ion channel can be a Thy1 promoter (See, e.g., Llewellyn, et al., 2010, Nat. Med., 16(10):1161-1166). In some cases, the promoter used to drive expression of a mechanosensitive ion channel can be a human synapsin (hSyn) promoter, a human elongation factor 1-α (EF1α) promoter, a cytomegalovirus (CMV) promoter, a CMV early enhancer/chicken β actin (CAG) promoter, a synapsin-I promoter (e.g., a human synapsin-I promoter), a human synuclein 1 promoter, a human Thy1 promoter, a calcium/calmodulin-dependent kinase II alpha (CAMKIIα) promoter, or any other promoter capable of driving expression of a nucleotide sequence encoding a mechanosensitive ion channel in a target cell.

Neuron-specific promoters and other control elements (e.g., enhancers) are known in the art. Suitable neuron-specific control sequences include, but are not limited to, a neuron-specific enolase (NSE) promoter (see, e.g., EMBL HSENO2, X51956; see also, e.g., U.S. Pat. Nos. 6,649,811, 5,387,742); an aromatic amino acid decarboxylase (AADC) promoter; a neurofilament promoter (see, e.g., GenBank HUMNFL, L04147); a synapsin promoter (see, e.g., GenBank HUMSYNIB, M55301); a thy-1 promoter (see, e.g., Chen et al. (1987) Cell 51:7-19; and Llewellyn et al. (2010) Nat. Med. 16:1161); a serotonin receptor promoter (see, e.g., GenBank S62283); a tyrosine hydroxylase promoter (TH) (see, e.g., Nucl. Acids. Res. 15:2363-2384 (1987) and Neuron 6:583-594 (1991)); a GnRH promoter (see, e.g., Radovick et al., Proc. Natl. Acad. Sci. USA 88:3402-3406 (1991)); an L7 promoter (see, e.g., Oberdick et al., Science 248:223-226 (1990)); a DNMT promoter (see, e.g., Bartge et al., Proc. Natl. Acad. Sci. USA 85:3648-3652 (1988)); an enkephalin promoter (see, e.g., Comb et al., EMBO J. 17:3793-3805 (1988)); a myelin basic protein (MBP) promoter; a CMV enhancer/platelet-derived growth factor-β promoter (see, e.g., Liu et al. (2004) Gene Therapy 11:52-60); a motor neuron-specific gene Hb9 promoter (see, e.g., U.S. Pat. No. 7,632,679; and Lee et al. (2004) Development 131:3295-3306); and an alpha subunit of Ca($^{2+}$)-calmodulin-dependent protein kinase II (CaMKIIα) promoter (see, e.g., Mayford et al. (1996) Proc. Natl. Acad. Sci. USA 93:13250).

A nucleic acid comprising a nucleotide sequence encoding a mechanosensitive ion channel can be present in a recombinant expression vector that provides for expression of the mechanosensitive ion channel in a target cell. Vectors according to the present disclosure also include vectors comprising a nucleotide sequence that encodes an RNA (e.g., an mRNA) that when transcribed from the polynucleotides of the vector will result in the accumulation of a subject protein on the plasma membranes of target cells. Vectors which may be used include, without limitation, lentiviral, herpes simplex virus (HSV), adenoviral, and adeno-associated viral (AAV) vectors. Lentiviruses include, but are not limited to, human immunodeficiency virus (HIV)-1, HIV-2, simian immunodeficiency virus (SIV), feline immunodeficiency virus (FIV), and equine infectious anemia virus (EIAV). Lentiviruses may be pseudotyped with the envelope proteins of other viruses, including, but not limited to vesicular stomatitis virus (VSV), rabies, Momurine leukemia virus (MLV), baculovirus, and Ebola. Such vectors may be prepared using standard methods in the art.

In some cases, a vector may be a recombinant AAV vector. AAV vectors are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome that contains the rep gene involved in viral replication and expression of the viral genes; and the right-hand part of the genome that contains the cap gene encoding the capsid proteins of the virus.

AAV vectors may be prepared using standard methods in the art. Adeno-associated viruses of any serotype are suitable (see, e.g., Blacklow, pp. 165-174 of "Parvoviruses and Human Disease" J. R. Pattison, ed. (1988); Rose, Comprehensive Virology 3:1, 1974; P. Tattersall "The Evolution of Parvovirus Taxonomy" In Parvoviruses (J R Kerr, S F Cotmore. M E Bloom, R M Linden, C R Parrish, Eds.) p 5-14, Hudder Arnold, London, U K (2006); and D E Bowles, J E Rabinowitz, R J Samulski "The Genus Dependovirus" (J R Kerr, S F Cotmore. M E Bloom, R M Linden, C R Parrish, Eds.) p 15-23, Hudder Arnold, London, UK (2006), the disclosures of each of which are hereby incorporated by reference herein in their entireties). Methods for purifying for vectors may be found in, for example, U.S. Pat. Nos. 6,566,118, 6,989,264, and 6,995,006 and WO/1999/011764 titled "Methods for Generating High Titer Helper-free Preparation of Recombinant AAV Vectors", the disclosures of which are herein incorporated by reference in their entirety. Methods of preparing AAV vectors in a baculovirus system are described in, e.g., WO 2008/024998. AAV vectors can be self-complementary or single-stranded. Preparation of hybrid vectors is described in, for example, PCT Application No. PCT/US2005/027091, the disclosure of which is herein incorporated by reference in its entirety. The use of vectors derived from the AAVs for transferring genes in vitro and in vivo has been described (See e.g., International Patent Application Publication Nos.: 91/18088 and WO 93/09239; U.S. Pat. Nos. 4,797,368, 6,596,535, and 5,139,941; and European Patent No.: 0488528, all of which are hereby incorporated by reference herein in their entireties). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication-defective recombinant AAVs according to the present disclosure can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In some cases, the vector(s) for use in the methods of the present disclosure are encapsulated into a virus particle (e.g. AAV virus particle including, but not limited to, AAV1, AAV2, AAV3, AAV4, AAV5, AAV6, AAV7, AAV8, AAV9, AAV10, AAV11, AAV12, AAV13, AAV14, AAV15, and AAV16). Accordingly, the present disclosure includes a recombinant virus particle (recombinant because it contains a recombinant polynucleotide) comprising any of the vectors described herein. Methods of producing such particles are known in the art and are described in U.S. Pat. No. 6,596,535, the disclosure of which is hereby incorporated by reference in its entirety.

In some cases, the subject anion channel proteins can be combined with various promoters and/or fluorescent proteins for targeting specific neuronal populations in mammalian brains. Other AAV vectors that may be used in association with the polynucleotides include those with double floxed inverted reading frames (DIO) which allow expression of proteins under the control of recombinases such as Cre and Flp.

In some cases, a nucleotide sequence encoding a mechanosensitive ion channel is codon optimized for expression in a human cell.

Non-limiting examples of nucleotide sequences encoding mechanosensitive ion channels are provided in FIG. 13A-13B, FIG. 14, and FIG. 15A-15D.

Delivery Apparatus

A system of the present disclosure can include a delivery apparatus (delivery device) that is configured to deliver a pharmaceutical composition comprising; a) a nucleic acid comprising a nucleotide sequence encoding a mechanosensitive ion channel as described herein; and b) a pharmaceutically acceptable carrier. A system of the present disclosure can include a delivery apparatus (delivery device) that is configured to deliver a pharmaceutical composition comprising; a) a mechanosensitive ion channel as described herein; and b) a pharmaceutically acceptable carrier. Thus, a system of the present disclosure includes an apparatus for delivering to a target neural cell population in a region of the brain: i) a composition comprising a nucleic acid comprising nucleotide sequence encoding a mechanosensitive ion channel; or ii) a composition comprising a mechanosensitive ion channel.

A delivery device can provide regular, irregular, programmed, or clinician- or patient-activated doses of a composition comprising a nucleic acid comprising a nucleotide sequence encoding a mechanosensitive ion channel to one or more target cells to ensure that the target cells continue to express the mechanosensitive ion channel for a desired period of time.

A suitable delivery device may generally include various components, such as reservoirs, pumps, actuators, tubing components, needles, catheters, and any other suitable components for delivering the subject pharmaceutical compositions to a target cell or tissue of a patient.

For example, a delivery device can comprise a reservoir that can contain a liquid composition comprising a nucleic acid (e.g., a recombinant expression vector) comprising a nucleotide sequence encoding a mechanosensitive ion channel. The delivery device can comprise: a) a reservoir that can contain a liquid composition comprising a nucleic acid (e.g., a recombinant expression vector) comprising a nucleotide sequence encoding a mechanosensitive ion channel; and b) a catheter for delivering the liquid composition from the reservoir into a patient. A pump can provide for delivering the liquid composition from the reservoir, through the catheter, and into a patient. The delivery device can be completely or partially implantable. For example, the reservoir can be outside of the patient, or can be implanted in the patient.

Delivery devices may also include components that facilitate computerized operation, such as a power source, a processor comprising a memory, a user input device, and/or a graphical user interface. In some cases, a delivery device may be completely or partially implantable within a patient. In some cases, a delivery device may be operated by a caregiver, wherein the device is introduced into a portion of the patient's body, e.g., into the patient's brain, and a subject pharmaceutical composition is delivered to a target tissue, e.g., a portion of the patient's brain. In some cases, following delivery of the pharmaceutical composition, the device may be removed. In other instances, the device may be kept in place for later delivery of additional pharmaceutical compositions.

Methods for Functional Ultrasound Imaging

Methods for functional ultrasound (fUS) imaging can provide a non-invasive, brain-wide measure representative of neural activity. The methods disclosed herein are amenable to revealing causal links between different brain regions in a single living individual (e.g., a single mouse or rat, a single human, a single non-human mammal) by using a combination of neuronal stimulation and activity measurement protocols, as described above. Thus, in some embodiments, a brain functional circuit is assayed in a single animal using a combination of mechanogenetics and fUS.

Methods of the present disclosure may use any number of combinations of suitable neuronal stimulation and neuronal activity measurement protocols, as necessary, to determine the functional connections between different brain regions. Suitable protocols include functional ultrasound (fUS) imaging and behavioral analysis. Behavioral analysis may include any suitable behavioral assays, such as behavioral assays for arousal, memory (such as a water maze assay), conditioning (such as fear conditioning), sensory responses (responses to e.g., visual, somatosensory, auditory, gustatory, and/or olfactory cues).

In general terms, an implementation of the present method may include using a combination of mechanogenetic stimulation of a defined set of target neurons in a region of the brain, and measuring the response of the target neurons by scanning the brain with fUS. Thus, the neurons in the target region may be genetically modified to contain a mechanosensitive polypeptide, e.g., a mechanosensitive ion channel, where the mechanosensitive polypeptide is configured to modulate the activity of, e.g., depolarize or hyperpolarize, the neuron upon applying an ultrasound signal (i.e., ultrasound waves) to the target region with an ultrasound stimulus of appropriate intensity to induce depolarization or hyperpolarization of the target neuron(s). In some cases, the neurons of the target region express the mechanosensitive polypeptide. In some cases, the neurons of the target region are genetically modified, e.g., by viral infection of a DNA construct containing nucleotide sequences encoding the mechanosensitive polypeptide and any other appropriate regulatory elements, to express the mechanosensitive polypeptide. Any suitable mechanosensitive polypeptide may be used, as described further herein.

The ultrasound stimulus used to activate the mechanosensitive polypeptide may include ultrasound signals characterized by, e.g., frequency, pulse width, duty cycle, wavelength, intensity, etc. In some cases, the ultrasound stimulus includes two or more different sets of ultrasound pulses, where each set of ultrasound pulses is characterized by different temporal patterns of ultrasound pulses. The temporal pattern may be characterized by any suitable parameter, including, but not limited to, frequency, period (i.e., total duration of the ultrasound stimulus), pulse width, duty cycle, etc.

The variation in the property of the ultrasound signals may be reflected in a difference in the activity of the target neurons. In some cases, where the target neuron is depolarized by activation of the mechanosensitive polypeptide, an increase in the frequency or intensity of the ultrasound signals may cause an increase in the frequency of action potential firing in the target neurons. In some embodiments, the frequency of action potential firing in the target neurons scales quantitatively with the increase in the frequency or intensity of the ultrasound signals.

The ultrasound signals of a set may have any suitable frequency. In some cases, the ultrasound signals have a frequency of 1 MHz or more, e.g., 3 MHz or more, 5 MHz or more, 10 MHz or more, 15 MHz or more, 20 MHz or more, 25 MHz or more, 30 MHz or more, 35 MHz or more, 40 MHz or more, or 50 MHz or more, or 75 MHz or more, or 100 MHz or more.

In some cases, the ultrasound signals are characterized by having a certain pulse width. For example, the ultrasound signals may have any suitable pulse width, such as, but not limited to, a pulse width of 0.00001 ms or longer, e.g., 0.00002 ms or longer, 0.00005 ms or longer, 0.00007 ms or longer, 0.0001 ms or longer, 0.0002 ms or longer, 0.0005 ms or longer, including 0.0007 ms or longer, or 0.001 ms or longer.

In some cases, the ultrasound signals are characterized by a certain duty cycle. The duty cycle is a percentage (or ratio) related to the "on time" for a pulsed signal and can be calculated as follows: duty cycle=(pulse width)/frequency. For example, the duty cycle of the ultrasound signals may be any suitable duty cycle, such as, but not limited to a duty cycle of 1% or more, e.g., 5% or more, 10% or more, 15% or more, 20% or more including 25% or more, or 30% or more, or 35% or more, or 40% or more, or 45% or more, or 50% or more, and may be 80% or less, e.g., 75% or less, 70% or less, 65% or less, 60% or less, 65% or less, 50% or less, 45% or less, including 40% or less, or 35% or less, or 30% or less. In certain embodiments, the duty cycle is in the range of 1 to 80%, e.g., 5 to 70%, 5 to 60%, including 10 to 50%, or 10 to 40%.

The average power of the ultrasound signals may be any suitable power, such as, but not limited to a power of 1 $W/cm^2$ or more, e.g., 5 $W/cm^2$ or more, 10 $W/cm^2$ or more, 15 $W/cm^2$ or more, including 20 $W/cm^2$ or more, or 25 $W/cm^2$ or more, or 30 $W/cm^2$ or more, or 35 $W/cm^2$ or more, or 40 $W/cm^2$ or more, or 45 $W/cm^2$ or more, or 50 $W/cm^2$ or more, and may be 100 $W/cm^2$ or less, e.g., 90 $W/cm^2$ or less, 80 $W/cm^2$ or less, 70 $W/cm^2$ or less, 60 $W/cm^2$ or less, 50 $W/cm^2$ or less. In some embodiments, the power is in the range of 1 $W/cm^2$ to 100 $W/cm^2$, e.g., 5 $W/cm^2$ to 75 $W/cm^2$, 5 $W/cm^2$ to 50 $W/cm^2$, 5 $W/cm^2$ to 25 $W/cm^2$.

The wavelength and intensity of the ultrasound signals may vary and may depend on the activation wavelength of the mechanosensitive polypeptide, ultrasound transparency of the region of the brain, the desired volume of the brain to be exposed to the ultrasound signals, etc.

The volume of a brain region to which the ultrasound signals are applied may be any suitable volume. In some cases, the volume of the target region is 0.001 $mm^3$ or more, e.g., 0.005 $mm^3$ or more, 0.001 $mm^3$ or more, 0.005 $mm^3$ or more, 0.01 $mm^3$ or more, 0.05 $mm^3$ or more, including 0.1 $mm^3$ or more, and is 100 $mm^3$ or less, e.g., 50 $mm^3$ or less, 20 $mm^3$ or less, 10 $mm^3$ or less, 5 $mm^3$ or less, 1 $mm^3$ or less, including 0.1 $mm^3$ or less. In certain cases, the volume of the target region is in the range of 0.001 to 100 $mm^3$, e.g., 0.005 to 20 $mm^3$, 0.01 to 10 $mm^3$, 0.01 to 5 $mm^3$, including 0.05 to 1 $mm^3$.

In certain embodiments, an implementation of the present method may include using a combination of mechanogenetic stimulation of a defined set of neurons in a first region of the brain, and measuring the response at a whole-brain level by scanning the brain with fUS, to determine a dynamic functional connection between the first region and a second region of the brain. Thus, the neurons in the first region may be modified to contain a mechanosensitive polypeptide, e.g., a mechanosensitive ion channel, where the mechanosensitive polypeptide is configured to modulate the activity of, e.g., depolarize or hyperpolarize, the neuron upon stimulating the first region with an ultrasound stimulus of appropriate wavelength, target region volume and intensity. In some cases, the neurons of the first region express the mechanosensitive polypeptide. In some cases, the neurons of the first region are genetically modified, e.g., by viral infection of a DNA construct containing nucleotide sequences encoding the mechanosensitive polypeptide and any other appropriate regulatory elements, to express the mechanosensitive polypeptide. Any suitable mechanosensitive polypeptide may be used, as described further herein.

The responses to the stimulation by the ultrasound signals may be measured by fUS for different regions of the brain, and a comparison of the responses in each region may indicate a functional connection between neurons stimulated by the ultrasound signals to the first region and one or more other regions of the brain. For example, upon applying ultrasound signals to a first region of the brain, neurons in the first region may generate action potentials induced by the applied ultrasound signals. fUS can then be used to measure activity in a second region of the brain. In some cases, a change in neural activity in the second region induced by the ultrasound signals can be measured by fUS, thus indicating a functional connection between neurons in the first region of the brain and the second region of the brain.

In addition, in some embodiments, a second change in neural activity induced by a second set of ultrasound signals in the second region can also be measured by fUS. In some instances, there may be a difference between the first measured change in neural activity and the second measured change in neural activity. Based on the difference between the first measured change in neural activity and the second measured change in neural activity, a dynamic functional connection between the neurons in the first region of the brain and the second region of the brain may be identified. For instance, the dynamic functional connection between the neurons in the first region of the brain and the second region of the brain may be identified by calculating a difference between the first measured change and the second measured change in neural activity. If the calculated difference between the first measured change and the second measured change in neural activity is qualitatively or quantitatively different, this may be an indication that there is a dynamic functional connection from the neurons in the first region of the brain to the neurons in the second region of the brain.

Another aspect of the present methods includes identifying neurons in a third region of the brain that may mediate the dynamic functional connection between the first and second regions, as described above. Thus, the neurons of the third region may be said to represent a node, e.g., a modulatory node, of the dynamic functional connection between the first and second regions, where the neurons of the third region have functional connections to both the first and second regions. In some cases, identifying a modulatory node of the dynamic functional connection may include using functional ultrasound imaging as described above.

In some embodiments, neurons in a third region of the brain that may mediate the dynamic functional connection between the first and second regions may be identified by measuring the effect of disrupting the normal activity of the neurons of the third region on the dynamic properties of the functional connection between neurons of the first and second regions. If normal activity of the neurons of the third region is required for the dynamic functional connection, then the neurons of the third region may represent a modulatory node for the dynamic functional connection.

The normal activity of the neurons of the third region may be disrupted using any suitable method. In some cases, the activity is disrupted by activating a mechanosensitive polypeptide, e.g., a mechanosensitive ion channel for a normally activated neuron, in the neurons of the third region, via application of an ultrasound signal to the third region sufficient for activating the mechanosensitive polypeptide. By comparing the change in response of neurons in the second region to a first set of ultrasound signals that activates mechanosensitive polypeptides in neurons of the first region, in the presence or absence of a third set of ultrasound signals applied to the third region, the role of the neurons of the third region in the dynamic functional connection between the first and second regions may be determined. Thus, if application of ultrasound signals to the third region disrupts the normal activity, e.g., reduces, abolishes or otherwise alters the response of the neurons in the second region to the first set of ultrasound signals, the neurons of the third region may mediate the dynamic functional connection. In some cases, the response of the neurons in the second region to the first set of ultrasound signals may be reduced by 20% or more, e.g., 30% or more, 40% or more, 50% or more, 60% or more, 70% or more, 80% or more, 90% or more, and up to 100%.

For example, the presence or absence of a modulatory node in the third region of the brain may be determined by applying ultrasound signals to the first region of the brain (which has a dynamic functional connection to the second region of the brain) with and without applying ultrasound signals to the third region of the brain. Upon application of ultrasound signals to the first region of the brain, neurons in the first region may generate action potentials induced by the first set of ultrasound signals. In addition, ultrasound signals may be concurrently applied to the third region of the brain. Upon application of ultrasound signals to the third region, the activity of neurons in the third region may be disrupted, for example if neurons in the third region express a mechanosensitive polypeptide as described herein. Neural activity may then be measured (e.g., fUS) in the second region of the brain, which has a dynamic functional connection to the first region of the brain. For instance, fUS can be used to measure a third change in neural activity induced by the first set of ultrasound signals in the second region of the brain without applying ultrasound signals to the third region of the brain. In some cases, the third measured change in neural activity induced by the first set of ultrasound signals in the second region of the brain without applying ultrasound signals to the third region of the brain provides a baseline measurement of the dynamic functional connection between the first region and the second region of the brain. In addition, a fourth change in neural activity induced by the first set of ultrasound signals in the second region can also be measured while ultrasound signals are applied to the third region of the brain. In some instances, there may be a difference between the third measured change in neural activity and the fourth measured change in neural activity. Based on the difference between the third measured change in neural activity and the fourth measured change in neural activity, a modulatory node in the third region of the brain may be identified. The presence of a modulatory node in the third region of the brain may be an indication of a functional connection between the third region of the brain and the first region of the brain and/or a functional connection between the third region of the brain and the second region of the brain. For instance, the modulatory node in the third region of the brain may be identified by calculating a difference between the third measured change and the fourth measured change in neural activity. If the calculated difference between the third measured change and the fourth measured change in neural activity is qualitatively or quantitatively different, this may be an indication that there is a modulatory node in the third region of the brain. For example, if the calculated difference between the third measured change and the fourth measured change in neural activity is qualitatively or quantitatively different, this may be an indication that there is a functional connection between the third region of the brain and the first region of the brain and/or a functional connection between the third region of the brain and the second region of the brain.

Aspects of the present disclosure also include a method for functional ultrasound imaging (fUS) of a subject, where the method is a compressed sensing (CS) high-resolution fUS method. Compressed sensing refers to a signal processing method where an image can be reconstructed from a series of sampling measurements obtained with a sampling rate below the Nyquist sampling rate. In general, the compressed sensing method may include obtaining one or more fUS images of a target area in a subject. For instance, in general, the method may include applying ultrasound signals to a target area in a subject to produce detectable image data (e.g., ultrasound echo signals) of the target area in the subject. In addition, the method includes acquiring the image data (e.g., with an ultrasound transducer or an array of ultrasound transducers of the fUS system) and producing an image of the target area in the subject based on the acquired image data.

The acquired image data may be saved in a computer-readable memory and analyzed at a subsequent time (also referred to herein as "offline" processing). In other cases, the acquired image data may be analyzed in real-time to produce the image of the target area in the subject. By "real-time" is meant that the acquired signals are analyzed by the fUS system (e.g., by a processor in the fUS system) immediately after signal acquisition and/or during signal acquisition.

Target Cells and Target Brain Regions

Target cells in a brain can include, but are not limited to, cholinergic neurons, GABAergic neurons, glutamatergic neurons, dopaminergic neurons, serotonergic neurons, hippocampal neurons, and the like. In some cases, target neurons are neurons present in a target brain region.

Target brain regions include, but are not limited to, the temporal lobe, the occipital lobe, the parietal lobe, the frontal lobe, the hypothalamus, the thalamus, the pituitary gland, the pineal gland, the amygdala, the hippocampus, the neocortex, and the cerebellum.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-16 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A system for functional ultrasound imaging, the system comprising:
  a) an apparatus for delivering a nucleic acid comprising a nucleotide sequence encoding a mechanosensitive ion channel to a target neural cell population in a region of the brain; and
  b) a functional ultrasound imaging device configured to:
    i) apply an ultrasound signal to the target neural cell population expressing the mechanosensitive ion channel, thereby stimulating the target neural cell population; and
    ii) image the region of the brain to produce a functional ultrasound image of the region of the brain.

Aspect 2. The system of claim 1, wherein the functional ultrasound imaging device comprises an ultrasound matrix array configured for imaging a plurality of planes in the region of the brain.

Aspect 3. The system of claim 2, wherein the ultrasound matrix array comprises a grid of ultrasound elements.

Aspect 4. The system of claim 1, wherein the functional ultrasound imaging device has a spatial resolution of 100 μm or less.

Aspect 5. The system of claim 1, wherein the functional ultrasound imaging device has a temporal resolution of 100 ms or less.

Aspect 6. The system of any one of claims 1-5, wherein the mechanosensitive ion channel is a tentonin-3 polypeptide, a piezo-1 polypeptide, a piezo-2 polypeptide, an Osca1.2 polypeptide, a TREK-1 polypeptide, a TRAAK polypeptide, a PRPV4 polypeptide, a P2X7 polypeptide, or an MscL polypeptide.

Aspect 7. The system of any one of claims 1-6, wherein the nucleotide sequence is codon optimized for expression in a human cell.

Aspect 8. The system of any one of claims 1-7, wherein the nucleotide sequence is operably linked to a promoter.

Aspect 9. The system of claim 8, wherein the promoter is an inducible promoter.

Aspect 10. A method for functional ultrasound imaging, the method comprising:
  genetically modifying a target neural cell population in a region of the brain to express a mechanosensitive ion channel;
  applying with a functional ultrasound imaging device an ultrasound signal to the target neural cell population expressing the mechanosensitive ion channel, thereby stimulating the target neural cell population; and
  imaging with the functional ultrasound imaging device the region of the brain to produce a functional ultrasound image of the region of the brain.

Aspect 11. The method of claim 10, wherein the imaging comprises producing a real-time functional ultrasound image of the region of the brain.

Aspect 12. The method of claim 10, wherein the imaging comprises producing a three-dimensional functional ultrasound image of the region of the brain.

Aspect 13. The method of claim 10, wherein the method is performed in vivo in an individual.

Aspect 14. The method of claim 10, wherein the imaging comprises scanning a second region of the brain with the functional ultrasound imaging device to observe a neural reaction in response to stimulating the target neural cell population.

Aspect 15. The method of claim 14, further comprising determining whether neural projections in the second region of the brain are connected to neural cells in the target neural cell population.

Aspect 16. The method of any one of claims 10-15, wherein the mechanosensitive ion channel is a tentonin-3 polypeptide, a piezo-1 polypeptide, a piezo-2 polypeptide, an Osca1.2 polypeptide, a TREK-1 polypeptide, a TRAAK polypeptide, a PRPV4 polypeptide, a P2X7 polypeptide, or an MscL polypeptide.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

Figure 2B:
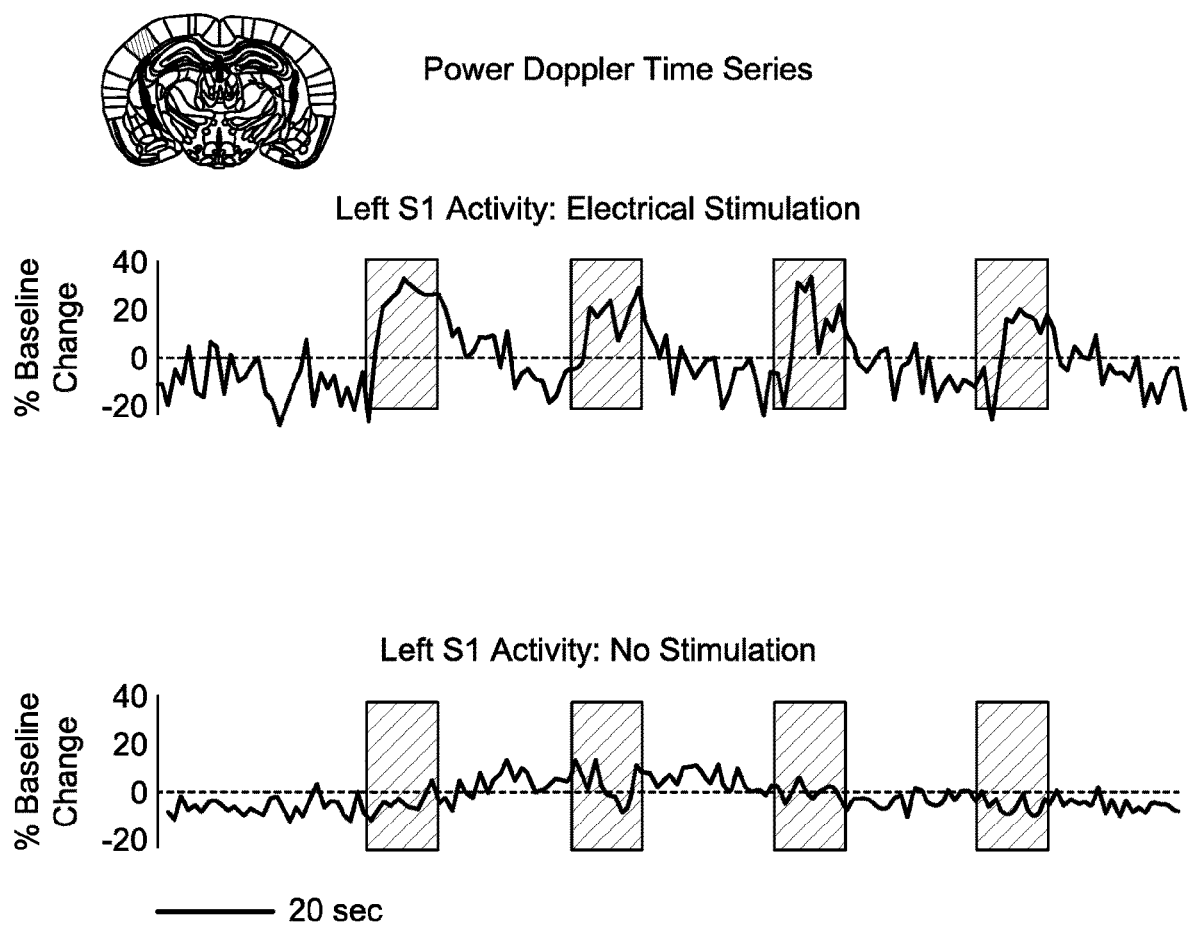
Figure 2C:
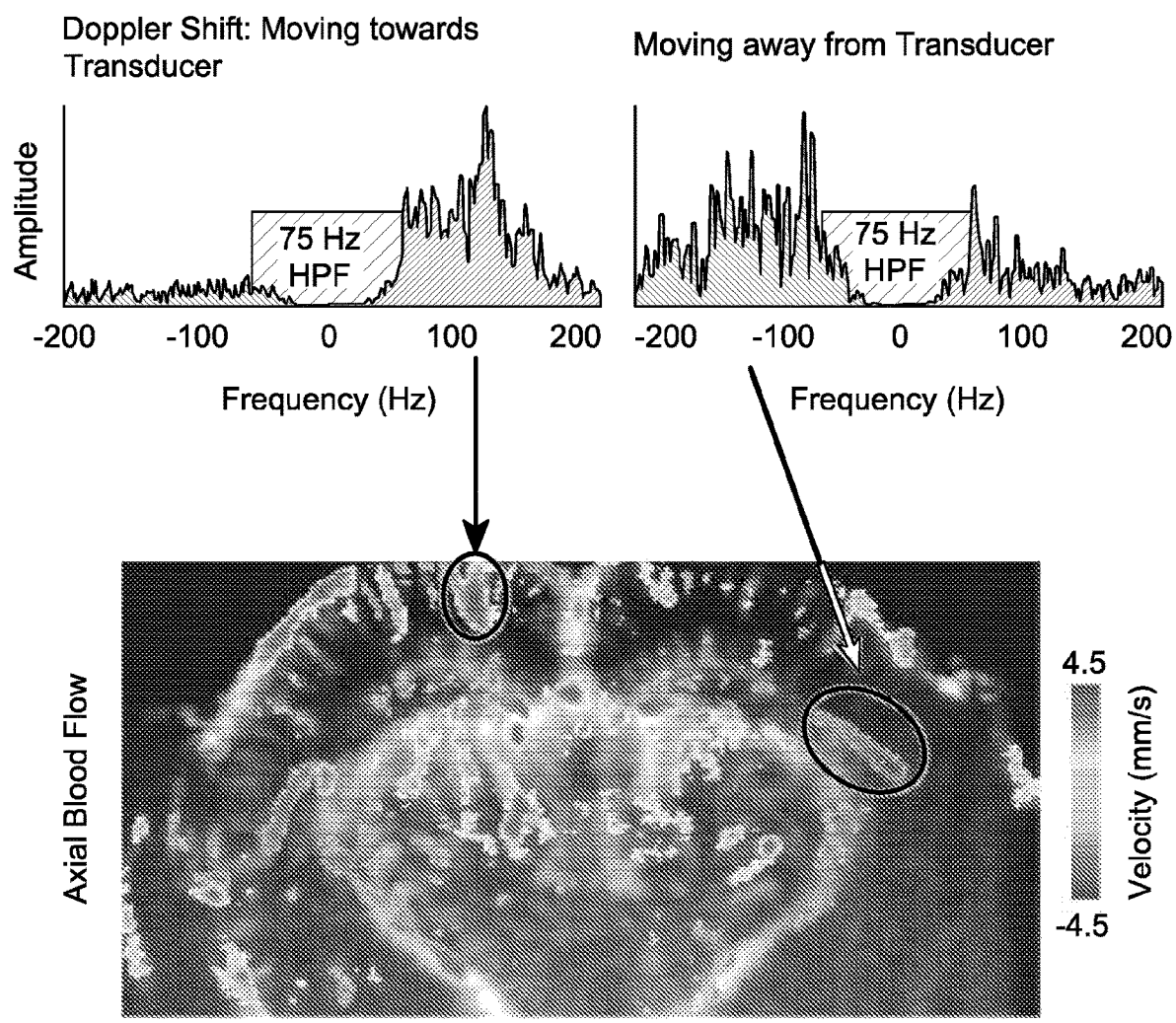

FIGS. 2A-2C depict functional ultrasound imaging. FIG. 2A Brain activation was measured by ultrafast ultrasound imaging during right hindlimb electrical stimulation in mice. (top) A 15 MHz ultrasound probe was positioned over the mouse brain in a coronal orientation at 2.06 mm behind bregma while 10 μA of electrical stimulation was applied to the right hindlimb at 5 Hz. (middle) Activation map displaying the Pearson correlation coefficient for significantly correlated pixels. Significance was determined as values greater than three times the spatial standard deviation, corresponding to $p<0.001$ (uncorrected). (bottom) Amplitude map for significantly active pixels was determined by the average % change from baseline during each of the stimulation blocks. FIG. 2B: Power doppler time series of the significantly active pixels in the left primary sensory cortex (S1) during electrical stimulation (top) and no stimulation (bottom). Blue blocks indicate stimulation blocks (if applied). FIG. 2C: (top row) Power spectrum of compound doppler images for pixels exhibiting positive (left) and negative (right) doppler shifts, corresponding to blood moving towards and away from the ultrasound transducer, respectively. (bottom) Axial blood flow map displaying the velocity of blood in various arterioles and venules.

These experiments produced images of the mouse brain while delivering low amplitude electrical stimulation to the right hind limb (FIG. 2A). Significantly activated regions were identified in the bilateral primary sensory cortices and thalamus.

Example 2

Figure 3A:
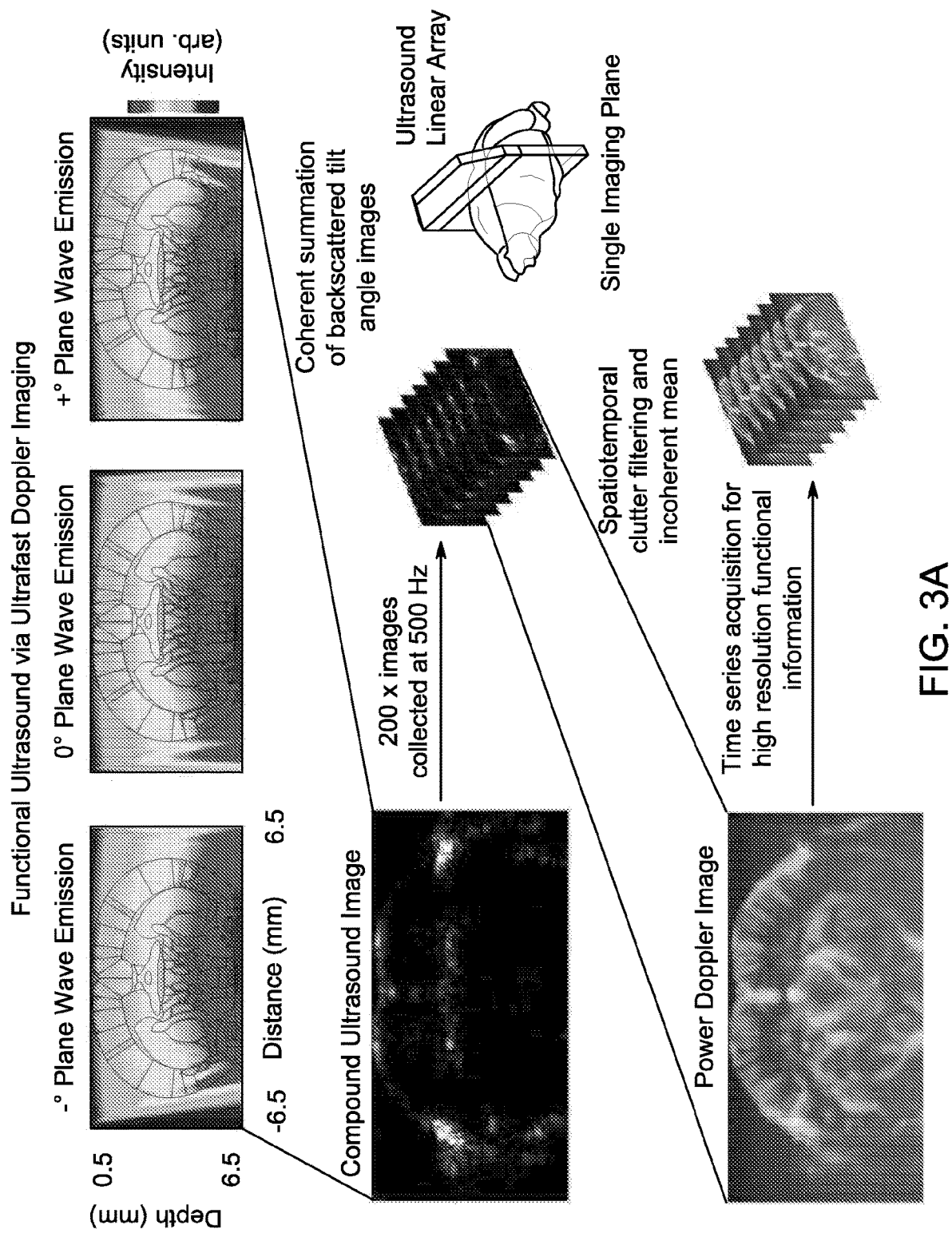
FIGS. 3A-3C depict functional ultrasound technology.
Figure 3B:
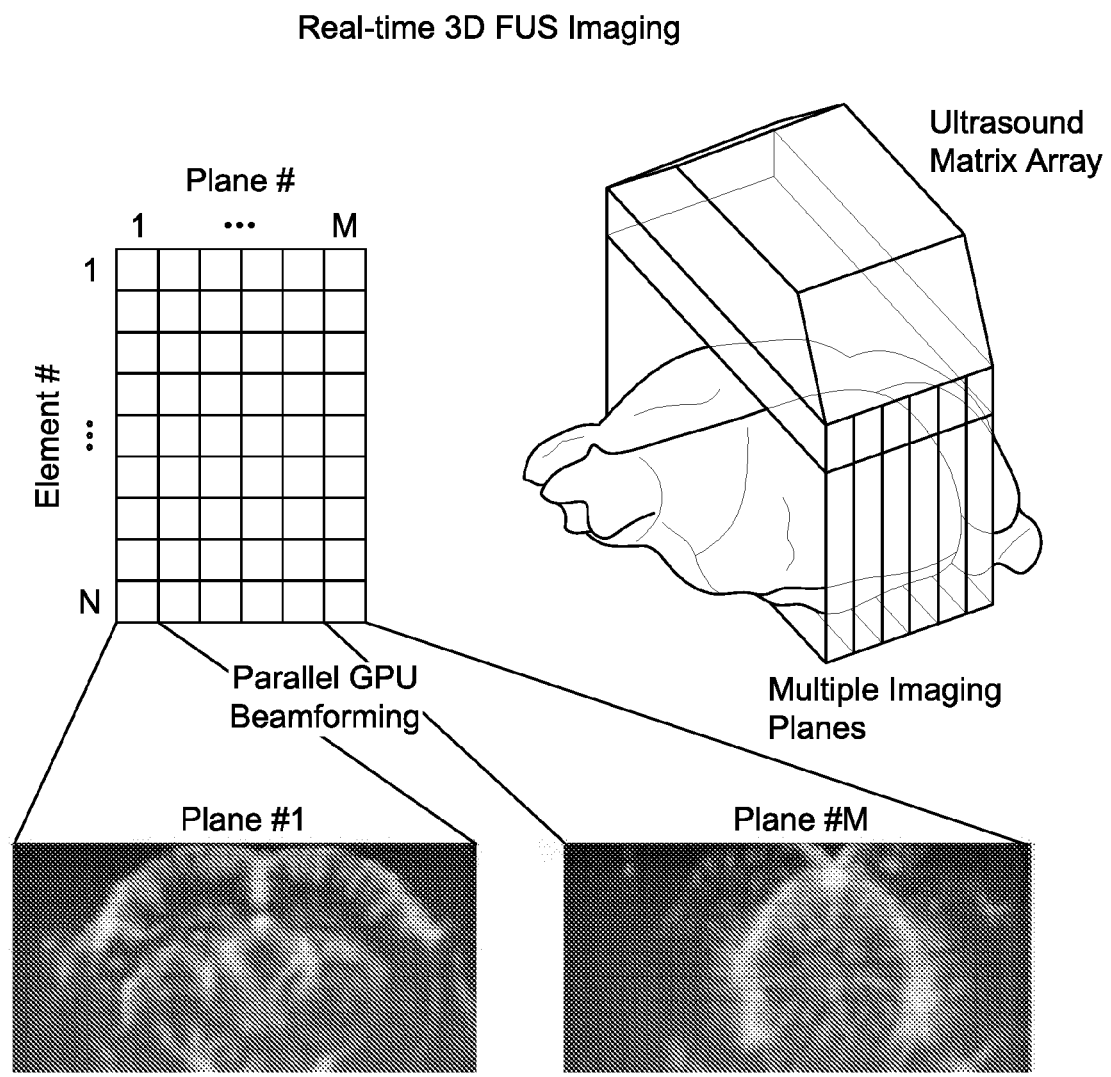
Figure 3C:
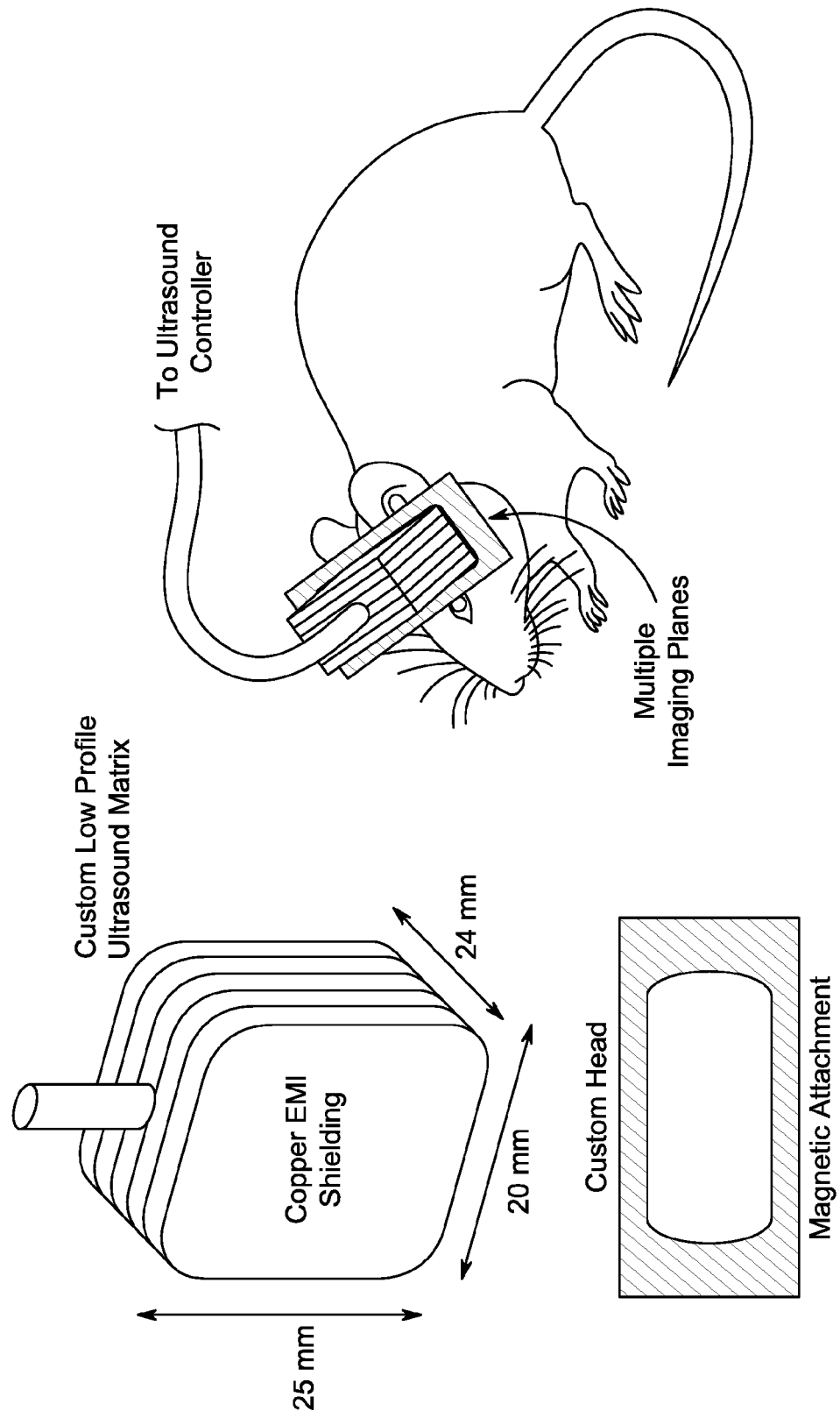

FIGS. 3A-3C depict functional ultrasound technology. FIG. 3A State-of-the-art functional ultrasound imaging technology with single-plane, head-fixed imaging capability: Biological tissue was insonified with plane waves at multiple tilt angles. The backscattered echoes were beamformed to generate low quality ultrasound images, which were then coherently summed together to generate a single compound ultrasound image. 200 of such compound images were collected at a frame rate of 500 Hz (400 ms) to capture the time-varying hemodynamic activity. Clutter filtering was then utilized to remove slow moving tissue components. The incoherent mean of this frame resulted in a single power doppler image which can be collected over time for functional information.

FIG. 3B: Real-time 3D FUS imaging: A matrix array containing a grid of ultrasound elements is programmed to insonify biological tissue in parallel at multiple planes. Parallel GPU beamforming enables image reconstruction and data compression in real time. FIG. 3C: 3D Imaging in Awake-behaving animals: schematic of a custom ultrasound matrix array with both reduced profile and weight compared to standard clinical housings. Reduction in weight of both the array and cable permits ambulation during ultrasound imaging. Magnetized head mounts fixed to the animal's head ensure a stable connection with the head while allowing for easy detachment when needed.

Real-time 3D functional ultrasound imaging system development (FIG. 3B). fUS imaging is used to provide functional information with high spatial resolution. Multi-slice fUS imaging is used to examining brain-wide circuits in three-dimensional. 3D in vivo fUS is used for imaging, demonstrating the ability to image the three dimensional structure and pulsatile flow within the carotid artery.

Compressed sensing GPU beam forming. While 3D imaging provides high spatial resolution for whole-brain imaging, the increase computation associated with acquiring multiple imaging planes can potentially lead to delays in time series. The computational efficiency of fUS image reconstructions ca be improved using compressed sensing. For real-time imaging, each data frame accommodates three steps: data acquisition using the ultrasound array, data transfer from the ultrasound controller to the host computer, and image reconstruction. Each row of the matrix array, corresponding to a single imaging plane (FIG. 3B), is controlled independently and simultaneously to insonify each brain slice of interest. Backscattered echoes are transferred to the host computer via eight PCI express lanes at a data transfer rate of 6.6 GB/s. Parallel beamforming of data from each slice is performed using a CUDA script executed in the Verasonics Matlab environment. Pulse sequence design is adjusted to accommodate this step by implementing data acquisition, data transfer, and beamforming of data frames n, n−1, and n−2 simultaneously. Beamformed images are stored in local memory until the end of a scan and are then saved to the local disk.

To reduce computational load, a custom two-fold element-by-element apodization optimization scheme is used while maintaining spatial coverage and resolution. First, low-resolution B-mode images are acquired and displayed in real time for localizing the animal brain in the field of view of the matrix array. Once correctly positioned, for each slice, elements located outside of the footprint of the brain are turned off so that extraneous signal is not unnecessarily collected. Second, a compressed sensing technique based on sparse channel estimation is used to apply appropriate channel masks without sacrificing resolution of the resulting image. Only a fraction of the available elements in the matrix array are utilized, at the benefit of significantly reduced computation time.

Whole-brain functional ultrasound in awake and freely moving animals (FIG. 3C). A low-profile ultrasound matrix array is used that significantly reduces weight compared to conventional alternatives. This array is attached to the subject's head via a permanently implanted steel plate (FIG. 3C). A magnetic sleeve is fit to the outside of the array and attaches to the steel plate with aqueous ultrasound gel in between, ensuring a direct connection between the face of the matrix array and skull. The array cable is be supported with a commutator and the magnetic connection will permit disconnection in cases where subject movement imposes high tension on the cable to avoid injury or discomfort to the subject. Real-time whole-brain imaging is performed, involving fUS imaging in awake and freely moving mice.

Define algorithms of behavioral units: The mechanogenetic functional ultrasound imaging system can facilitate flexibly select cell-type specific modulation of targets non-invasively while monitoring the outcome of such modulation across the whole brain with high spatiotemporal resolution in freely moving animals. These methods facilitate experiments for studying brain function. Experiments can be performed to observe how modulating a specific element of the brain leads to a specific behavior of interest while also directly observing the inner workings of the brain that led to such behavior. Continuous whole brain function can be matched with continuous behavior. Distinct cell type specific modulations can be intermittently applied while continuously monitoring both whole brain function and resulting behavior. Then, computational models can be constructed, algorithmically describing the brain's behavioral control.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A system for functional ultrasound imaging, the system comprising:
   a) an apparatus for delivering a nucleic acid comprising a nucleotide sequence encoding a mechanosensitive ion channel to a target neural cell population in a region of a brain; and
   b) a functional ultrasound imaging device comprising a transducer array and a processor, the ultrasound imaging device configured to:
      i) apply an ultrasound signal to the target neural cell population expressing the mechanosensitive ion channel, thereby stimulating the target neural cell population; and
      ii) image the region of the brain,
   wherein the processor is configured to independently control each row of the transducer array and simultaneously transmit plane waves in parallel slices, receive backscattered echoes generated responsive to the plane waves, and perform graphical processing unit (GPU) beamforming in parallel on the backscattered echoes to produce a functional ultrasound image of the region of the brain.

2. The system of claim 1, wherein the functional ultrasound imaging device comprises an ultrasound matrix array configured for imaging a plurality of planes in the region of the brain.

3. The system of claim 2, wherein the ultrasound matrix array comprises a curved array.

4. The system of claim 1, wherein the functional ultrasound imaging device has a spatial resolution of 100 μm or less.

5. The system of claim 1, wherein the functional ultrasound imaging device has a temporal resolution of 100 ms or less.

6. The system of claim 1, wherein the apparatus for delivering the nucleic acid comprises a reservoir, a pump, an actuator, a tubing component, a needle, a catheter, or a combination thereof.

7. The system of claim 1, wherein the apparatus for delivering the nucleic acid comprises:
   a reservoir that can contain a liquid composition comprising the nucleic acid; and
   a catheter for delivering the liquid composition from the reservoir into a subject comprising the target neural cell population.

8. The system of claim 7, wherein the apparatus for delivering the nucleic acid further comprises a pump configured to provide the liquid composition from the reservoir, through the catheter, and into the subject.

9. The system of claim 7, wherein the apparatus for delivering the nucleic acid further comprises a power source, a processor comprising a memory, a user input device, a graphical user interface, or a combination thereof.

10. A method for functional ultrasound imaging, the method comprising:
    genetically modifying a target neural cell population in a first region of a brain to express a mechanosensitive ion channel;
    applying with a functional ultrasound imaging device an ultrasound signal to the target neural cell population expressing the mechanosensitive ion channel, thereby stimulating the target neural cell population;
    imaging with the functional ultrasound imaging device the region of the brain to produce a functional ultrasound image of the first region of the brain, wherein the imaging comprises:
      transmitting plane waves; and
      performing graphical processing unit (GPU) beamforming; and
    applying a two-fold element-by-element apodization optimization scheme comprising:
      acquiring and displaying low-resolution B-mode images in real time;
      localizing the brain in the field of view of the ultrasound imaging device; and
      turning off transducer elements of the ultrasound imaging device located outside of the brain.

11. The method of claim 10, wherein the functional ultrasound image of the first region of the brain comprises a real-time functional ultrasound image of the first region of the brain.

12. The method of claim 10, wherein the functional ultrasound image of the first region of the brain comprises a three-dimensional functional ultrasound image of the first region of the brain.

13. The method of claim 10, wherein the method is performed in vivo in an individual.

14. The method of claim 10, wherein the imaging comprises scanning a second region of the brain with the functional ultrasound imaging device to observe a neural reaction in response to stimulating the target neural cell population.

15. The method of claim 14, further comprising determining whether neural projections in the second region of the brain are connected to neural cells in the target neural cell population in the first region of the brain.

16. The method of claim 10, wherein the mechanosensitive ion channel is a tentonin-3 polypeptide, a piezo-1 polypeptide, a piezo-2 polypeptide, an Osca1.2 polypeptide, a TREK-1 polypeptide, a TRAAK polypeptide, a PRPV4 polypeptide, a P2X7 polypeptide, or an MscL polypeptide.

17. The method of claim 10, wherein the imaging further comprises:
    controlling each row of a transducer array of the ultrasound imaging device independently and simultaneously to transmit the plane waves in parallel slices;
    receiving for the parallel slices backscattered echoes generated responsive to the plane waves at the transducer array; and
    performing the GPU beamforming in parallel on the backscattered echoes for each parallel slice.

18. The method of claim 10, further comprising applying a compressed sensing technique comprising sparse channel estimation to apply at least one channel mask.

19. The method of claim 10, wherein the functional ultrasound image comprises a power Doppler image.

* * * * *

SEQUENCE LISTING

<160> NUMBER OF SEQ ID NOS: 12

<210> SEQ ID NO 1
<211> LENGTH: 249
<212> TYPE: PRT
<213> ORGANISM: Homo sapiens

<400> SEQUENCE: 1

Met Asp Gly Lys Lys Cys Ser Val Trp Met Phe Leu Pro Leu Val Phe

```
            1               5                  10                 15
         Thr Leu Phe Thr Ser Ala Gly Leu Trp Ile Val Tyr Phe Ile Ala Val
                        20                 25                 30

Glu Asp Asp Lys Ile Leu Pro Leu Asn Ser Ala Glu Arg Lys Pro Gly
                        35                 40                 45

Val Lys His Ala Pro Tyr Ile Ser Ile Ala Gly Asp Asp Pro Pro Ala
                        50                 55                 60

Ser Cys Val Phe Ser Gln Val Met Asn Met Ala Ala Phe Leu Ala Leu
         65                 70                 75                 80

Val Val Ala Val Leu Arg Phe Ile Gln Leu Lys Pro Lys Val Leu Asn
                        85                 90                 95

Pro Trp Leu Asn Ile Ser Gly Leu Val Ala Leu Cys Leu Ala Ser Phe
                        100                105                110

Gly Met Thr Leu Leu Gly Asn Phe Gln Leu Thr Asn Asp Glu Glu Ile
                        115                120                125

His Asn Val Gly Thr Ser Leu Thr Phe Gly Phe Gly Thr Leu Thr Cys
                        130                135                140

Trp Ile Gln Ala Ala Leu Thr Leu Lys Val Asn Ile Lys Asn Glu Gly
         145                150                155                160

Arg Arg Val Gly Ile Pro Arg Val Ile Leu Ser Ala Ser Ile Thr Leu
                        165                170                175

Cys Val Leu Tyr Phe Ile Leu Met Ala Gln Ser Ile His Met Tyr
                        180                185                190

Ala Ala Arg Val Gln Trp Gly Leu Val Met Cys Phe Leu Ser Tyr Phe
                        195                200                205

Gly Thr Phe Ala Val Glu Phe Arg His Tyr Arg Tyr Glu Ile Val Cys
                        210                215                220

Ser Glu Tyr Gln Glu Asn Phe Leu Ser Phe Ser Glu Ser Leu Ser Glu
         225                230                235                240

Ala Ser Glu Tyr Gln Thr Asp Gln Val
                        245

<210> SEQ ID NO 2
<211> LENGTH: 2521
<212> TYPE: PRT
<213> ORGANISM: Homo sapiens

<400> SEQUENCE: 2

Met Glu Pro His Val Leu Gly Ala Val Leu Tyr Trp Leu Leu Leu Pro
         1               5                  10                 15

Cys Ala Leu Leu Ala Ala Cys Leu Leu Arg Phe Ser Gly Leu Ser Leu
                        20                 25                 30

Val Tyr Leu Leu Phe Leu Leu Leu Pro Trp Phe Pro Gly Pro Thr
                        35                 40                 45

Arg Cys Gly Leu Gln Gly His Thr Gly Arg Leu Leu Arg Ala Leu Leu
                        50                 55                 60

Gly Leu Ser Leu Leu Phe Leu Val Ala His Leu Ala Leu Gln Ile Cys
         65                 70                 75                 80

Leu His Ile Val Pro Arg Leu Asp Gln Leu Leu Gly Pro Ser Cys Ser
                        85                 90                 95

Arg Trp Glu Thr Leu Ser Arg His Ile Gly Val Thr Arg Leu Asp Leu
                        100                105                110

Lys Asp Ile Pro Asn Ala Ile Arg Leu Val Ala Pro Asp Leu Gly Ile
                        115                120                125
```

-continued

```
Leu Val Val Ser Ser Val Cys Leu Gly Ile Cys Gly Arg Leu Ala Arg
    130                 135                 140

Asn Thr Arg Gln Ser Pro His Pro Arg Glu Leu Asp Asp Glu Arg
145                 150                 155                 160

Asp Val Asp Ala Ser Pro Thr Ala Gly Leu Gln Glu Ala Ala Thr Leu
                165                 170                 175

Ala Pro Thr Arg Arg Ser Arg Leu Ala Ala Arg Phe Arg Val Thr Ala
                180                 185                 190

His Trp Leu Leu Val Ala Ala Gly Arg Val Leu Ala Val Thr Leu Leu
            195                 200                 205

Ala Leu Ala Gly Ile Ala His Pro Ser Ala Leu Ser Ser Val Tyr Leu
    210                 215                 220

Leu Leu Phe Leu Ala Leu Cys Thr Trp Trp Ala Cys His Phe Pro Ile
225                 230                 235                 240

Ser Thr Arg Gly Phe Ser Arg Leu Cys Val Ala Val Gly Cys Phe Gly
                245                 250                 255

Ala Gly His Leu Ile Cys Leu Tyr Cys Tyr Gln Met Pro Leu Ala Gln
                260                 265                 270

Ala Leu Leu Pro Pro Ala Gly Ile Trp Ala Arg Val Leu Gly Leu Lys
            275                 280                 285

Asp Phe Val Gly Pro Thr Asn Cys Ser Ser Pro His Ala Leu Val Leu
    290                 295                 300

Asn Thr Gly Leu Asp Trp Pro Val Tyr Ala Ser Pro Gly Val Leu Leu
305                 310                 315                 320

Leu Leu Cys Tyr Ala Thr Ala Ser Leu Arg Lys Leu Arg Ala Tyr Arg
                325                 330                 335

Pro Ser Gly Gln Arg Lys Glu Ala Ala Lys Gly Tyr Glu Ala Arg Glu
                340                 345                 350

Leu Glu Leu Ala Glu Leu Asp Gln Trp Pro Gln Glu Arg Glu Ser Asp
            355                 360                 365

Gln His Val Val Pro Thr Ala Pro Asp Thr Glu Ala Asp Asn Cys Ile
    370                 375                 380

Val His Glu Leu Thr Gly Gln Ser Ser Val Leu Arg Arg Pro Val Arg
385                 390                 395                 400

Pro Lys Arg Ala Glu Pro Arg Glu Ala Ser Pro Leu His Ser Leu Gly
                405                 410                 415

His Leu Ile Met Asp Gln Ser Tyr Val Cys Ala Leu Ile Ala Met Met
                420                 425                 430

Val Trp Ser Ile Thr Tyr His Ser Trp Leu Thr Phe Val Leu Leu Leu
            435                 440                 445

Trp Ala Cys Leu Ile Trp Thr Val Arg Ser Arg His Gln Leu Ala Met
    450                 455                 460

Leu Cys Ser Pro Cys Ile Leu Leu Tyr Gly Met Thr Leu Cys Cys Leu
465                 470                 475                 480

Arg Tyr Val Trp Ala Met Asp Leu Arg Pro Glu Leu Pro Thr Thr Leu
                485                 490                 495

Gly Pro Val Ser Leu Arg Gln Leu Gly Leu Glu His Thr Arg Tyr Pro
                500                 505                 510

Cys Leu Asp Leu Gly Ala Met Leu Leu Tyr Thr Leu Thr Phe Trp Leu
            515                 520                 525

Leu Leu Arg Gln Phe Val Lys Glu Lys Leu Leu Lys Trp Ala Glu Ser
    530                 535                 540

Pro Ala Ala Leu Thr Glu Val Thr Val Ala Asp Thr Glu Pro Thr Arg
```

```
            545                 550                 555                 560
        Thr Gln Thr Leu Leu Gln Ser Leu Gly Glu Leu Val Lys Gly Val Tyr
                        565                 570                 575
        Ala Lys Tyr Trp Ile Tyr Val Cys Ala Gly Met Phe Ile Val Val Ser
                        580                 585                 590
        Phe Ala Gly Arg Leu Val Val Tyr Lys Ile Val Tyr Met Phe Leu Phe
                        595                 600                 605
        Leu Leu Cys Leu Thr Leu Phe Gln Val Tyr Tyr Ser Leu Trp Arg Lys
                        610                 615                 620
        Leu Leu Lys Ala Phe Trp Trp Leu Val Val Ala Tyr Thr Met Leu Val
        625                 630                 635                 640
        Leu Ile Ala Val Tyr Thr Phe Gln Phe Gln Asp Phe Pro Ala Tyr Trp
                        645                 650                 655
        Arg Asn Leu Thr Gly Phe Thr Asp Glu Gln Leu Gly Asp Leu Gly Leu
                        660                 665                 670
        Glu Gln Phe Ser Val Ser Glu Leu Phe Ser Ser Ile Leu Val Pro Gly
                        675                 680                 685
        Phe Phe Leu Leu Ala Cys Ile Leu Gln Leu His Tyr Phe His Arg Pro
                        690                 695                 700
        Phe Met Gln Leu Thr Asp Met Glu His Val Ser Leu Pro Gly Thr Arg
        705                 710                 715                 720
        Leu Pro Arg Trp Ala His Arg Gln Asp Ala Val Ser Gly Thr Pro Leu
                        725                 730                 735
        Leu Arg Glu Glu Gln Gln Glu His Gln Gln Gln Gln Glu Glu Glu Glu
                        740                 745                 750
        Glu Glu Glu Glu Asp Ser Arg Asp Glu Gly Leu Gly Val Ala Thr Pro
                        755                 760                 765
        His Gln Ala Thr Gln Val Pro Glu Gly Ala Ala Lys Trp Gly Leu Val
                        770                 775                 780
        Ala Glu Arg Leu Leu Glu Leu Ala Ala Gly Phe Ser Asp Val Leu Ser
        785                 790                 795                 800
        Arg Val Gln Val Phe Leu Arg Arg Leu Leu Glu Leu His Val Phe Lys
                        805                 810                 815
        Leu Val Ala Leu Tyr Thr Val Trp Val Ala Leu Lys Glu Val Ser Val
                        820                 825                 830
        Met Asn Leu Leu Leu Val Val Leu Trp Ala Phe Ala Leu Pro Tyr Pro
                        835                 840                 845
        Arg Phe Arg Pro Met Ala Ser Cys Leu Ser Thr Val Trp Thr Cys Val
                        850                 855                 860
        Ile Ile Val Cys Lys Met Leu Tyr Gln Leu Lys Val Val Asn Pro Gln
        865                 870                 875                 880
        Glu Tyr Ser Ser Asn Cys Thr Glu Pro Phe Pro Asn Ser Thr Asn Leu
                        885                 890                 895
        Leu Pro Thr Glu Ile Ser Gln Ser Leu Leu Tyr Arg Gly Pro Val Asp
                        900                 905                 910
        Pro Ala Asn Trp Phe Gly Val Arg Lys Gly Phe Pro Asn Leu Gly Tyr
                        915                 920                 925
        Ile Gln Asn His Leu Gln Val Leu Leu Leu Val Phe Glu Ala Ile
                        930                 935                 940
        Val Tyr Arg Arg Gln Glu His Tyr Arg Arg Gln His Gln Leu Ala Pro
        945                 950                 955                 960
        Leu Pro Ala Gln Ala Val Phe Ala Ser Gly Thr Arg Gln Gln Leu Asp
                        965                 970                 975
```

```
Gln Asp Leu Leu Gly Cys Leu Lys Tyr Phe Ile Asn Phe Phe Phe Tyr
                980                 985                 990

Lys Phe Gly Leu Glu Ile Cys Phe  Leu Met Ala Val Asn  Val Ile Gly
                995                 1000                1005

Gln Arg Met Asn Phe Leu Val  Thr Leu His Gly Cys  Trp Leu Val
        1010                1015                1020

Ala Ile Leu Thr Arg Arg His  Arg Gln Ala Ile Ala  Arg Leu Trp
        1025                1030                1035

Pro Asn Tyr Cys Leu Phe Leu  Ala Leu Phe Leu Leu  Tyr Gln Tyr
        1040                1045                1050

Leu Leu Cys Leu Gly Met Pro  Pro Ala Leu Cys Ile  Asp Tyr Pro
        1055                1060                1065

Trp Arg Trp Ser Arg Ala Val  Pro Met Asn Ser Ala  Leu Ile Lys
        1070                1075                1080

Trp Leu Tyr Leu Pro Asp Phe  Phe Arg Ala Pro Asn  Ser Thr Asn
        1085                1090                1095

Leu Ile Ser Asp Phe Leu Leu  Leu Leu Cys Ala Ser  Gln Gln Trp
        1100                1105                1110

Gln Val Phe Ser Ala Glu Arg  Thr Glu Glu Trp Gln  Arg Met Ala
        1115                1120                1125

Gly Val Asn Thr Asp Arg Leu  Glu Pro Leu Arg Gly  Glu Pro Asn
        1130                1135                1140

Pro Val Pro Asn Phe Ile His  Cys Arg Ser Tyr Leu  Asp Met Leu
        1145                1150                1155

Lys Val Ala Val Phe Arg Tyr  Leu Phe Trp Leu Val  Leu Val Val
        1160                1165                1170

Val Phe Val Thr Gly Ala Thr  Arg Ile Ser Ile Phe  Gly Leu Gly
        1175                1180                1185

Tyr Leu Leu Ala Cys Phe Tyr  Leu Leu Leu Phe Gly  Thr Ala Leu
        1190                1195                1200

Leu Gln Arg Asp Thr Arg Ala  Arg Leu Val Leu Trp  Asp Cys Leu
        1205                1210                1215

Ile Leu Tyr Asn Val Thr Val  Ile Ile Ser Lys Asn  Met Leu Ser
        1220                1225                1230

Leu Leu Ala Cys Val Phe Val  Glu Gln Met Gln Thr  Gly Phe Cys
        1235                1240                1245

Trp Val Ile Gln Leu Phe Ser  Leu Val Cys Thr Val  Lys Gly Tyr
        1250                1255                1260

Tyr Asp Pro Lys Glu Met Met  Asp Arg Asp Gln Asp  Cys Leu Leu
        1265                1270                1275

Pro Val Glu Glu Ala Gly Ile  Ile Trp Asp Ser Val  Cys Phe Phe
        1280                1285                1290

Phe Leu Leu Leu Gln Arg Arg  Val Phe Leu Ser His  Tyr Tyr Leu
        1295                1300                1305

His Val Arg Ala Asp Leu Gln  Ala Thr Ala Leu Leu  Ala Ser Arg
        1310                1315                1320

Gly Phe Ala Leu Tyr Asn Ala  Ala Asn Leu Lys Ser  Ile Asp Phe
        1325                1330                1335

His Arg Arg Ile Glu Glu Lys  Ser Leu Ala Gln Leu  Lys Arg Gln
        1340                1345                1350

Met Glu Arg Ile Arg Ala Lys  Gln Glu Lys His Arg  Gln Gly Arg
        1355                1360                1365
```

```
Val Asp Arg Ser Arg Pro Gln Asp Thr Leu Gly Pro Lys Asp Pro
1370                1375                1380

Gly Leu Glu Pro Gly Pro Asp Ser Pro Gly Gly Ser Ser Pro Pro
1385                1390                1395

Arg Arg Gln Trp Trp Arg Pro Trp Leu Asp His Ala Thr Val Ile
1400                1405                1410

His Ser Gly Asp Tyr Phe Leu Phe Glu Ser Asp Ser Glu Glu Glu
1415                1420                1425

Glu Glu Ala Val Pro Glu Asp Pro Arg Pro Ser Ala Gln Ser Ala
1430                1435                1440

Phe Gln Leu Ala Tyr Gln Ala Trp Val Thr Asn Ala Gln Ala Val
1445                1450                1455

Leu Arg Arg Arg Gln Gln Glu Gln Glu Gln Ala Arg Gln Glu Gln
1460                1465                1470

Ala Gly Gln Leu Pro Thr Gly Gly Gly Pro Ser Gln Glu Val Glu
1475                1480                1485

Pro Ala Glu Gly Pro Glu Glu Ala Ala Ala Gly Arg Ser His Val
1490                1495                1500

Val Gln Arg Val Leu Ser Thr Ala Gln Phe Leu Trp Met Leu Gly
1505                1510                1515

Gln Ala Leu Val Asp Glu Leu Thr Arg Trp Leu Gln Glu Phe Thr
1520                1525                1530

Arg His His Gly Thr Met Ser Asp Val Leu Arg Ala Glu Arg Tyr
1535                1540                1545

Leu Leu Thr Gln Glu Leu Leu Gln Gly Gly Glu Val His Arg Gly
1550                1555                1560

Val Leu Asp Gln Leu Tyr Thr Ser Gln Ala Glu Ala Thr Leu Pro
1565                1570                1575

Gly Pro Thr Glu Ala Pro Asn Ala Pro Ser Thr Val Ser Ser Gly
1580                1585                1590

Leu Gly Ala Glu Glu Pro Leu Ser Ser Met Thr Asp Asp Met Gly
1595                1600                1605

Ser Pro Leu Ser Thr Gly Tyr His Thr Arg Ser Gly Ser Glu Glu
1610                1615                1620

Ala Val Thr Asp Pro Gly Glu Arg Glu Ala Gly Ala Ser Leu Tyr
1625                1630                1635

Gln Gly Leu Met Arg Thr Ala Ser Glu Leu Leu Leu Asp Arg Arg
1640                1645                1650

Leu Arg Ile Pro Glu Leu Glu Glu Ala Glu Leu Phe Ala Glu Gly
1655                1660                1665

Gln Gly Arg Ala Leu Arg Leu Leu Arg Ala Val Tyr Gln Cys Val
1670                1675                1680

Ala Ala His Ser Glu Leu Leu Cys Tyr Phe Ile Ile Ile Leu Asn
1685                1690                1695

His Met Val Thr Ala Ser Ala Gly Ser Leu Val Leu Pro Val Leu
1700                1705                1710

Val Phe Leu Trp Ala Met Leu Ser Ile Pro Arg Pro Ser Lys Arg
1715                1720                1725

Phe Trp Met Thr Ala Ile Val Phe Thr Glu Ile Ala Val Val Val
1730                1735                1740

Lys Tyr Leu Phe Gln Phe Gly Phe Phe Pro Trp Asn Ser His Val
1745                1750                1755

Val Leu Arg Arg Tyr Glu Asn Lys Pro Tyr Phe Pro Pro Arg Ile
```

```
                1760                1765                1770
Leu Gly Leu Glu Lys Thr Asp Gly Tyr Ile Lys Tyr Asp Leu Val
        1775                1780                1785
Gln Leu Met Ala Leu Phe Phe His Arg Ser Gln Leu Leu Cys Tyr
        1790                1795                1800
Gly Leu Trp Asp His Glu Glu Asp Ser Pro Ser Lys Glu His Asp
        1805                1810                1815
Lys Ser Gly Glu Glu Glu Gln Gly Ala Glu Gly Pro Gly Val
        1820                1825                1830
Pro Ala Ala Thr Thr Glu Asp His Ile Gln Val Glu Ala Arg Val
        1835                1840                1845
Gly Pro Thr Asp Gly Thr Pro Glu Pro Gln Val Glu Leu Arg Pro
        1850                1855                1860
Arg Asp Thr Arg Arg Ile Ser Leu Arg Phe Arg Arg Lys Lys
        1865                1870                1875
Glu Gly Pro Ala Arg Lys Gly Ala Ala Ile Glu Ala Glu Asp
        1880                1885                1890
Arg Glu Glu Glu Gly Glu Glu Lys Glu Ala Pro Thr Gly
        1895                1900                1905
Arg Glu Lys Arg Pro Ser Arg Ser Gly Arg Val Arg Ala Ala
        1910                1915                1920
Gly Arg Arg Leu Gln Gly Phe Cys Leu Ser Leu Ala Gln Gly Thr
        1925                1930                1935
Tyr Arg Pro Leu Arg Arg Phe Phe His Asp Ile Leu His Thr Lys
        1940                1945                1950
Tyr Arg Ala Ala Thr Asp Val Tyr Ala Leu Met Phe Leu Ala Asp
        1955                1960                1965
Val Val Asp Phe Ile Ile Ile Phe Gly Phe Trp Ala Phe Gly
        1970                1975                1980
Lys His Ser Ala Ala Thr Asp Ile Thr Ser Ser Leu Ser Asp Asp
        1985                1990                1995
Gln Val Pro Glu Ala Phe Leu Val Met Leu Leu Ile Gln Phe Ser
        2000                2005                2010
Thr Met Val Val Asp Arg Ala Leu Tyr Leu Arg Lys Thr Val Leu
        2015                2020                2025
Gly Lys Leu Ala Phe Gln Val Ala Leu Val Leu Ala Ile His Leu
        2030                2035                2040
Trp Met Phe Phe Ile Leu Pro Ala Val Thr Glu Arg Met Phe Asn
        2045                2050                2055
Gln Asn Val Val Ala Gln Leu Trp Tyr Phe Val Lys Cys Ile Tyr
        2060                2065                2070
Phe Ala Leu Ser Ala Tyr Gln Ile Arg Cys Gly Tyr Pro Thr Arg
        2075                2080                2085
Ile Leu Gly Asn Phe Leu Thr Lys Lys Tyr Asn His Leu Asn Leu
        2090                2095                2100
Phe Leu Phe Gln Gly Phe Arg Leu Val Pro Phe Leu Val Glu Leu
        2105                2110                2115
Arg Ala Val Met Asp Trp Val Trp Thr Asp Thr Thr Leu Ser Leu
        2120                2125                2130
Ser Ser Trp Met Cys Val Glu Asp Ile Tyr Ala Asn Ile Phe Ile
        2135                2140                2145
Ile Lys Cys Ser Arg Glu Thr Glu Lys Lys Tyr Pro Gln Pro Lys
        2150                2155                2160
```

-continued

Gly Gln Lys Lys Lys Lys Ile Val Lys Tyr Gly Met Gly Gly Leu
2165             2170                 2175

Ile Ile Leu Phe Leu Ile Ala Ile Ile Trp Phe Pro Leu Leu Phe
2180             2185                 2190

Met Ser Leu Val Arg Ser Val Val Gly Val Val Asn Gln Pro Ile
2195             2200                 2205

Asp Val Thr Val Thr Leu Lys Leu Gly Gly Tyr Glu Pro Leu Phe
2210             2215                 2220

Thr Met Ser Ala Gln Gln Pro Ser Ile Ile Pro Phe Thr Ala Gln
2225             2230                 2235

Ala Tyr Glu Glu Leu Ser Arg Gln Phe Asp Pro Gln Pro Leu Ala
2240             2245                 2250

Met Gln Phe Ile Ser Gln Tyr Ser Pro Glu Asp Ile Val Thr Ala
2255             2260                 2265

Gln Ile Glu Gly Ser Ser Gly Ala Leu Trp Arg Ile Ser Pro Pro
2270             2275                 2280

Ser Arg Ala Gln Met Lys Arg Glu Leu Tyr Asn Gly Thr Ala Asp
2285             2290                 2295

Ile Thr Leu Arg Phe Thr Trp Asn Phe Gln Arg Asp Leu Ala Lys
2300             2305                 2310

Gly Gly Thr Val Glu Tyr Ala Asn Glu Lys His Met Leu Ala Leu
2315             2320                 2325

Ala Pro Asn Ser Thr Ala Arg Arg Gln Leu Ala Ser Leu Leu Glu
2330             2335                 2340

Gly Thr Ser Asp Gln Ser Val Val Ile Pro Asn Leu Phe Pro Lys
2345             2350                 2355

Tyr Ile Arg Ala Pro Asn Gly Pro Glu Ala Asn Pro Val Lys Gln
2360             2365                 2370

Leu Gln Pro Asn Glu Glu Ala Asp Tyr Leu Gly Val Arg Ile Gln
2375             2380                 2385

Leu Arg Arg Glu Gln Gly Ala Gly Ala Thr Gly Phe Leu Glu Trp
2390             2395                 2400

Trp Val Ile Glu Leu Gln Glu Cys Arg Thr Asp Cys Asn Leu Leu
2405             2410                 2415

Pro Met Val Ile Phe Ser Asp Lys Val Ser Pro Ser Leu Gly
2420             2425                 2430

Phe Leu Ala Gly Tyr Gly Ile Met Gly Leu Tyr Val Ser Ile Val
2435             2440                 2445

Leu Val Ile Gly Lys Phe Val Arg Gly Phe Ser Glu Ile Ser
2450             2455                 2460

His Ser Ile Met Phe Glu Glu Leu Pro Cys Val Asp Arg Ile Leu
2465             2470                 2475

Lys Leu Cys Gln Asp Ile Phe Leu Val Arg Glu Thr Arg Glu Leu
2480             2485                 2490

Glu Leu Glu Glu Glu Leu Tyr Ala Lys Leu Ile Phe Leu Tyr Arg
2495             2500                 2505

Ser Pro Glu Thr Met Ile Lys Trp Thr Arg Glu Lys Glu
2510             2515                 2520

<210> SEQ ID NO 3
<211> LENGTH: 766
<212> TYPE: PRT
<213> ORGANISM: Oryza sativa

```
<400> SEQUENCE: 3

Met Ala Thr Val Ser Asp Ile Gly Leu Ser Ala Ala Ile Asn Val Ser
1               5                   10                  15

Met Ala Val Ala Phe Leu Leu Val Phe Ala Phe Leu Arg Leu Gln Pro
            20                  25                  30

Ile Asn Asp Arg Val Tyr Phe Pro Lys Trp Tyr Leu Arg Gly Met Arg
        35                  40                  45

Asp Ser Pro Val Ser Ser Gly Ala Ala Val Gln Lys Val Val Asn Leu
    50                  55                  60

Asn Met Arg Ser Tyr Leu Lys Phe Leu Ser Trp Met Pro Ala Ala Leu
65                  70                  75                  80

Lys Met Pro Glu Asp Glu Leu Ile Asn His Ala Gly Leu Asp Ser Ala
                85                  90                  95

Val Tyr Leu Arg Ile Tyr Leu Thr Gly Ile Lys Ile Phe Val Pro Ile
                100                 105                 110

Ser Ile Leu Ala Ser Leu Val Leu Phe Pro Val Asn Trp Thr Asn Asp
            115                 120                 125

Thr Leu Asp Ser Met Lys Val Val His Ser Lys Ile Asp Lys Leu Ser
130                 135                 140

Ile Ser Asn Ile Pro Tyr Gly Ser Asn Arg Phe Val Thr His Leu Val
145                 150                 155                 160

Met Ala Tyr Ala Val Thr Phe Trp Thr Cys Tyr Val Leu Phe Arg Glu
                165                 170                 175

Tyr Glu Ile Ile Thr Thr Met Arg Leu Arg Phe Leu Ala Ser Glu Lys
                180                 185                 190

Arg Arg Pro Asp Gln Phe Thr Val Leu Val Arg Asn Ile Pro Pro Asp
        195                 200                 205

Pro Asp Glu Ser Ile Ser Glu Leu Val Glu His Phe Phe Leu Val Asn
210                 215                 220

His Pro Asp His Tyr Leu Arg His Gln Val Val Tyr Asn Ala Asn Lys
225                 230                 235                 240

Leu Ala Asp Leu Val Glu Lys Lys Lys Leu Gln Asn Trp Leu Asp
            245                 250                 255

Tyr Tyr Gln Leu Lys Tyr Glu Arg Asn Pro Ser Lys Arg Pro Thr Thr
                260                 265                 270

Lys Thr Gly Phe Leu Gly Cys Phe Gly Ser Glu Val Asp Ala Ile Glu
            275                 280                 285

Tyr Tyr Lys Ala Glu Ile Glu Lys Ile Gly Lys Glu Glu Ala Asp Glu
                290                 295                 300

Arg Gln Lys Ile Met Lys Asp Pro Gln Ser Ala Val Pro Ala Ala Phe
305                 310                 315                 320

Val Ser Phe Arg Ser Arg Trp Gly Ala Ala Val Cys Ala Gln Thr Gln
                325                 330                 335

Gln Thr Ser Asn Pro Thr Val Trp Ile Thr Glu Trp Ala Pro Glu Pro
            340                 345                 350

Arg Asp Val Tyr Trp Asn Asn Leu Ser Ile Pro Phe Val Ser Leu Thr
        355                 360                 365

Val Arg Arg Leu Ile Val Ala Val Ala Phe Phe Leu Asn Phe Phe
370                 375                 380

Tyr Val Ile Pro Ile Ala Phe Val Gln Ser Leu Ala Ser Leu Glu Gly
385                 390                 395                 400

Ile Glu Lys Ala Leu Pro Phe Leu Lys Pro Leu Ile Lys Ile Asp Val
                405                 410                 415
```

Ile Lys Ser Phe Ile Gln Gly Phe Leu Pro Gly Ile Ala Leu Lys Val
            420                 425                 430

Phe Leu Ile Leu Leu Pro Thr Ile Leu Met Phe Met Ser Lys Phe Glu
        435                 440                 445

Gly Leu Ile Ser Gln Ser Ser Leu Glu Arg Arg Ser Ala Ser Lys Tyr
    450                 455                 460

Tyr Ile Phe Leu Phe Phe Asn Val Phe Leu Gly Ser Ile Val Thr Gly
465                 470                 475                 480

Ser Ala Leu Asp Gln Leu Lys Ala Tyr Ile His Gln Ser Ala Asn Glu
                485                 490                 495

Ile Pro Arg Thr Ile Gly Val Ala Ile Pro Met Arg Ala Thr Phe Phe
            500                 505                 510

Ile Thr Tyr Val Met Val Asp Gly Trp Thr Gly Val Ala Gly Glu Ile
        515                 520                 525

Leu Arg Leu Arg Ala Leu Ile Ile Phe His Leu Lys Asn Phe Phe Leu
    530                 535                 540

Val Lys Thr Glu Lys Asp Arg Glu Glu Ala Met Asp Pro Gly Ser Ile
545                 550                 555                 560

Cys Phe Asp Trp Cys Glu Pro Arg Ile Gln Leu Tyr Phe Leu Leu Gly
                565                 570                 575

Leu Val Tyr Ala Val Val Thr Pro Leu Leu Leu Pro Phe Ile Leu Val
            580                 585                 590

Phe Phe Gly Leu Ala Tyr Val Val Tyr Arg His Gln Ile Ile Asn Val
        595                 600                 605

Tyr Asn Gln Gln Tyr Glu Ser Gly Ala Gln Phe Trp Pro Ser Val His
    610                 615                 620

Gly Arg Ile Ile Ile Ala Leu Ile Val Ser Gln Leu Leu Ile Gly
625                 630                 635                 640

Leu Leu Ser Thr Lys Gly Phe Glu Glu Thr Thr Pro Val Leu Val Val
                645                 650                 655

Leu Pro Val Leu Thr Phe Trp Phe Tyr Lys Tyr Cys Lys Asn Arg Phe
            660                 665                 670

Glu Pro Ala Phe Val Arg Asn Pro Leu Gln Glu Ala Met Arg Lys Asp
        675                 680                 685

Thr Leu Glu Arg Ala Arg Glu Pro Thr Phe Asp Leu Lys Ala Tyr Leu
    690                 695                 700

Ala Asn Ala Tyr Leu His Pro Val Phe Lys Gly Arg Glu Glu Asp
705                 710                 715                 720

Asn Met Ser Ile Ser Glu Asp Val Gly Met Glu Val Ile Val Pro
                725                 730                 735

Thr Lys Arg Gln Ser Arg Arg Asn Thr Pro Ala Gln Ser Lys Tyr Glu
            740                 745                 750

Gly Ser Asp Thr Leu Ser Leu Pro Glu Thr Val His Glu Arg
        755                 760                 765

<210> SEQ ID NO 4
<211> LENGTH: 411
<212> TYPE: PRT
<213> ORGANISM: Homo sapiens

<400> SEQUENCE: 4

Met Ala Ala Pro Asp Leu Leu Asp Pro Lys Ser Ala Ala Gln Asn Ser
1               5                   10                  15

Lys Pro Arg Leu Ser Phe Ser Thr Lys Pro Thr Val Leu Ala Ser Arg

```
             20                  25                  30
Val Glu Ser Asp Thr Thr Ile Asn Val Met Lys Trp Lys Thr Val Ser
             35                  40                  45

Thr Ile Phe Leu Val Val Val Leu Tyr Leu Ile Ile Gly Ala Thr Val
         50                  55                  60

Phe Lys Ala Leu Glu Gln Pro His Glu Ile Ser Gln Arg Thr Thr Ile
 65                  70                  75                  80

Val Ile Gln Lys Gln Thr Phe Ile Ser Gln His Ser Cys Val Asn Ser
                 85                  90                  95

Thr Glu Leu Asp Glu Leu Ile Gln Gln Ile Val Ala Ala Ile Asn Ala
            100                 105                 110

Gly Ile Ile Pro Leu Gly Asn Thr Ser Asn Gln Ile Ser His Trp Asp
        115                 120                 125

Leu Gly Ser Ser Phe Phe Phe Ala Gly Thr Val Ile Thr Thr Ile Gly
        130                 135                 140

Phe Gly Asn Ile Ser Pro Arg Thr Glu Gly Gly Lys Ile Phe Cys Ile
145                 150                 155                 160

Ile Tyr Ala Leu Leu Gly Ile Pro Leu Phe Gly Phe Leu Leu Ala Gly
                165                 170                 175

Val Gly Asp Gln Leu Gly Thr Ile Phe Gly Lys Gly Ile Ala Lys Val
            180                 185                 190

Glu Asp Thr Phe Ile Lys Trp Asn Val Ser Gln Thr Lys Ile Arg Ile
        195                 200                 205

Ile Ser Thr Ile Ile Phe Ile Leu Phe Gly Cys Val Leu Phe Val Ala
        210                 215                 220

Leu Pro Ala Ile Ile Phe Lys His Ile Glu Gly Trp Ser Ala Leu Asp
225                 230                 235                 240

Ala Ile Tyr Phe Val Val Ile Thr Leu Thr Thr Ile Gly Phe Gly Asp
                245                 250                 255

Tyr Val Ala Gly Gly Ser Asp Ile Glu Tyr Leu Asp Phe Tyr Lys Pro
            260                 265                 270

Val Val Trp Phe Trp Ile Leu Val Gly Leu Ala Tyr Phe Ala Ala Val
        275                 280                 285

Leu Ser Met Ile Gly Asp Trp Leu Arg Val Ile Ser Lys Lys Thr Lys
        290                 295                 300

Glu Glu Val Gly Glu Phe Arg Ala His Ala Ala Glu Trp Thr Ala Asn
305                 310                 315                 320

Val Thr Ala Glu Phe Lys Glu Thr Arg Arg Arg Leu Ser Val Glu Ile
                325                 330                 335

Tyr Asp Lys Phe Gln Arg Ala Thr Ser Ile Lys Arg Lys Leu Ser Ala
            340                 345                 350

Glu Leu Ala Gly Asn His Asn Gln Glu Leu Thr Pro Cys Arg Arg Thr
        355                 360                 365

Leu Ser Val Asn His Leu Thr Ser Glu Arg Asp Val Leu Pro Pro Leu
        370                 375                 380

Leu Lys Thr Glu Ser Ile Tyr Leu Asn Gly Leu Thr Pro His Cys Ala
385                 390                 395                 400

Gly Glu Glu Ile Ala Val Ile Glu Asn Ile Lys
                405                 410

<210> SEQ ID NO 5
<211> LENGTH: 2752
<212> TYPE: PRT
<213> ORGANISM: Homo sapiens
```

<400> SEQUENCE: 5

```
Met Ala Ser Glu Val Val Cys Gly Leu Ile Phe Arg Leu Leu Leu Pro
1               5                   10                  15

Ile Cys Leu Ala Val Ala Cys Ala Phe Arg Tyr Asn Gly Leu Ser Phe
            20                  25                  30

Val Tyr Leu Ile Tyr Leu Leu Leu Ile Pro Leu Phe Ser Glu Pro Thr
        35                  40                  45

Lys Thr Thr Met Gln Gly His Thr Gly Arg Leu Leu Lys Ser Leu Cys
    50                  55                  60

Phe Ile Ser Leu Ser Phe Leu Leu Leu His Ile Ile Phe His Ile Thr
65                  70                  75                  80

Leu Val Ser Leu Glu Ala Gln His Arg Ile Ala Pro Gly Tyr Asn Cys
                85                  90                  95

Ser Thr Trp Glu Lys Thr Phe Arg Gln Ile Gly Phe Glu Ser Leu Lys
            100                 105                 110

Gly Ala Asp Ala Gly Asn Gly Ile Arg Val Phe Val Pro Asp Ile Gly
        115                 120                 125

Met Phe Ile Ala Ser Leu Thr Ile Trp Leu Leu Cys Arg Asn Ile Val
130                 135                 140

Gln Lys Pro Val Thr Asp Glu Ala Ala Gln Ser Asn Pro Glu Phe Glu
145                 150                 155                 160

Asn Glu Glu Leu Ala Gly Glu Lys Ile Asp Ser Glu Glu Ala Leu
                165                 170                 175

Ile Tyr Glu Glu Asp Phe Asn Gly Gly Asp Gly Val Glu Gly Glu Leu
            180                 185                 190

Glu Glu Ser Thr Lys Leu Lys Met Phe Arg Arg Leu Ala Ser Val Ala
        195                 200                 205

Ser Lys Leu Lys Glu Phe Ile Gly Asn Met Ile Thr Thr Ala Gly Lys
    210                 215                 220

Val Val Val Thr Ile Leu Leu Gly Ser Ser Gly Met Met Leu Pro Ser
225                 230                 235                 240

Leu Thr Ser Ser Val Tyr Phe Phe Val Phe Leu Gly Leu Cys Thr Trp
                245                 250                 255

Trp Ser Trp Cys Arg Thr Phe Asp Pro Leu Leu Phe Ser Cys Leu Cys
            260                 265                 270

Val Leu Leu Ala Ile Phe Thr Ala Gly His Leu Ile Gly Leu Tyr Leu
        275                 280                 285

Tyr Gln Phe Gln Phe Phe Gln Glu Ala Val Pro Pro Asn Asp Tyr Tyr
    290                 295                 300

Ala Arg Leu Phe Gly Ile Lys Ser Val Ile Gln Thr Asp Cys Ser Ser
305                 310                 315                 320

Thr Trp Lys Ile Ile Val Asn Pro Asp Leu Ser Trp Tyr His His Ala
                325                 330                 335

Asn Pro Ile Leu Leu Leu Val Met Tyr Tyr Thr Leu Ala Thr Leu Ile
            340                 345                 350

Arg Ile Trp Leu Gln Glu Pro Leu Val Gln Asp Glu Gly Thr Lys Glu
        355                 360                 365

Glu Asp Lys Ala Leu Ala Cys Ser Pro Ile Gln Ile Thr Ala Gly Arg
    370                 375                 380

Arg Arg Ser Leu Trp Tyr Ala Thr His Tyr Pro Thr Asp Glu Arg Lys
385                 390                 395                 400

Leu Leu Ser Met Thr Gln Asp Asp Tyr Lys Pro Ser Asp Gly Leu Leu
```

```
                    405                 410                 415
Val Thr Val Asn Gly Asn Pro Val Asp Tyr His Thr Ile His Pro Ser
                420                 425                 430

Leu Pro Met Glu Asn Gly Pro Gly Lys Ala Asp Leu Tyr Ser Thr Pro
            435                 440                 445

Gln Tyr Arg Trp Glu Pro Ser Asp Glu Ser Ser Glu Lys Arg Glu Glu
        450                 455                 460

Glu Glu Glu Glu Lys Glu Glu Phe Glu Glu Arg Ser Arg Glu Glu
465                 470                 475                 480

Lys Arg Ser Ile Lys Val His Ala Met Val Ser Val Phe Gln Phe Ile
                485                 490                 495

Met Lys Gln Ser Tyr Ile Cys Ala Leu Ile Ala Met Met Ala Trp Ser
                500                 505                 510

Ile Thr Tyr His Ser Trp Leu Thr Phe Val Leu Leu Ile Trp Ser Cys
            515                 520                 525

Thr Leu Trp Met Ile Arg Asn Arg Arg Lys Tyr Ala Met Ile Ser Ser
        530                 535                 540

Pro Phe Met Val Val Tyr Gly Asn Leu Leu Leu Ile Leu Gln Tyr Ile
545                 550                 555                 560

Trp Ser Phe Glu Leu Pro Glu Ile Lys Lys Val Pro Gly Phe Leu Glu
                565                 570                 575

Lys Lys Glu Pro Gly Glu Leu Ala Ser Lys Ile Leu Phe Thr Ile Thr
                580                 585                 590

Phe Trp Leu Leu Leu Arg Gln His Leu Thr Glu Gln Lys Ala Leu Gln
        595                 600                 605

Glu Lys Glu Ala Leu Leu Ser Glu Val Lys Ile Gly Ser Gln Glu Asn
    610                 615                 620

Glu Glu Lys Asp Glu Glu Leu Gln Asp Ile Gln Val Glu Gly Glu Pro
625                 630                 635                 640

Lys Glu Glu Glu Glu Glu Ala Lys Glu Glu Lys Gln Glu Arg Lys
                645                 650                 655

Lys Val Glu Gln Glu Glu Ala Glu Glu Glu Asp Glu Gln Asp Ile Met
                660                 665                 670

Lys Val Leu Gly Asn Leu Val Val Ala Met Phe Ile Lys Tyr Trp Ile
            675                 680                 685

Tyr Val Cys Gly Gly Met Phe Phe Val Ser Phe Glu Gly Lys Ile
        690                 695                 700

Val Met Tyr Lys Ile Ile Tyr Met Val Leu Phe Leu Phe Cys Val Ala
705                 710                 715                 720

Leu Tyr Gln Val His Tyr Glu Trp Trp Arg Lys Ile Leu Lys Tyr Phe
                725                 730                 735

Trp Met Ser Val Val Ile Tyr Thr Met Leu Val Leu Ile Phe Ile Tyr
                740                 745                 750

Thr Tyr Gln Phe Glu Asn Phe Pro Gly Leu Trp Gln Asn Met Thr Gly
            755                 760                 765

Leu Lys Lys Glu Lys Leu Glu Asp Leu Gly Leu Lys Gln Phe Thr Val
        770                 775                 780

Ala Glu Leu Phe Thr Arg Ile Phe Ile Pro Thr Ser Phe Leu Leu Val
785                 790                 795                 800

Cys Ile Leu His Leu His Tyr Phe His Asp Arg Phe Leu Glu Leu Thr
                805                 810                 815

Asp Leu Lys Ser Ile Pro Ser Lys Glu Asp Asn Thr Ile Tyr Arg Leu
                820                 825                 830
```

-continued

```
Ala His Pro Glu Gly Ser Leu Pro Asp Leu Thr Met Met His Leu Thr
        835                 840                 845

Ala Ser Leu Glu Lys Pro Glu Val Arg Lys Leu Ala Glu Pro Gly Glu
    850                 855                 860

Glu Lys Leu Glu Gly Tyr Ser Glu Lys Ala Gln Lys Gly Asp Leu Gly
865                 870                 875                 880

Lys Asp Ser Glu Glu Ser Glu Glu Asp Gly Glu Glu Glu Glu Glu Ser
                    885                 890                 895

Glu Glu Glu Glu Glu Thr Ser Asp Leu Arg Asn Lys Trp His Leu Val
                900                 905                 910

Ile Asp Arg Leu Thr Val Leu Phe Leu Lys Phe Leu Glu Tyr Phe His
            915                 920                 925

Lys Leu Gln Val Phe Met Trp Trp Ile Leu Glu Leu His Ile Ile Lys
        930                 935                 940

Ile Val Ser Ser Tyr Ile Ile Trp Val Ser Val Lys Glu Val Ser Leu
945                 950                 955                 960

Phe Asn Tyr Val Phe Leu Ile Ser Trp Ala Phe Ala Leu Pro Tyr Ala
                965                 970                 975

Lys Leu Arg Arg Leu Ala Ser Ser Val Cys Thr Val Thr Cys Val
            980                 985                 990

Ile Ile Val Cys Lys Met Leu Tyr Gln Leu Gln Thr Ile Lys Pro Glu
        995                 1000                1005

Asn Phe Ser Val Asn Cys Ser Leu Pro Asn Glu Asn Gln Thr Asn
        1010                1015                1020

Ile Pro Phe Asn Glu Leu Asn Lys Ser Leu Leu Tyr Ser Ala Pro
        1025                1030                1035

Ile Asp Pro Thr Glu Trp Val Gly Leu Arg Lys Ser Ser Pro Leu
        1040                1045                1050

Leu Val Tyr Leu Arg Asn Asn Leu Leu Met Leu Ala Ile Leu Ala
        1055                1060                1065

Phe Glu Val Thr Ile Tyr Arg His Gln Glu Tyr Tyr Arg Gly Arg
        1070                1075                1080

Asn Asn Leu Thr Ala Pro Val Ser Arg Thr Ile Phe His Asp Ile
        1085                1090                1095

Thr Arg Leu His Leu Asp Asp Gly Leu Ile Asn Cys Ala Lys Tyr
        1100                1105                1110

Phe Ile Asn Tyr Phe Phe Tyr Lys Phe Gly Leu Glu Thr Cys Phe
        1115                1120                1125

Leu Met Ser Val Asn Val Ile Gly Gln Arg Met Asp Phe Tyr Ala
        1130                1135                1140

Met Ile His Ala Cys Trp Leu Ile Ala Val Leu Tyr Arg Arg Arg
        1145                1150                1155

Arg Lys Ala Ile Ala Glu Ile Trp Pro Lys Tyr Cys Cys Phe Leu
        1160                1165                1170

Ala Cys Ile Ile Thr Phe Gln Tyr Phe Ile Cys Ile Gly Ile Pro
        1175                1180                1185

Pro Ala Pro Cys Arg Asp Tyr Pro Trp Arg Phe Lys Gly Ala Ser
        1190                1195                1200

Phe Asn Asp Asn Ile Ile Lys Trp Leu Tyr Phe Pro Asp Phe Ile
        1205                1210                1215

Val Arg Pro Asn Pro Val Phe Leu Val Tyr Asp Phe Met Leu Leu
        1220                1225                1230
```

-continued

Leu Cys Ala Ser Leu Gln Arg Gln Ile Phe Glu Asp Glu Asn Lys
1235                1240                1245

Ala Ala Val Arg Ile Met Ala Gly Asp Asn Val Glu Ile Cys Met
1250                1255                1260

Asn Leu Asp Ala Ala Ser Phe Ser Gln His Asn Pro Val Pro Asp
1265                1270                1275

Phe Ile His Cys Arg Ser Tyr Leu Asp Met Ser Lys Val Ile Ile
1280                1285                1290

Phe Ser Tyr Leu Phe Trp Phe Val Leu Thr Ile Ile Phe Ile Thr
1295                1300                1305

Gly Thr Thr Arg Ile Ser Ile Phe Cys Met Gly Tyr Leu Val Ala
1310                1315                1320

Cys Phe Tyr Phe Leu Leu Phe Gly Gly Asp Leu Leu Leu Lys Pro
1325                1330                1335

Ile Lys Ser Ile Leu Arg Tyr Trp Asp Trp Leu Ile Ala Tyr Asn
1340                1345                1350

Ile Phe Val Ile Thr Met Lys Asn Ile Leu Ser Ile Gly Ala Cys
1355                1360                1365

Gly Tyr Ile Gly Thr Leu Val His Asn Ser Cys Trp Leu Ile Gln
1370                1375                1380

Ala Phe Ser Leu Ala Cys Thr Val Lys Gly Tyr Gln Met Pro Ala
1385                1390                1395

Ala Asn Ser Pro Cys Thr Leu Pro Ser Gly Glu Ala Gly Ile Ile
1400                1405                1410

Trp Asp Ser Ile Cys Phe Ala Phe Leu Leu Leu Gln Arg Arg Val
1415                1420                1425

Phe Met Ser Tyr Tyr Phe Leu His Val Val Ala Asp Ile Lys Ala
1430                1435                1440

Ser Gln Ile Leu Ala Ser Arg Gly Ala Glu Leu Phe Gln Ala Thr
1445                1450                1455

Ile Val Lys Ala Val Lys Ala Arg Ile Glu Glu Glu Lys Lys Ser
1460                1465                1470

Met Asp Gln Leu Lys Arg Gln Met Asp Arg Ile Lys Ala Arg Gln
1475                1480                1485

Gln Lys Tyr Lys Lys Gly Lys Glu Arg Met Leu Ser Leu Thr Gln
1490                1495                1500

Glu Pro Gly Glu Gly Gln Asp Met Gln Lys Leu Ser Glu Glu Asp
1505                1510                1515

Asp Glu Arg Glu Ala Asp Lys Gln Lys Ala Lys Gly Lys Lys Lys
1520                1525                1530

Gln Trp Trp Arg Pro Trp Val Asp His Ala Ser Met Val Arg Ser
1535                1540                1545

Gly Asp Tyr Tyr Leu Phe Glu Thr Asp Ser Glu Glu Glu Glu Glu
1550                1555                1560

Glu Glu Leu Lys Lys Glu Asp Glu Glu Pro Pro Arg Arg Ser Ala
1565                1570                1575

Phe Gln Phe Val Tyr Gln Ala Trp Ile Thr Asp Pro Lys Thr Ala
1580                1585                1590

Leu Arg Gln Arg His Lys Glu Lys Lys Arg Ser Ala Arg Glu Glu
1595                1600                1605

Arg Lys Arg Arg Arg Lys Gly Ser Lys Glu Gly Pro Val Glu Trp
1610                1615                1620

Glu Asp Arg Glu Asp Glu Pro Ile Lys Lys Lys Ser Asp Gly Pro

```
            1625                1630                1635

Asp  Asn  Ile  Ile  Lys  Arg  Ile  Phe  Asn  Ile  Leu  Lys  Phe  Thr  Trp
            1640                1645                1650

Val  Leu  Phe  Leu  Ala  Thr  Val  Asp  Ser  Phe  Thr  Thr  Trp  Leu  Asn
            1655                1660                1665

Ser  Ile  Ser  Arg  Glu  His  Ile  Asp  Ile  Ser  Thr  Val  Leu  Arg  Ile
            1670                1675                1680

Glu  Arg  Cys  Met  Leu  Thr  Arg  Glu  Ile  Lys  Lys  Gly  Asn  Val  Pro
            1685                1690                1695

Thr  Arg  Glu  Ser  Ile  His  Met  Tyr  Tyr  Gln  Asn  His  Ile  Met  Asn
            1700                1705                1710

Leu  Ser  Arg  Glu  Ser  Gly  Leu  Asp  Thr  Ile  Asp  Glu  His  Pro  Gly
            1715                1720                1725

Ala  Ala  Ser  Gly  Ala  Gln  Thr  Ala  His  Arg  Met  Asp  Ser  Leu  Asp
            1730                1735                1740

Ser  His  Asp  Ser  Ile  Ser  Ser  Glu  Pro  Thr  Gln  Cys  Thr  Met  Leu
            1745                1750                1755

Tyr  Ser  Arg  Gln  Gly  Thr  Thr  Glu  Thr  Ile  Glu  Glu  Val  Glu  Ala
            1760                1765                1770

Glu  Gln  Glu  Glu  Glu  Ala  Gly  Ser  Thr  Ala  Pro  Glu  Pro  Arg  Glu
            1775                1780                1785

Ala  Lys  Glu  Tyr  Glu  Ala  Thr  Gly  Tyr  Asp  Val  Gly  Ala  Met  Gly
            1790                1795                1800

Ala  Glu  Glu  Ala  Ser  Leu  Thr  Pro  Glu  Glu  Glu  Leu  Thr  Gln  Phe
            1805                1810                1815

Ser  Thr  Leu  Asp  Gly  Asp  Val  Glu  Ala  Pro  Pro  Ser  Tyr  Ser  Lys
            1820                1825                1830

Ala  Val  Ser  Phe  Glu  His  Leu  Ser  Phe  Gly  Ser  Gln  Asp  Asp  Ser
            1835                1840                1845

Ala  Gly  Lys  Asn  Arg  Met  Ala  Val  Ser  Pro  Asp  Asp  Ser  Arg  Thr
            1850                1855                1860

Asp  Lys  Leu  Gly  Ser  Ser  Ile  Leu  Pro  Pro  Leu  Thr  His  Glu  Leu
            1865                1870                1875

Thr  Ala  Ser  Glu  Leu  Leu  Leu  Lys  Lys  Met  Phe  His  Asp  Asp  Glu
            1880                1885                1890

Leu  Glu  Glu  Ser  Glu  Lys  Phe  Tyr  Val  Gly  Gln  Pro  Arg  Phe  Leu
            1895                1900                1905

Leu  Leu  Phe  Tyr  Ala  Met  Tyr  Asn  Thr  Leu  Val  Ala  Arg  Ser  Glu
            1910                1915                1920

Met  Val  Cys  Tyr  Phe  Val  Ile  Ile  Leu  Asn  His  Met  Val  Ser  Ala
            1925                1930                1935

Ser  Met  Ile  Thr  Leu  Leu  Leu  Pro  Ile  Leu  Ile  Phe  Leu  Trp  Ala
            1940                1945                1950

Met  Leu  Ser  Val  Pro  Arg  Pro  Ser  Arg  Arg  Phe  Trp  Met  Met  Ala
            1955                1960                1965

Ile  Val  Tyr  Thr  Glu  Val  Ala  Ile  Val  Val  Lys  Tyr  Phe  Phe  Gln
            1970                1975                1980

Phe  Gly  Phe  Phe  Pro  Trp  Asn  Lys  Asn  Val  Glu  Val  Asn  Lys  Asp
            1985                1990                1995

Lys  Pro  Tyr  His  Pro  Pro  Asn  Ile  Ile  Gly  Val  Glu  Lys  Lys  Glu
            2000                2005                2010

Gly  Tyr  Val  Leu  Tyr  Asp  Leu  Ile  Gln  Leu  Leu  Ala  Leu  Phe  Phe
            2015                2020                2025
```

```
His Arg Ser Ile Leu Lys Cys His Gly Leu Trp Asp Glu Asp Asp
    2030              2035              2040

Met Thr Glu Ser Gly Met Ala Arg Glu Glu Ser Asp Asp Glu Leu
    2045              2050              2055

Ser Leu Gly His Gly Arg Arg Asp Ser Ser Asp Ser Leu Lys Ser
    2060              2065              2070

Ile Asn Leu Ala Ala Ser Val Glu Ser Val His Val Thr Phe Pro
    2075              2080              2085

Glu Gln Gln Thr Ala Val Arg Arg Lys Arg Ser Gly Ser Ser Ser
    2090              2095              2100

Glu Pro Ser Gln Arg Ser Ser Phe Ser Ser Asn Arg Ser Gln Arg
    2105              2110              2115

Gly Ser Thr Ser Thr Arg Asn Ser Ser Gln Lys Gly Ser Ser Val
    2120              2125              2130

Leu Ser Ile Lys Gln Lys Gly Lys Arg Glu Leu Tyr Met Glu Lys
    2135              2140              2145

Leu Gln Glu His Leu Ile Lys Ala Lys Ala Phe Thr Ile Lys Lys
    2150              2155              2160

Thr Leu Glu Ile Tyr Val Pro Ile Lys Gln Phe Phe Tyr Asn Leu
    2165              2170              2175

Ile His Pro Glu Tyr Ser Ala Val Thr Asp Val Tyr Val Leu Met
    2180              2185              2190

Phe Leu Ala Asp Thr Val Asp Phe Ile Ile Val Phe Gly Phe
    2195              2200              2205

Trp Ala Phe Gly Lys His Ser Ala Ala Ala Asp Ile Thr Ser Ser
    2210              2215              2220

Leu Ser Glu Asp Gln Val Pro Gly Pro Phe Leu Val Met Val Leu
    2225              2230              2235

Ile Gln Phe Gly Thr Met Val Val Asp Arg Ala Leu Tyr Leu Arg
    2240              2245              2250

Lys Thr Val Leu Gly Lys Val Ile Phe Gln Val Ile Leu Val Phe
    2255              2260              2265

Gly Ile His Phe Trp Met Phe Phe Ile Leu Pro Gly Val Thr Glu
    2270              2275              2280

Arg Lys Phe Ser Gln Asn Leu Val Ala Gln Leu Trp Tyr Phe Val
    2285              2290              2295

Lys Cys Val Tyr Phe Gly Leu Ser Ala Tyr Gln Ile Arg Cys Gly
    2300              2305              2310

Tyr Pro Thr Arg Val Leu Gly Asn Phe Leu Thr Lys Ser Tyr Asn
    2315              2320              2325

Tyr Val Asn Leu Phe Leu Phe Gln Gly Phe Arg Leu Val Pro Phe
    2330              2335              2340

Leu Thr Glu Leu Arg Ala Val Met Asp Trp Val Trp Thr Asp Thr
    2345              2350              2355

Thr Leu Ser Leu Ser Ser Trp Ile Cys Val Glu Asp Ile Tyr Ala
    2360              2365              2370

His Ile Phe Ile Leu Lys Cys Trp Arg Glu Ser Glu Lys Arg Tyr
    2375              2380              2385

Pro Gln Pro Arg Gly Gln Lys Lys Lys Val Lys Tyr Gly
    2390              2395              2400

Met Gly Gly Met Ile Ile Val Leu Leu Ile Cys Ile Val Trp Phe
    2405              2410              2415
```

| | | | | | | | | | | |
|---|---|---|---|---|---|---|---|---|---|---|
| Pro | Leu | Leu | Phe | Met | Ser | Leu | Ile | Lys | Ser | Val | Ala | Gly | Val | Ile |
| | 2420 | | | | 2425 | | | | 2430 | |

| | | | | | | | | | | |
|---|---|---|---|---|---|---|---|---|---|---|
| Asn | Gln | Pro | Leu | Asp | Val | Ser | Val | Thr | Ile | Thr | Leu | Gly | Gly | Tyr |
| | 2435 | | | | 2440 | | | | 2445 | |

Gln Pro Ile Phe Thr Met Ser Ala Gln Gln Ser Gln Leu Lys Ile
    2450            2455            2460

Met Asp Gln Gln Ser Phe Asn Lys Phe Ile Gln Ala Phe Ser Arg
    2465            2470            2475

Asp Thr Gly Ala Met Gln Phe Leu Glu Asn Tyr Glu Lys Glu Asp
    2480            2485            2490

Ile Thr Val Ala Glu Leu Glu Gly Asn Ser Asn Ser Leu Trp Thr
    2495            2500            2505

Ile Ser Pro Pro Ser Lys Gln Lys Met Ile His Glu Leu Leu Asp
    2510            2515            2520

Pro Asn Ser Ser Phe Ser Val Val Phe Ser Trp Ser Ile Gln Arg
    2525            2530            2535

Asn Leu Ser Leu Gly Ala Lys Ser Glu Ile Ala Thr Asp Lys Leu
    2540            2545            2550

Ser Phe Pro Leu Lys Asn Ile Thr Arg Lys Asn Ile Ala Lys Met
    2555            2560            2565

Ile Ala Gly Asn Ser Thr Glu Ser Ser Lys Thr Pro Val Thr Ile
    2570            2575            2580

Glu Lys Ile Tyr Pro Tyr Val Lys Ala Pro Ser Asp Ser Asn
    2585            2590            2595

Ser Lys Pro Ile Lys Gln Leu Leu Ser Glu Asn Phe Met Asp
    2600            2605            2610

Ile Thr Ile Ile Leu Ser Arg Asp Asn Thr Thr Lys Tyr Asn Ser
    2615            2620            2625

Glu Trp Trp Val Leu Asn Leu Thr Gly Asn Arg Ile Tyr Asn Pro
    2630            2635            2640

Asn Ser Gln Ala Leu Glu Leu Val Val Phe Asn Asp Lys Val Ser
    2645            2650            2655

Pro Pro Ser Leu Gly Phe Leu Ala Gly Tyr Gly Ile Met Gly Leu
    2660            2665            2670

Tyr Ala Ser Val Val Leu Val Ile Gly Lys Phe Val Arg Glu Phe
    2675            2680            2685

Phe Ser Gly Ile Ser His Ser Ile Met Phe Glu Glu Leu Pro Asn
    2690            2695            2700

Val Asp Arg Ile Leu Lys Leu Cys Thr Asp Ile Phe Leu Val Arg
    2705            2710            2715

Glu Thr Gly Glu Leu Glu Leu Glu Glu Asp Leu Tyr Ala Lys Leu
    2720            2725            2730

Ile Phe Leu Tyr Arg Ser Pro Glu Thr Met Ile Lys Trp Thr Arg
    2735            2740            2745

Glu Lys Thr Asn
    2750

<210> SEQ ID NO 6
<211> LENGTH: 393
<212> TYPE: PRT
<213> ORGANISM: Homo sapiens

<400> SEQUENCE: 6

Met Arg Ser Thr Thr Leu Leu Ala Leu Leu Ala Leu Val Leu Leu Tyr
1               5                   10                  15

Leu Val Ser Gly Ala Leu Val Phe Arg Ala Leu Glu Gln Pro His Glu
            20                  25                  30

Gln Gln Ala Gln Arg Glu Leu Gly Glu Val Arg Glu Lys Phe Leu Arg
        35                  40                  45

Ala His Pro Cys Val Ser Asp Gln Glu Leu Gly Leu Leu Ile Lys Glu
50                  55                  60

Val Ala Asp Ala Leu Gly Gly Ala Asp Pro Glu Thr Asn Ser Thr
65                  70                  75                  80

Ser Asn Ser Ser His Ser Ala Trp Asp Leu Gly Ser Ala Phe Phe Phe
                85                  90                  95

Ser Gly Thr Ile Ile Thr Thr Ile Gly Tyr Gly Asn Val Ala Leu Arg
            100                 105                 110

Thr Asp Ala Gly Arg Leu Phe Cys Ile Phe Tyr Ala Leu Val Gly Ile
        115                 120                 125

Pro Leu Phe Gly Ile Leu Leu Ala Gly Val Gly Asp Arg Leu Gly Ser
130                 135                 140

Ser Leu Arg His Gly Ile Gly His Ile Glu Ala Ile Phe Leu Lys Trp
145                 150                 155                 160

His Val Pro Pro Glu Leu Val Arg Val Leu Ser Ala Met Leu Phe Leu
                165                 170                 175

Leu Ile Gly Cys Leu Leu Phe Val Leu Thr Pro Thr Phe Val Phe Cys
            180                 185                 190

Tyr Met Glu Asp Trp Ser Lys Leu Glu Ala Ile Tyr Phe Val Ile Val
        195                 200                 205

Thr Leu Thr Thr Val Gly Phe Gly Asp Tyr Val Ala Gly Ala Asp Pro
210                 215                 220

Arg Gln Asp Ser Pro Ala Tyr Gln Pro Leu Val Trp Phe Trp Ile Leu
225                 230                 235                 240

Leu Gly Leu Ala Tyr Phe Ala Ser Val Leu Thr Thr Ile Gly Asn Trp
                245                 250                 255

Leu Arg Val Val Ser Arg Arg Thr Arg Ala Glu Met Gly Gly Leu Thr
            260                 265                 270

Ala Gln Ala Ala Ser Trp Thr Gly Thr Val Thr Ala Arg Val Thr Gln
        275                 280                 285

Arg Ala Gly Pro Ala Ala Pro Pro Glu Lys Glu Gln Pro Leu Leu
290                 295                 300

Pro Pro Pro Cys Pro Ala Gln Pro Leu Gly Arg Pro Arg Ser Pro
305                 310                 315                 320

Ser Pro Pro Glu Lys Ala Gln Pro Pro Ser Pro Thr Ala Ser Ala
                325                 330                 335

Leu Asp Tyr Pro Ser Glu Asn Leu Ala Phe Ile Asp Glu Ser Ser Asp
            340                 345                 350

Thr Gln Ser Glu Arg Gly Cys Pro Leu Pro Arg Ala Pro Arg Gly Arg
        355                 360                 365

Arg Arg Pro Asn Pro Pro Arg Lys Pro Val Arg Pro Arg Gly Pro Gly
370                 375                 380

Arg Pro Arg Asp Lys Gly Val Pro Val
385                 390

<210> SEQ ID NO 7
<211> LENGTH: 764
<212> TYPE: PRT
<213> ORGANISM: Homo sapiens

```
<400> SEQUENCE: 7

Met Ala Asp Ser Ser Glu Gly Pro Arg Ala Gly Pro Gly Glu Val Ala
1               5                   10                  15

Glu Leu Pro Gly Asp Glu Ser Gly Thr Pro Gly Gly Glu Ala Phe Pro
            20                  25                  30

Leu Ser Ser Leu Ala Asn Leu Phe Glu Gly Glu Asp Gly Ser Leu Ser
        35                  40                  45

Pro Ser Pro Ala Asp Ala Ser Arg Pro Ala Gly Pro Gly Asp Gly Arg
    50                  55                  60

Pro Asn Leu Arg Met Lys Phe Gln Gly Ala Phe Arg Lys Gly Val Pro
65                  70                  75                  80

Asn Pro Ile Asp Leu Leu Glu Ser Thr Leu Tyr Glu Ser Ser Val Val
                85                  90                  95

Pro Gly Pro Lys Lys Ala Pro Met Asp Ser Leu Phe Asp Tyr Gly Thr
            100                 105                 110

Tyr Arg His His Ser Ser Asp Asn Lys Arg Trp Arg Lys Lys Ile Ile
        115                 120                 125

Glu Lys Gln Pro Gln Ser Pro Lys Ala Pro Ala Pro Gln Pro Pro
    130                 135                 140

Ile Leu Lys Val Phe Asn Arg Pro Ile Leu Phe Asp Ile Val Ser Arg
145                 150                 155                 160

Gly Ser Thr Ala Asp Leu Asp Gly Leu Leu Pro Phe Leu Leu Thr His
                165                 170                 175

Lys Lys Arg Leu Thr Asp Glu Glu Phe Arg Glu Pro Ser Thr Gly Lys
            180                 185                 190

Thr Cys Leu Pro Lys Ala Leu Leu Asn Leu Ser Asn Gly Arg Asn Asp
        195                 200                 205

Thr Ile Pro Val Leu Leu Asp Ile Ala Glu Arg Thr Gly Asn Met Arg
    210                 215                 220

Glu Phe Ile Asn Ser Pro Phe Arg Asp Ile Tyr Tyr Arg Gly Glu Leu
225                 230                 235                 240

Pro Leu Ser Leu Ala Ala Cys Thr Asn Gln Pro His Ile Val Asn Tyr
                245                 250                 255

Leu Thr Glu Asn Pro His Lys Lys Ala Asp Met Arg Arg Gln Asp Ser
            260                 265                 270

Arg Gly Asn Thr Val Leu His Ala Leu Val Ala Ile Ala Asp Asn Thr
        275                 280                 285

Arg Glu Asn Thr Lys Phe Val Thr Lys Met Tyr Asp Leu Leu Leu Leu
    290                 295                 300

Lys Cys Ala Arg Leu Phe Pro Asp Ser Asn Leu Glu Ala Val Leu Asn
305                 310                 315                 320

Asn Asp Gly Leu Ser Pro Leu Met Met Ala Ala Lys Thr Gly Lys Ile
                325                 330                 335

Gly Asn Arg His Glu Met Leu Ala Val Glu Pro Ile Asn Glu Leu Leu
            340                 345                 350

Arg Asp Lys Trp Arg Lys Phe Gly Ala Val Ser Phe Tyr Ile Asn Val
        355                 360                 365

Val Ser Tyr Leu Cys Ala Met Val Ile Phe Thr Leu Thr Ala Tyr Tyr
    370                 375                 380

Gln Pro Leu Glu Gly Thr Pro Tyr Pro Tyr Arg Thr Thr Val Asp
385                 390                 395                 400

Tyr Leu Arg Leu Ala Gly Glu Val Ile Thr Leu Phe Thr Gly Val Leu
                405                 410                 415
```

```
Phe Phe Phe Thr Asn Ile Lys Asp Leu Phe Met Lys Lys Cys Pro Gly
            420                 425                 430

Val Asn Ser Leu Phe Ile Asp Gly Ser Phe Gln Leu Leu Tyr Phe Ile
        435                 440                 445

Tyr Ser Val Leu Val Ile Val Ser Ala Leu Tyr Leu Ala Gly Ile
    450                 455                 460

Glu Ala Tyr Leu Ala Val Met Val Phe Ala Leu Val Leu Gly Trp Met
465                 470                 475                 480

Asn Ala Leu Tyr Phe Thr Arg Gly Leu Lys Leu Thr Gly Thr Tyr Ser
                485                 490                 495

Ile Met Ile Gln Lys Ile Leu Phe Lys Asp Leu Phe Arg Phe Leu Leu
                500                 505                 510

Val Tyr Leu Leu Phe Met Ile Gly Tyr Ala Ser Ala Leu Val Ser Leu
        515                 520                 525

Leu Asn Pro Cys Ala Asn Met Lys Val Cys Asn Glu Asp Gln Thr Asn
    530                 535                 540

Cys Thr Val Pro Thr Tyr Pro Ser Cys Arg Asp Ser Glu Thr Phe Ser
545                 550                 555                 560

Thr Phe Leu Leu Asp Leu Phe Lys Leu Thr Ile Gly Met Gly Asp Leu
                565                 570                 575

Glu Met Leu Ser Ser Thr Lys Tyr Pro Val Val Phe Ile Ile Leu Leu
                580                 585                 590

Val Thr Tyr Ile Ile Leu Thr Phe Val Leu Leu Leu Asn Met Leu Ile
        595                 600                 605

Ala Leu Met Gly Glu Thr Val Gly Gln Val Ser Lys Glu Ser Lys His
    610                 615                 620

Ile Trp Lys Leu Gln Trp Ala Thr Thr Ile Leu Asp Ile Glu Arg Ser
625                 630                 635                 640

Phe Pro Val Phe Leu Arg Lys Ala Phe Arg Ser Gly Glu Met Val Thr
                645                 650                 655

Val Gly Lys Ser Ser Asp Gly Thr Pro Asp Arg Arg Trp Cys Phe Arg
        660                 665                 670

Val Asp Glu Val Asn Trp Ser His Trp Asn Gln Asn Leu Gly Ile Ile
    675                 680                 685

Asn Glu Asp Pro Gly Lys Asn Glu Thr Tyr Gln Tyr Tyr Gly Phe Ser
690                 695                 700

His Thr Val Gly Arg Leu Arg Arg Asp Arg Trp Ser Ser Val Val Pro
705                 710                 715                 720

Arg Val Val Glu Leu Asn Lys Asn Ser Asn Pro Asp Glu Val Val Val
                725                 730                 735

Pro Leu Asp Ser Met Gly Asn Pro Arg Cys Asp Gly His Gln Gln Gly
        740                 745                 750

Tyr Pro Arg Lys Trp Arg Thr Asp Asp Ala Pro Leu
    755                 760

<210> SEQ ID NO 8
<211> LENGTH: 595
<212> TYPE: PRT
<213> ORGANISM: Homo sapiens

<400> SEQUENCE: 8

Met Pro Ala Cys Cys Ser Cys Ser Asp Val Phe Gln Tyr Glu Thr Asn
1               5                   10                  15

Lys Val Thr Arg Ile Gln Ser Met Asn Tyr Gly Thr Ile Lys Trp Phe
```

```
            20                  25                  30
Phe His Val Ile Ile Phe Ser Tyr Val Cys Phe Ala Leu Val Ser Asp
            35                  40                  45
Lys Leu Tyr Gln Arg Lys Glu Pro Val Ile Ser Ser Val His Thr Lys
            50                  55                  60
Val Lys Gly Ile Ala Glu Val Lys Glu Glu Ile Val Glu Asn Gly Val
 65                  70                  75                  80
Lys Lys Leu Val His Ser Val Phe Asp Thr Ala Asp Tyr Thr Phe Pro
                    85                  90                  95
Leu Gln Gly Asn Ser Phe Phe Val Met Thr Asn Phe Leu Lys Thr Glu
                    100                 105                 110
Gly Gln Glu Gln Arg Leu Cys Pro Glu Tyr Pro Thr Arg Arg Thr Leu
            115                 120                 125
Cys Ser Ser Asp Arg Gly Cys Lys Lys Gly Trp Met Asp Pro Gln Ser
            130                 135                 140
Lys Gly Ile Gln Thr Gly Arg Cys Val Val His Glu Gly Asn Gln Lys
145                 150                 155                 160
Thr Cys Glu Val Ser Ala Trp Cys Pro Ile Glu Ala Val Glu Glu Ala
                    165                 170                 175
Pro Arg Pro Ala Leu Leu Asn Ser Ala Glu Asn Phe Thr Val Leu Ile
                    180                 185                 190
Lys Asn Asn Ile Asp Phe Pro Gly His Asn Tyr Thr Thr Arg Asn Ile
            195                 200                 205
Leu Pro Gly Leu Asn Ile Thr Cys Thr Phe His Lys Thr Gln Asn Pro
            210                 215                 220
Gln Cys Pro Ile Phe Arg Leu Gly Asp Ile Phe Arg Glu Thr Gly Asp
225                 230                 235                 240
Asn Phe Ser Asp Val Ala Ile Gln Gly Gly Ile Met Gly Ile Glu Ile
                    245                 250                 255
Tyr Trp Asp Cys Asn Leu Asp Arg Trp Phe His His Cys Arg Pro Lys
                    260                 265                 270
Tyr Ser Phe Arg Arg Leu Asp Asp Lys Thr Thr Asn Val Ser Leu Tyr
            275                 280                 285
Pro Gly Tyr Asn Phe Arg Tyr Ala Lys Tyr Tyr Lys Glu Asn Asn Val
            290                 295                 300
Glu Lys Arg Thr Leu Ile Lys Val Phe Gly Ile Arg Phe Asp Ile Leu
305                 310                 315                 320
Val Phe Gly Thr Gly Gly Lys Phe Asp Ile Ile Gln Leu Val Val Tyr
                    325                 330                 335
Ile Gly Ser Thr Leu Ser Tyr Phe Gly Leu Ala Thr Val Phe Ile Asp
                    340                 345                 350
Phe Leu Ile Asp Thr Tyr Ser Ser Asn Cys Cys Arg Ser His Ile Tyr
            355                 360                 365
Pro Trp Cys Lys Cys Cys Gln Pro Cys Val Val Asn Glu Tyr Tyr Tyr
            370                 375                 380
Arg Lys Lys Cys Glu Ser Ile Val Glu Pro Lys Pro Thr Leu Lys Tyr
385                 390                 395                 400
Val Ser Phe Val Asp Glu Ser His Ile Arg Met Val Asn Gln Gln Leu
                    405                 410                 415
Leu Gly Arg Ser Leu Gln Asp Val Lys Gly Gln Glu Val Pro Arg Pro
            420                 425                 430
Ala Met Asp Phe Thr Asp Leu Ser Arg Leu Pro Leu Ala Leu His Asp
            435                 440                 445
```

```
Thr Pro Pro Ile Pro Gly Gln Pro Glu Glu Ile Gln Leu Leu Arg Lys
    450                 455                 460

Glu Ala Thr Pro Arg Ser Arg Asp Ser Pro Val Trp Cys Gln Cys Gly
465                 470                 475                 480

Arg Cys Leu Pro Ser Gln Leu Pro Glu Ser His Arg Cys Leu Glu Glu
                485                 490                 495

Leu Cys Cys Arg Lys Lys Pro Gly Ala Cys Ile Thr Thr Ser Glu Leu
            500                 505                 510

Phe Arg Lys Leu Val Leu Ser Arg His Val Leu Gln Phe Leu Leu Leu
        515                 520                 525

Tyr Gln Glu Pro Leu Leu Ala Leu Asp Val Asp Ser Thr Asn Ser Arg
    530                 535                 540

Leu Arg His Cys Ala Tyr Arg Cys Tyr Ala Thr Trp Arg Phe Gly Ser
545                 550                 555                 560

Gln Asp Met Ala Asp Phe Ala Ile Leu Pro Ser Cys Cys Arg Trp Arg
                565                 570                 575

Ile Arg Lys Glu Phe Pro Lys Ser Glu Gly Gln Tyr Ser Gly Phe Lys
            580                 585                 590

Ser Pro Tyr
        595

<210> SEQ ID NO 9
<211> LENGTH: 142
<212> TYPE: PRT
<213> ORGANISM: Unknown
<220> FEATURE:
<223> OTHER INFORMATION: Rhizobiales

<400> SEQUENCE: 9

Met Leu Asn Glu Phe Lys Glu Phe Ile Ala Arg Gly Asn Val Met Asp
1               5                   10                  15

Leu Ala Val Gly Val Ile Ile Gly Ala Ala Phe Ser Lys Ile Val Asp
            20                  25                  30

Ser Val Val Asn Asp Leu Val Met Pro Val Val Gly Ala Ile Thr Gly
        35                  40                  45

Gly Gly Phe Asp Phe Ser Asn Tyr Phe Leu Pro Leu Ser Ala Ser Val
    50                  55                  60

Thr Ala Pro Thr Leu Ser Ala Ala Arg Glu Gln Gly Ala Val Phe Ala
65                  70                  75                  80

Tyr Gly Asn Phe Ile Thr Val Leu Ile Asn Phe Leu Ile Leu Ala Trp
                85                  90                  95

Ile Ile Phe Leu Leu Ile Lys Leu Val Asn Arg Ala Arg Ala Ser Val
            100                 105                 110

Glu Arg Asp Lys Ala Pro Asp Pro Ala Ala Pro Pro Gln Asp Ile
        115                 120                 125

Leu Leu Leu Ser Glu Ile Arg Asp Leu Leu Arg Gln Arg Ala
    130                 135                 140

<210> SEQ ID NO 10
<211> LENGTH: 2313
<212> TYPE: DNA
<213> ORGANISM: Oryza sativa

<400> SEQUENCE: 10
atggctaccc tgcaagatat cggcgtgagc gctggaatca acatcctctc cgcctttgtg    60
ttcttcatca tcttcgctgt gctgagactg cagccctttα acgacagggt ctacttcagc   120
```

-continued

```
aagtggtacc tgaagggact caggtccagc cctgctaggg gaggagcctt cgctcagaga    180
ttcgtgaacc tcgacttcag gagctacatg aagttcctga actggatgcc tgaggctctc    240
aaaatgcccg agcccgagct gattgatcac gccggcctgg atagcgtcgt ctatctgagg    300
atctactggc tcggcctgaa gatctttaca cctatcgccg tgctggcctg gctgtcctg    360 gtgcccgtga attggaccaa caacacactg gagatggcca acagctgag gaatgtgacc     420 tcctccgaca tcgacaaact gagcgtctcc aacatccccg agtatagcat gaggttctgg    480
acccacatcg tcatggccta cgcctttacc atctggacct gctacgtcct gatgaaggag    540
tacgagacca tcgccaacat gaggctgcag ttcgtggcca cgaagctag aaggcccgac     600 cagtttaccg tgctggtgag gaacgtgccc cctgacgctg acgaatccgt gagcgagctc    660
gtcgagcatt tcttcctggt gaaccatccc gaccactacc tgacccacca agtggtgtgc    720
aacgccaaca actcgccga cctggtcaaa aaaaaaaga agctccagaa ctggctggac      780
tactaccagc tcaagtacgc caggaacaat agccagagga ttatggtcaa gctcggcttt    840
ctgggcctct ggggccagaa ggtcgatgcc attgagcact acatcgccga gattgacaaa    900
atctccaagg agatctccaa agagagggag gaagtggtga acgaccccaa agccatcatg    960
cctgccgcct tcgtgagctt taagaccagg tgggctgccg ccgtgtgcgc tcagacccaa   1020
cagaccagaa accccaccca gtggctcacc gaatgggctc ctgaaccag ggacgtgttc     1080 tggtccaatc tggccatccc ctatgtgagc ctgaccgtga ggaggctgat tatgcacgtg   1140
gccttcttct tcctgacctt tttctttatc gtccctatcg ccttcgtcca gtccctggct   1200
accatcgaag gaattgtcaa agccgccccc ttcctcaagt tcattgtcga cgacaagttc   1260
atgaagagcg tgatccaggg attcctccct ggcattgctc tgaagctgtt cctggctttt   1320
ctcccctcca tcctgatgat catgagcaag ttcgagggct tcacctccat ctccagctta   1380
gaaaggaggg ccgccttcag atactatatt tttaacctgg tgaatgtctt tctggcctcc   1440
gtgattgctg gagccgcctt cgagcagctc aacagcttcc tcaaccagtc cgctaaccag   1500
attcctaaga ccatcggcgt ggctatcccc atgaaagcca cattctttat cacatacatt   1560
atggtggacg gatgggccgg cgtggctgga gaaatcctca tgctgaagcc tctgattatg   1620
tttcatctga aaaatgcttt tctggtgaag acagacaagg atagggagga agccatggac   1680
cctggttcta ttggctttaa cacaggcgag cccaggattc agctgtactt cctgctggga   1740
ctcgtctacg cccccgtgac acccatgctg ctgcccttta cctcgtgtt cttcgctctg    1800 gcctacattg tctacaggca ccagatcatc aacgtgtaca atcaggagta cgaatccgcc   1860
gctgccttct ggcccgacgt gcatggcaga gtgattgctg ccctggtgat cagccagctg   1920
ctcctcatgg gactgctcgg aaccaagcat gccgctctgg ccgcccctt tctgattgct    1980 ctgcccgtcc tgaccatcgg ctttcaccat ttctgcaagg gcaggtacga gcctgctttc   2040
atcaggtacc ccctgcagga agccatgatg aaggacacct tagaaacagc cagagagcct   2100
aacctcaacc tcaagggcta cctgcagaat gcctacgtgc accccgtgtt caagggcgac   2160
gaggatgact atgacatcga tgacaaactg gcaagtttg aggacgaggc tatcatcgtc    2220
cccaccaaaa ggcaatccag gagaaacacc cctgccccca gcattatctc cggcgatgat   2280
agccctagcc tgcccttttc cggcaagctc gtg                                2313
```

<210> SEQ ID NO 11
<211> LENGTH: 747
<212> TYPE: DNA

<213> ORGANISM: Homo sapiens

<400> SEQUENCE: 11

| | | | | | |
|---|---|---|---|---|---|
| atggatggga | agaaatgcag | cgtatggatg | ttcctacctc | ttgtatttac | tttgtttact | 60 |
| tcagctggat | tgtggatagt | atacttcata | gctgtggaag | atgacaaaat | tttaccatta | 120 |
| aattcagctg | aaaggaaacc | tggtgtgaag | catgcaccat | atataagcat | tgcaggtgat | 180 |
| gatcctcctg | caagctgtgt | gtttagtcaa | gttatgaaca | tggcagcctt | cctagccctt | 240 |
| gtggtagctg | ttctgcgctt | catacaactg | aaaccgaagg | ttttaaaccc | gtggctgaat | 300 |
| attagtggat | tggtggctct | gtgtctggct | tccttcggaa | tgaccttact | tggtaatttt | 360 |
| cagctcacaa | atgatgaaga | atccataac | gtcggaactt | ccttgacctt | tggatttggc | 420 |
| acattgacct | gctggatcca | ggctgcgctg | acactcaagg | tcaacatcaa | gaatgaagga | 480 |
| cggagagttg | gaattccacg | ggttattctg | tcggcatcta | tcactctctg | tgtggtcctc | 540 |
| tacttcatcc | tcatggccca | aagcatccac | atgtatgcag | ccagggtcca | gtggggcctg | 600 |
| gtcatgtgct | tcctgtctta | ttttggcacc | tttgccgtgg | agttccggca | ttaccgctat | 660 |
| gagattgttt | gctctgagta | ccaggagaat | ttcctaagct | tctcagaaag | cctgtcagaa | 720 |
| gcttctgaat | atcagactga | ccaggtg | | | | 747 |

<210> SEQ ID NO 12
<211> LENGTH: 7641
<212> TYPE: DNA
<213> ORGANISM: Mus musculus

<400> SEQUENCE: 12

| | | | | | |
|---|---|---|---|---|---|
| atggagccgc | acgtgctggg | cgccgggctc | tactggctgt | tgctgccctg | cacgctcctg | 60 |
| gcggcctccc | tgttacgctt | caatgctctc | tcgctggtct | atttgctgtt | tctactgctg | 120 |
| ctgccctggc | ttccaggccc | ctcaagacac | agcataccag | gtcacacagg | tcgcctgctc | 180 |
| cgtgcactac | tctgcctcag | cctcctcttc | tggtggccc | accttgcctt | tcagatatgc | 240 |
| ctacacaccg | tgcctcacct | ggaccagttt | ctgggacaaa | acggtagcct | tgggtgaag | 300 |
| gtgtctcaac | acataggggt | tacgaggctg | accctgaagg | acatctttaa | ccaccaccagg | 360 |
| ctggtagcac | ctgacctggg | agtgctgctg | gcgtcctccc | tttgccttgg | cctctgtgga | 420 |
| cgcctcacga | ggaaagccgg | gcagagtcgg | cgcacccagg | agctgcagga | tgatgacgat | 480 |
| gacgatgatg | acgacgatga | agacatagat | gctgccccag | ccgtggggct | gaagggagcc | 540 |
| cctgccctgg | caaccaaacg | caggctgtgg | ctggcctccc | gcttccgggt | cacggcccac | 600 |
| tggctgctga | tgacctctgg | acggacgctg | gtcattgtgt | tgctggccct | ggcaggcata | 660 |
| gcccaccctt | cggccttctc | cagcatctac | ctggtggtgt | tcctggccat | ctgcacctgg | 720 |
| tggtcctgtc | actttcctct | cagcccccctg | ggctttaaca | ccctctgtgt | catggtgagc | 780 |
| tgttttggtg | ccggccatct | catttgccta | tactgctatc | agacaccatt | tatccaggac | 840 |
| atgttacccc | ctgggaacat | ctgggccagg | ctatttggtc | tcaagaactt | cgtagacctc | 900 |
| cctaactact | ccagccccaa | cgccctggta | ctcaacacta | gcacgcctg | gcccatctat | 960 |
| gtgagtcccg | gaatcctgct | gctgctatat | tacacagcca | cctctctcct | gaagctccac | 1020 |
| aagagctgtc | cctcagagct | gaggaaggag | acacccaggg | aggatgagga | gcatgagctg | 1080 |
| gaactggacc | acctggagcc | agagcccccag | gctagggacg | ccacccaggg | tgagatgccc | 1140 |
| atgaccacgg | aacctgacct | tgacaactgc | accgtgcatg | tactaaccag | ccagagccct | 1200 |
| gtccgccagc | gtccagttcg | ccccaggctg | gctgagctga | agagatgtc | accgctacat | 1260 |

-continued

```
ggcctgggcc acctcatcat ggaccagagc tatgtgtgtg ccctgattgc catgatggtg    1320
tggagcatca tgtaccacag ttggctgacc ttcgtcctgc tgctctgggc ctgcctcatc    1380
tggacggtgc gtagccgtca ccagctggct atgctctgct cgccctgcat cctgctgtat    1440
gggctgacgc tctgctgcct gaggtatgtg tgggccatgg aacttcctga gctgcccacc    1500
accctgggcc ctgtcagcct gcaccagttg ggactggaac acacacgcta cccttgcctg    1560
gacctcggtg ccatgctcct ctatctgctc acattctggc tccttctgcg tcagttcgtg    1620
aaggagaagc tgctgaagaa gcaaaaggtg cctgcggcgc tgctggaggt cacggtggcc    1680
gacactgagc ccacacagac ccagacgctg ctgcggagcc tggggagct ggtcaccggc    1740 atctacgtca atactggat ctatgtgtgc gccggcatgt tcattgtggt cagcttcgcc    1800
ggccgcctgg tggtctacaa aatcgtctac atgttcctct tcctgctgtg cctcaccttg    1860
ttccaggtct actacaccct gtggaggaag ctgctacgtg tcttctggtg gctcgtggtg    1920
gcctatacaa tgctcgtgct catcgctgtg tacaccttcc agttccagga cttccccacc    1980
tattggcgca acctcacggg cttcacagac gagcagttgg gcgacctggg cctggagcag    2040
ttcagtgtgt cggagctctt ttccagtatc ctcatccctg gcttcttcct gctggcctgc    2100
atcctgcagc tgcactactt ccacagaccg ttcatgcagc tcactgacct ggagcacgtg    2160
ccgccaccag gcacccgcca ccctcgatgg gctcacaggc aggatgcagt gagcgaggcc    2220
cctctgcttg agcatcagga ggaagaggaa gtcttcaggg aagatgggca gagcatggat    2280
gggccccacc aggccacaca ggtccctgag ggtacggcca gcaagtgggg cctggtggct    2340
gaccggctgc tggacctagc ggccagcttc tcggctgtcc tcacccgaat ccaggtgttc    2400
gttcggcgct gctagaaact tcacgtcttc aagctggtgg ccctctacac tgtctgggtg    2460
gccctgaaag aagtgtctgt gatgaacctg ctgctggtgg tgctatgggc cttcgccttg    2520
ccctatccgc gcttccggcc catggcttcc tgcctgtcca ccgtgtggac ctgtatcatc    2580
attgtatgca agatgctcta tcagctcaag attgtcaacc gcatgagta ctccagcaac    2640 tgcactgagc ccttcccaa caataccaac ttgcagcctt tggagatcaa ccagtctttg    2700
ctgtaccgtg gccctgttga ccctgccaac tggtttgggg tgcggaaggg ttaccccaac    2760
ttgggctata tccagaacca cctgcagatc cttctgttgc tggtgtttga ggccgtggtg    2820
taccggcgcc aagagcacta ccgccggcag caccagcagg cccctctgcc cgcccaggct    2880
gtgtgcgcag atggcacccg ccagaggttg gaccaggacc tacttagctg cctcaagtat    2940
ttcatcaact tcttcttcta caaattcggg ctggagatct gcttcttgat ggccgtgaat    3000
gtgattgggc agcgtatgaa cttcatggtg atcttacacg ttgctggtt ggtggccatc    3060 cttacacgcc ggcgccgtga ggccatcgcc cgcctctggc taactactg tctgttcctc    3120 acgctgttcc tgctgtacca gtacctgctg tgtttgggca tgcccctgc actgtgcatt    3180 gactatccat ggcgctggag caaggccatc cccatgaatt ccgccctcat caagtggctg    3240
tacctacctg acttcttcag agcccccaac tccaccaacc ttatcagtga cttcctcctg    3300
ctgctttgcg cctcccagca gtggcaggtc ttctcagcgg agcgaacgga ggagtggcaa    3360
cgcatggcgc gcatcaacac tgaccacctg gagcccctgc gtgggagcc aaccctata    3420 cccaacttca tccactgcag gtcctatctg gatatgctga aggtggccgt cttccgctac    3480
ctgttctggc tggtgctcgt tgtggtgttt gttgcggggg ccacccgcat aagcatcttc    3540
gggctggggt acctgctagc ctgcttctac ctgctgctgt ttggcactac cctgctgcag    3600
```

```
aaggacacgc gagcccagct cgtgctgtgg gactgcctca tcctctataa tgtcactgtc    3660
atcatctcta agaatatgct gtcgctcctg tcctgtgtct tcgtggagca aatgcagagc    3720
aacttctgct gggtcatcca gctcttcagc ctcgtgtgca cagtcaaagg ctactatgat    3780
cccaaagaga tgatgaccag ggaccgggac tgcctgctgc ctgtggagga ggccgggatc    3840
atctgggaca gtatctgctt cttcttcctg ctcttgcaac ggcgcatctt tctcagccac    3900
tacttcctgc atgtcagcgc tgacctgaaa gccacagccc tgcaggcatc caggggcttt    3960
gccctctaca atgcagccaa cctgaagagc atcaacttcc atcgccagat tgaggagaag    4020
tccctggccc agctgaaaag acagatgaag cgcatccgtg ccaaacagga gaagtacagg    4080
cagagccagg caagtcgtgg ccaactccag tccaaagacc ctcaggatcc cagccaggag    4140
ccagggcctg acagcccagg gggctcctcc ccgccacgga gacagtggtg gcgcccctgg    4200
ctggaccacg ccacagtcat ccactctggc gactacttcc tgtttgagtc agatagcgag    4260
gaggaagagg aggccctacc tgaggacccc aggcctgcag ctcagagtgc cttccagatg    4320
gcataccagg catgggtaac caatgcccag acagtgctga ggcagcgtcg ggagcgggca    4380
cggcaggagc gggcagagca gctggcttct ggaggtgact tgaacccaga tgtggaacca    4440
gtagatgtcc cagaagatga gatggcaggc cgtagccaca tgatgcagcg tgtgctaagc    4500
accatgcagt tcctgtgggt gctgggccag gccacggtag acgggctgac gcgctggctg    4560
cgtgcattca cgaagcacca ccgcaccatg agcgatgtgc tgtgcgcaga gcgctacctg    4620
ctcacccagg agcttcttcg ggttggagag gtacgccgag gtgtgctgga ccagctttat    4680
gtgggtgaag atgaggccac attgtcaggt cccgtggaga cccggatgg acccagcaca    4740 gcctcaagtg ggctgggagc cgaagagcct ttgagtagca tgacagacga caccagcagc    4800
cccctgagca caggctataa cacccgcagt ggcagtgagg agattgtcac cgacgctggg    4860
gacctccagg ctgggacctc cctgcacggc tcccaagagc ttttagccaa tgctcgtacc    4920
cggatgcgca cggccagcga gctgctactg gataggcgcc tgcatatccc tgagctggag    4980
gaggccgagc ggtttgaggc acagcagggc cggactctgc ggctgctcag ggctgggtac    5040
cagtgcgtgg cggcacactc ggagctgctc tgttacttca tcatcatcct taaccacatg    5100
gtgacagcct cggctgcctc cctggtgctg cccgtgcttg tgttcctgtg ggccatgctg    5160
accatcccga ggcctagcaa gcgcttttgg atgacagcta tcgtcttcac tgaggtcatg    5220
gtggtcacca aatacctgtt ccagttcggc ttcttcccct ggaacagcta cgttgtgctg    5280
cggcgctatg agaacaagcc ctacttccct ccgcgaatcc tgggccttga gaaaacggac    5340
agctacatca agtatgacct ggtgcagctc atggccctct tcttccaccg ctcgcagcta    5400
ctgtgttatg gcctctggga ccatgaggag gatcgctatc caaggaccca ttgcaggagt    5460
agtgtgaagg accgggaggc caaggaagag ccagaagcta agctggaatc gcagtctgag    5520
acaggcactg gcatcccaa ggagccagtg ttggccggta ctcccaggga ccacatccaa    5580
gggaaaggaa gtattagatc caaggatgtt atccaagatc ccccagagga ccttaagccc    5640
cggcacacga ggcacatcag catacgcttc aggaggcgca aggagactcc aggacccaaa    5700
ggaacagcag tcatggagac tgagcacgag gagggagaag gaaaagaaac tacagagaga    5760
aagaggccgc gtcacactca agaaaaatcg aagtttcggg agagaatgaa ggcagctggg    5820
cgccggctgc agagcttctg tgtgtcactg gcccagagct tctaccaacc cttgcagcgt    5880
ttcttccatg acattctgca cacaaagtac cgggcggcca ccgacgtcta cgccctcatg    5940
ttcctggccg atattgtcga catcatcatc atcatctttg gtttttgggc ttttgggaag    6000
```

```
cactctgcag ccacagacat tgcatcctcg ctgtcagatg accaggtgcc acaggccttc    6060
ctgttcatgc tgctggtcca gtttggcacc atggtcatcg accgtgccct ctacctgcgc    6120
aagactgtcc tgggaaagct ggcctttcag gtggtcctgg tggtggcgat tcacatctgg    6180
atgttcttta tcttaccggc tgtcactgag aggatgttca gccagaatgc ggtggcacag    6240
ctgtggtact tcgtcaagtg catttacttt gccctgtccg cctaccagat ccgctgtggc    6300 tacccccaccc gtatcttggg caacttcctc accaagaaat acaaccatct aaacctcttc    6360
cttttccagg ggttccgtct agtgccgttc ctggtggagc tgcgggccgt catggactgg    6420
gtgtggaccg acaccacgct gtccctgtcc aactggatgt gtgtggaaga catctatgcc    6480
aacatcttta tcatcaagtg cagccgagag acagagaaga ataccccca gcccaagggg    6540 cagaagaaga agaaaattgt caagtatggt atgggaggcc tcattatcct cttcctcatc    6600
gccatcatct ggttccctct gctcttcatg tcactgatcc gctctgtggt cggggtcgtc    6660
aaccagccca ttgatgtcac cgtcaccctc aagctaggcg gctatgagcc actgttcacc    6720
atgagcgccc agcagccatc cattgtgcca ttcacacccc aggcctacga ggagctgtcc    6780
cagcagtttg acccctatcc actagccatg cagttcatta gccagtacag tcctgaggac    6840
atcgtcactg cacagatcga gggcagctcg ggggcgctgt ggcgcatcag cccacccagc    6900
cgagcccaga tgaagcagga gctgtacaac ggcacagccg acattacact gcgctttacc    6960
tggaatttcc aaagggacct ggccaagggt ggcactgtgg agtatactaa tgagaagcac    7020
accttggagc tggcccccaa cagtacggca cgaaggcagc tggcccaact gctcgagggc    7080
agacctgacc agtcagtggt cattccccat ctcttcccca agtacattcg tgctcccaat    7140
gggcctgaag ccaaccctgt gaagcagctg cagccagatg aggaagagga ctaccttggt    7200
gtgcgcatcc agctgcggag ggagcaagtg ggcacagggg cctctgggga gcaagcgggc    7260
accaaggcct ccgacttcct cgagtggtgg gtcatcgagc tgcaggactg caaggctgac    7320
tgcaacctgc tgcccatggt catcttcagt gacaaggtca gcccacctag cctgggcttc    7380
ctggccggct acgggattgt ggggctgtac gtctccatcg tgctggtggt tggcaagttt    7440
gtgcggggct tcttcagcga gatctctcac tccatcatgt tcgaggaact gccgtgtgtg    7500
gaccgcatcc tcaagctgtg ccaggacatc ttcttggtgc gcgagacccg ggagctggag    7560
ctggaggagg agctatacgc caagctcatc ttcctgtacc gatctccaga gaccatgatt    7620
aagtggacac gtgagaggga g                                              7641
```